US 7,744,901 B2

(12) United States Patent
Yang et al.

(10) Patent No.: US 7,744,901 B2
(45) Date of Patent: Jun. 29, 2010

(54) INFLUENZA HEMAGGLUTININ AND NEURAMINIDASE VARIANTS

(75) Inventors: Chin-Fen Yang, San Jose, CA (US);
George Kemble, Saratoga, CA (US);
Kanta Subbarao, Washington, DC (US);
Brian Murphy, Bethesda, MD (US)

(73) Assignees: MedImmune, LLC, Gaithersburg, MD (US); National Institute of Health, Rockville, MD (US)

( * ) Notice: Subject to any disclaimer, the term of this patent is extended or adjusted under 35 U.S.C. 154(b) by 0 days.

(21) Appl. No.: 12/354,085

(22) Filed: Jan. 15, 2009

(65) Prior Publication Data

US 2009/0136530 A1 May 28, 2009

Related U.S. Application Data

(62) Division of application No. 11/133,346, filed on May 20, 2005, now Pat. No. 7,504,109.

(60) Provisional application No. 60/657,554, filed on Feb. 28, 2005, provisional application No. 60/574,553, filed on May 25, 2004.

(51) Int. Cl.
*A61K 39/145* (2006.01)
*C12N 7/00* (2006.01)
*C12N 7/02* (2006.01)

(52) U.S. Cl. ............. 424/206.1; 424/209.1; 424/210.1; 435/235.1; 435/239

(58) Field of Classification Search ................. None
See application file for complete search history.

(56) References Cited

U.S. PATENT DOCUMENTS

| | | | |
|---|---|---|---|
| 3,992,522 A | 11/1976 | Chanock et al. | |
| 4,071,618 A | 1/1978 | Konobe et al. | |
| 4,634,666 A | 1/1987 | Engleman et al. | |
| 4,659,569 A | 4/1987 | Mitsuhashi et al. | |
| 5,166,057 A | 11/1992 | Palese et al. | |
| 5,690,937 A | 11/1997 | Parkin | |
| 5,716,821 A | 2/1998 | Wertz | |
| 5,789,229 A | 8/1998 | Wertz et al. | |
| 5,820,871 A | 10/1998 | Palese et al. | |
| 5,840,520 A | 11/1998 | Clarke | |
| 5,854,037 A | 12/1998 | Palese et al. | |
| 5,922,326 A | 7/1999 | Murphy | |
| 6,001,634 A | 12/1999 | Palese et al. | |
| 6,033,886 A | 3/2000 | Conzelmann | |
| 6,090,391 A | 7/2000 | Parkin | |
| 6,146,642 A | 11/2000 | Garcia-Sastre et al. | |
| 6,146,873 A | 11/2000 | Kistner et al. | |
| 6,168,943 B1 | 1/2001 | Rose | |
| 6,951,754 B2 | 10/2005 | Hoffmann | |
| 7,037,707 B2 | 5/2006 | Webster et al. | |
| 2002/0119445 A1 | 8/2002 | Parkin | |
| 2002/0164770 A1* | 11/2002 | Hoffmann | ............... 435/235.1 |
| 2003/0035814 A1 | 2/2003 | Kawaoka | |
| 2003/0147916 A1 | 8/2003 | Ferko | |
| 2004/0029251 A1 | 2/2004 | Hoffman et al. | |
| 2004/0137013 A1 | 7/2004 | Katinger | |
| 2005/0042229 A1 | 2/2005 | Yang | |
| 2005/0266026 A1 | 12/2005 | Hoffmann | |

FOREIGN PATENT DOCUMENTS

| | | |
|---|---|---|
| EP | 0 702 085 | 3/1996 |
| EP | 0 863 202 | 9/1998 |
| EP | 0 864 645 | 9/1998 |
| EP | 0 780 475 | 6/1999 |
| EP | 1826269 A1 | 8/2007 |
| WO | WO-91-03552 | 3/1991 |
| WO | WO-93-21306 | 10/1993 |
| WO | WO-96-10632 | 4/1996 |
| WO | WO-96-34625 | 11/1996 |
| WO | WO-97-06270 | 2/1997 |
| WO | WO-97-12032 | 4/1997 |
| WO | WO-98-02530 | 1/1998 |
| WO | WO-98-13501 | 4/1998 |
| WO | WO-98-53078 | 11/1998 |
| WO | WO-99-02657 | 1/1999 |
| WO | WO-99-15672 | 4/1999 |
| WO | WO-00-53786 | 9/2000 |
| WO | WO-00-60050 | 10/2000 |

OTHER PUBLICATIONS

Gorkova et al (Journal of Virology 79:2191-2198, Feb. 2005).*
Genbank locus AAW80717.1 (Feb. 9, 2005).*
AAW80723.1 (Feb. 9, 2005).*
Li et al (Journal of Infectious Diseases 179:1132-8, 1999) (in IDS).*
Banerjee and Barik, 1992, "Gene expression of vesicular stomatitis virus genome RNA", Virology, 188:417-428.
Baron and Barrett, 1997, "Rescue of Rinderpest Virus from Cloned cDNA", J. Virol. 71:1265-1271.
Basler et al., 1999, "Mutation of Neuraminidase Cysteine Residues Yields Temperature-Sensitive Infuenza Viruses", J. of Virology 73(10):8095-8103.

(Continued)

*Primary Examiner*—Mary E Mosher

(57) ABSTRACT

Polypeptides, polynucleotides, methods, compositions, and vaccines comprising (avian pandemic) influenza hemagglutinin and neuraminidase variants are provided.

17 Claims, 13 Drawing Sheets

OTHER PUBLICATIONS

Beare et al., 1975, "Trials in Man with Live Recombinants Made from A/PR/8/34 (HO N1) and Wild H3 N2 Influenza Viruses", Lancet 729-732.

Belshe et al. 1998, "The efficacy of live attenuated, cold-adapted, trivalent, intranasal influenza virus vaccine in children," N Engl J Med 338:1405-12.

Belshe, 1995 "A Review of Attenuation of Influenza Viruses by Genetic manipulation", American Journal of Respiratory and Critical Care Medicine 152:S72-S75.

Bender et al., 1999, "Characterization of the surface proteins of influenza A (H5N1) viruses . . . ", Virology 254(1):115-23.

Bergmann, et al., 1995, "The relative amount of an influenza A virus segment present in the viral particle is not affected . . . ", J. of Gen. Virology, 76:3211-3215.

Boyce et al., 2000, "Safety and immunogenicity of adjuvanted and unadjuvanted subunit influenza vaccines administered intranasally to healthy adults", Vaccine 19:217-26.

Boyer et al., 1994, "Infectious transcripts and cDNA clones of RNA viruses", Virology, 198:415-26.

Brandt et al., 2001, "Molecular Determinants of Virulence, Cell Tropism, and Pathogenic Phenotype of Infectious Bursal Disease Virus", Journal of Virology 75(24):11974-11982.

Brigden and Elliott, 1996, "Rescue of a Segmented Negative-Strand RNA Virus Entirely from Cloned Complementary DNAS", Proc. Natl. Acad. Sci. USA 93:15400-15404.

Buchholz et al., 1999, "Generation of Bovine Resp. Syncytial Virus (BRSV) from cDNA:BRSV NS2 Is Not Essential for Virus Replication in Tissue Culture . . . ", J. Virol. 73:251-259.

Bukreyev et al., 1996, "Recovery of infectious respiratory syncytial virus expressing an additional, foreign gene", J. Virol. 70(10):6634-41.

Castrucci et al., 1995, "Reverse genetics system for generation of an influenza A virus mutant containing a deletion of the carboxyl-terminal M2 . . . ". J.. Virol. 69(5):2725-2728.

Chen et al., 1999, "Influenza A virus NSI protein targets poly (A)-binding protein II of the cellular 3'-end processing machinery", EMBO 18:2273-2283.

Clarke et al., 2000, "Rescue of mumps virus from cDNAJ", J. Virol. 74(10):4831-4838.

Collins et al., 1991, "Rescue of Synthetic Analogs of Respiratory Syncytial Virus Genomic RNA and Effect of Truncations", Proc. Natl.. Acad. Sci. USA 88:9663-9667.

Collins et al., 1995, "Production of infectious human respiratory syncytial virus from cloned cDNA confirms and essential role . . . ", PNAS 92:11563-11567.

Collins et al., 1996, "Parainfluenza Viruses", Fields Virology, Lippincott-Raven Publishers, Phila., pp. 1205-1241.

Conzelmann et al., 1994, "Rescue of synthetic genomic RNA analogs of rabies virus by plasmid-encoded proteins", J. Virol. 68(2):713-719.

Conzelmann et al., 1996, "Genetic engineering of animal RNA viruses", Trends Microbiol. 4(10):386-393.

Conzelmann et al., 1998, "Nonsegmented negative-strand RNA viruses: genetics and manipulation of viral genomes", Ann. Rev. Genet. 32:123-162.

Conzelmann, 1996, "Genetic manipulation of non-segmented negative-strand RNA viruses", J. Gen. Virol. 77 (Pt 3):381-389.

Cox, et al.; "Identification of Sequence Changes in the Cold-Adapted, Live Attenuated Influenza Vaccine Strain, A/Ann Arbor/6/60 (H2N2)," Virology, 1988; 167: 554-567.

Database Caplus on NCBI, Accession No. AY553802, Influenza A virus (A/little grebe/Thailand/Phichit-01/2004(H5N1) hemagglutinin (HA) gene, partial cds. May 21, 2004.

De and Banerjee, 1985, "Requirements and Functions of Vesicular Stomatitis Virus L and NS Proteins in the Transcription . . . ", Biochem. & Biophys. Res. Communc. 126:40-49.

De and Banerjee, 1993, "Rescue of synthetic analogs of genome RNA of human parainfluenza virus type 3", Virology, 96:344-348.

De and Banerjee, 1994, "Reverse genetics of negative strand RNA viruses", Indian J. Biochem & Biophys. 31:367-376.

De et al., "Complete sequence of a cDNA clone of the hemagglutinin gene of influenza A/Chicken/Scotland/59 (H5N1) virus: comparison with contemporary North American and European strains", Nucleic Acids Research, 1988. vol. 16, No. 9, pp. 4181-4182.

De et al., "Protection against virulent H5 avian influenza virus infection in chickens by an inactivated vaccine produced with recombinant vaccine virus", Jun. 1988, Vaccine, vol. 6, pp. 257-261.

De la Luna et al., 1993, "Influenza virus naked RNA can be expressed upon transfection into cells co-expressing the three subunits . . . ", J. Gen. Virol. 74:535-539.

De la Luna et al., 1995, Influenza virus NSI Protein Enhances the Rate of Translation Initiation of Viral mRNAs :, J. of Virol. 69:2427-2433.

Dimock et al., 1993, "Rescue of synthetic analogs of genomic RNA and replicative-intermed. RNA of human parainfluenza virus type 3", J. Virol. 67(5):2772-2778.

Dreher and Hall, 1988, "Mutational Analysis of the Sequence and Structural Requirements in Brome Mosaic Virus RNA for Minus Strand Promoter Activity", J. Mol. Biol. 201:31-40.

Dreher et al., 1984, "Mutant Viral RNAs Synthesized into vitro Show Altered Aminoacylation and Replicase Template Activities", Nature 311:171-175.

Dunn et al., 1995, "Transcription of a recombinant bunyavirus RNA template by transiently expressed bunyavirus proteins", Virology, 211:133-143.

Durbin et al., 1997, "Recovery of infectious Human Parainfluenza Virus Type 3 from cDNA", Virol. 235:323-332.

Edwards et al., 1994, "A randomized controlled trial of cold adapted and inactivated vaccines for the prevention of influenza A disease", J Infect Dis 169:68-76.

Egorov et al., 1998, "Transfectant Influenza A Viruses with Long Deletions in the NS1 Protein Grow Efficiently in Vero Cells", J. of Virology 72(8):6437-6441.

Elliott et al., 1991, "Some highlights of virus research in 1990", J. Gen. Virol. 72:1761-1779. Review.

Elliott et al., 1997, Abstract #96 10. sup.th international conference on Negative Strand Viruses.

Emerson and Yu, 1975, "Both NS and L Proteins are Required for in vitro RNA Synthesis by Vosicular Stomatitis Virus", J. Virol. 15:1348-1356.

Enami and Palese, 1991, "High-Efficiency Formation of Influenza Virus Transfectants", J. Virol. 65:2711-2713.

Enami et al., 1990, "Introduction of Site Specific Mutations into the Genome of Influenza Virus", Proc Natl Acad Sci USA 87: 3802-3805.

Enami et al., 1991, "An influenza virus containing nine different RNA segments", Virology. 185:291-98.

Enami et al., 2000, "Characterization of Influenza Virus NS1 Protein by Using a Novel Helper-Virus Free Reverse Genetic System", J. of Virology 74(12):5556-5561.

Erich Hoffmann et al., 2000 "Characterization of the Influenza A Virus Gene Pool in Avian Species in Southern China: Was H6N1 . . . ?" J. Virology, 74(14):6309-6315.

Erich Hoffmann et al., 2002, "Rescue of influenza B virus from eight plasmids", PNAS 99: 11411-11416.

Fahey and Schooley, 1992, "Status of Immune-Based Therapies in HIV Infection and AIDS", Clin. Exp. Immunol. 88:1-5.

Flandorfer et al., 2003, "Chimeric Influenza A Viruses with a Functional Influenza B Virus Neuraminidase or Hemagglutinin", J. of Virology 77(17):9116-9123.

Flick, et al., "Promoter elements in the influenza vRNA terminal structure," RNA, 1996; 2(10):1046-1057.

Fodor et al., 1999, "Rescue of Influenza A Virus from Recombinant DNA", J. of Virology 73(11):9679-9682.

Fortes et al., 1994, "Influenza virus NS1 protein inhibits pre-mRNA splicing and blocks mRNA nucleocytoplasmic transport", EMBO J. 13: 704-712.

Furminger, "Vaccine Production", Textbook of Influenza, pp. 324-332; (1996).

Garcia-Sastre A, Palese P, 1993. "Genetic manipulation of negative-strand RNA virus genomes", Annu Rev Microbiol. 47:765-90.

Garcin et al., 1995, "A highly recombinogenic system for the recovery of infectious sendai paramyxovirus from cDNA: generation of a novel . . . " EMBO J. 14: 6087-6094.

GenBank AF046080. 1 May 17, 2005.
GenBank AF046097. 1 May 17, 2005.
Ghendon, "Cold-Adapted, Live Influenza Vaccines Developed in Russia," Textbook of Influenza, Chapter 29, pp. 391-399, (1998).
Goto et al.,1997, "Mutations Affecting the Sensitivity of the Influenza Virus Neuraminidase to 4-Guanidino-2,4-Dideoxy-2,3 Dehydro-N-Acetyineuraminic Acid", Virol. 238:265-27.
Govorkova, E.A., et al., "African Green Monkey Kidney (Vero) Cells Provide an Alternative Host Cell . . . ", J. of Virology, Am. Soc. for Microbiology, Aug. 1996, 70(8):5519-5524.
Grosfeld et al., 1995, "RNA replication by respiratory syncytial virus (RSV) is directed by the N., P., and L proteins: transcription . . . " J. Virol. 69(9):5677-86.
Guan, Yi, et al., "Molecular Characterization of H9N2 Influenza Viruses: Were They The Donors of the "Internal" . . . ?", Proc. Natl. Acad. Sci., U.S.A. Aug. 1999, 96:9363-9367.
Hatada and Fukudo, 1992, "Binding of influenza A virus NS1 protein to dsRNA in vitro", J. of Gen. Virol. 73: 3325-3329.
He et al., 1997, "Recovery of Infectious SV5 from Cloned DNA and Expression of a Foreign Gene", Virol. 237:249-260.
Herlocher et al., "Sequence Comparisons of A/AA/6/60 Influenza Viruses: Mutations Which May Contribute to Attenuation", Virus Research, 42:11-25; (1996).
Hillman Maurice R., 2000, "Vaccines in historic evolution and perspective: a narrative of vaccine discoveries", Vaccine 18:1436-1447.
Hiromoto et al., 2000,. "Evolutionary characterization of the six internal genes of H5N1 human influenza A virus . . . ", J. Gen. Virol. 81(Pt5):1293-303.
Hoffman and Banerjee, 1997. "An Infectious Clone of Human Parainfluenza Virus Type 3", J. Virol. 71:4272-4277.
Hoffmann et al."Universal primer set for the full-length amplification of all influenza A viruses." Arch Virol. Dec. 2001;146(12):2275-89.
Hoffmann et al., "Ambisense" Approach for the Generation of Influenza A Virus: vRNA and mRNA Synthesis from One Template, Virology, 267:310-317; (2000).
Hoffmann et al., "Eight-Plasmid Resue System for Influenza A Virus", International Congress Series, 1219:1007-1013; (2001).
Hoffmann et al., "Eight-Plasmid System for Rapid Generation of Influenza Virus Vaccines", Vaccine, 20:3165-3170; (2002).
Hoffmann et al., 2000, "A DNA transfection system for generation of influenza A virus from eight plasmids", PNAS 97(11):6108-6113.
Hoffmann et al., 2005, "Role of specific hemagglutinin amino acids in the immunogenicity . . . " Proc. Natl. Acad. Sci. U.S.A. 102(36):12915-20. Epub Aug. 23, 2005.
Hoffmann et al.,2000, "Unidirectional RNA polymerase I-polymerase II transcription system for the generation of influenza A virus . . . ", J.1 of Gen. Virology 81:2843-2847.
Hoffmann, Erich, Aufbau eines RNA-Polymerase 1-Vektorsystems zur gezielten Mutagenese von Influenza A Viren, Gieben 1997 (Doctoral Dissertation).
Hoffmann; 1997, "Generation of an RNA-Polymerase Vector Syst. for the Select. Mutagenesis . . . ," Inaugural Dissertation of Sch. of Nat. Sciences, Justus Liebig U. Gieben.
Huang et al., 1990, "Determination of Influenza virus proteins required for genome replication", J Virol. 64(11):5669-73.
Kaplan et al., 1985. "In vitro Synthesis of Infectious Poliovirus RNA", Proc. Natl. Acad. Sci. USA 82:8424-8428.
Katinger et al., "Attenuated Influenza Virus as a Vector for Mucosal Immunization against HIV-1", Vaccines, pp. 315-319, (1997).
Kato et al., 1996, "Initiation of Sendai Virus Multiplication from Transfected cDNA or RNA with Negative or PosKimura et al., 1993, An in vivo study of the replication origin in the influenza virus complementary RNA", J Biochem (Tokyo) 113:88-92.itive Sense, Genes to Cells 1:569-579.
Keitel, et al., "Live Cold-Adapted, Reassortant Influenza Vaccines (USA)," Textbook of Influenza, Chapter 28, pp. 373-390, (1998).
Kimura et al., 1992, "Transcription of a recombinant influenza virus RNA in cells that can express the influenza virus RNA polymerase . . . ", J Gen Virol. 73:1321-28.
Kimura et al., 1993, "An in vivo study of the replication origin in the influenza virus complementary RNA", J Biochem (Tokyo) 113:88-92.

Kobayashi et al., 1992, Reconstitution of influenza virus RNA polymerase from three subunits expressed using recombinant baculovirus system. Virus Res. 22:235-45.
Konarska et al., 1990, "Structure of RNAs replicated by the DNA-dependent T7 RNA polymerase", Cell. 63(3):609-18.
Krystal et al., 1986, "Expression of the Three Influenza Virus Polymerase Proteins in a Single Cell Allows Growth . . . ", Proc. Natl. Acad. Sci. USA 83:2709-2713.
Kunkel, 1985, "Rapid and Efficient Site-Specific Mutagenesis without Phenotypic Selection", Proc. Natl. Acad. Sci. USA 82:468-492.
Lamb et al., 1996, Fundamental Virology 3.sup.rd ed. Chapters 20 and 21.
Lawson et al., 1995, "Recombinant vesicular stomatitis viruses from DNA", Proc Natl Acad Sci U S A.92:4477-81.
Levis et al., 1986, "Deletion Mapping of Sindbis Virus DI RNAs Derived from cDNAs Defines the Sequences Essential for Replication and Packaging", Cell 44:137-145.
Li et al., 1999, "Recombinant influenza A virus vaccines for the pathogenic human A/Hong Kong/97 (H5N1) viruses," J. of Infectious Diseases, 179:1132-8.
Luytjes et al., 1989, "Amplification, Expression, and Packaging of a Foreign Gene by Influenza Virus", Cell 59:1107-1113.
Maassab et al., "Evaluation of a Cold-Recombinant Influenza Virus Vaccine in Ferrets", J. of Infectious Diseases, 146:780-790; (1982).
Maassab et al., "The Development of Live Attenuated Cold-adapted Influenza Virus Vaccine for Humans", Reviews in Medical Virology, 1999, vol. 9, pp. 237-245.
Maassab, "Adaptation and growth characteristics of influenza virus at 25 degrees C", Nature, 213:612-614 (1967).
Martin et al., 1998, "Studies of the Binding Properties of Influenza Hemagglutinin Receptor-Site Mutants", Virology 241:101-111.
Mena et al., 1994, "Synthesis of biologically active influenza virus core proteins using a vaccinia virus-T7 RNA polymerase expression system", J Gen Virol. 75:2109-14.
Mena et al., 1996, "Rescue of a Synthetic Chloramphenicol Acetyltransferase RNA into Influenza Virus-Like Particles Obtained fr. Recombinant Plasmids", J. Virol. 70: 5016-5024.
Merten et al., "Production of influenza virus in Cell Cultures for Vaccine Preparation", Novel Strategies in Design and Production of Vaccines, pp. 141-151; (1996).
Moyer et al., 1991, "Assembly and transcription of synthetic vesicular stomatitis virus nucleocapsids", J Virol. 65(5):2170-88.
Murphy & Coelingh, "Principles Underlying the Development and Use of Live Attenuated Cold-Adapted Influenza A and B Virus Vaccines", Viral Immunol, 15:295-323; (2002).
Muster et al., 1991, "An influenza A virus containing influenza B virus 5' and 3' noncoding regions on the neuraminidase gene . . . :", Proc Natl Acad Sci USA 88:5177-81.
Naito and Ishihama, 1976, "Function and Structure of RNA Polymerase from Vesicular Stomatitis Virus", J. Biol. Chem. 251:4307-4314.
Nakajima et al., 2003, "Restriction of Amino Acid Change in Influenza A Virus H3HA: Comparison of Amino Acid Changes Observed . . . ", J. of Virology 77(18):10088-10098.
Nara et al., 1987, "Simple, Rapid, Quantitative, Syncytium-Forming Micorassay for the Detection of Human Immunodeficiency . . . ", AIDS Res. Hum. Retroviruses 3:283-302.
Nemeroff et al., 1998, "Influenza Virus NS1 Protein Interacts with the Cellular 30 kDa Subunit of CPSF and Inhibits 3' End Formation . . . ", Mol. Cell 1:991-1000.
Neumann et al., "Reverse Genetics for the Control of Avian Influenza", Avian Diseases, 2003, vol. 47, pp. 882-887.
Neumann et al., 1994, "RNA Polymerase I-Mediated Expression of Influenza Viral RNA Molecules", Virol. 202:477-479.
Neumann et al.. 1999, "Generation of influenza A viruses entirely from cloned cDNAs", PNAS 96(16):9345-9350.
Neumann, et al., "Genetic Engineering of Influenza and Other Negative-Strand RNA Viruses Containing Segmented Genomes," Advances in Virus Research, 1999; 53: 265-300.
Nichol et al. 1999, "Effectiveness of live, attenuated intranasal influenza virus vaccine in healthy, working adults: a randomized controlled trial", JAMA 282:137-44.

Palese et al., 1996, "Negative-Strand RNA Viruses: Genetic Engineering and Applications", Proc. Natl. Acad. Sci. USA 93,11354-11358.

Park et al., 1991, "Rescue of a Foreign Gene by Sendai Virus", Proc. Natl. Acad. Sci. USA 88:5537-5541.

Parkin et al., "Temperature Sensitive Mutants of Influenza A Virus Generated by Reverse Genetics . . . ", Virus Res., 46:31-44; (1996).

Parkin N. et al., "Genetically Engineered Live Attenuated Influenza A Virus Vaccine Candidates", J. Virol., pp. 2772-2778; (1997).

Pattnaik et al., 1991, "Cells that express all five proteins of vesicular stomatitis virus from cloned cDNAs support replication . . . " Proc Natl Acad Sci USA 88:1379-83.

Peeters et al., 1999, "Rescue of Newcastle Disease Virus from Cloned cDNA: Evidence that Cleavability of the Fusion Protein . . . ", J. Virol. 73:5001-5009.

Pekosz et al., 1999, "Reverse genetics of negative-strand RNA viruses: closing the circle", Proc Natl Acad Sci USA. 96(16):8804-16.

Percy et al., 1994, "Expression of a foreign protein by influenza A virus", J Virol 68(7):4486-92.

Perez, Daniel R. et al., 1998 "The Matrix 1 Protein of Influenza A Virus Inhibits The Transcriptase Activity of a Model . . . ", Article No. VY989318, Virology, 249:52-61.

Pleschka et al., 1996, "A Plasmid-Based Reverse Genetics System for Influenza A Virus", J. Virol. 70:4188-4192.

Qiu et. al., 1994, "The influenza virus NS1 protein is a poly(A)-binding protein that inhibits nuclear export of mRNAs containing poly(A)", J Virol. 68(4):2425-32.

Qui et.al., 1995. "The influenza virus NS1 protein binds to a specific region in human U6 snRNA and inhibits U6-U2 and U6-U4 snRNA . . . ", RNA Society 1:304-16.

Racaniello et al., 1981. "Cloned Poliovirus Complementary DNA is Infectious in Mammalian Cells", Science 214:916-919.

Radecke et al., "Reverse Genetics Meets the Nonsegmented Negative-Strand RNA Viruses", Medical Virology, vol. 7: 49-63 (1997).

Radecke et al., 1995, "Rescue of measles viruses from cloned DNA", EMBO J. 14(23):5773-84.

Roberts and Rose, 1998, "Recovery of Negative-Strand RNA Viruses from Plasmid DNAs: a Positive Approach Revitalizes a Negative Field", Virol. 247:1-6.

Rose 1996, "Positive Strands to the Rescue Again: A Segmented Negative-Strand RNA Virus Derived from Cloned . . . ",PNAS USA 94:14998-15000.

Schickli et al., 2001, "Plasmid-only rescue of influenza A virus vaccine candidates", Philos Trans Society of London Ser B 356:1965-1973.

Schlesinger, 1995. "RNA viruses as vectors for the expression of heterologous proteins", Mol Biotechnol. 3:155-65.

Schnell et al., 1994, "Infectious Rabies Viruses from Cloned cDNA", EMBO J. 13:4195-4203.

Scholtissek, et al., "The Nucleoprotein as a Possible Major Factor in Determining Host Specificity of Influenza H3N2 Viruses," Virology, 1985; 147:287-294.

Seong et al., 1992, "A new method for reconstituting influenza polymerase and RNA in vitro: a study of the promoter elements for cRNA . . . ", Virology 186:247-60.

Shortridge et al., 1998, "Characterization of avian H5N1 influenza viruses . . . ", Virology 252(2):331-42.

Sidhu et al., 1995, "Rescue of synthetic measles virus minireplicons: measles genomic termini direct efficient expression . . . ", Virology. 208(2):800-07.

Snyder et al., "Four Viral Genes Independently Contribute to Attenuation of Live Influenza A/Ann Arbor/6/60 (H2N2) Cold-Adapted . . . ", J. Virol., 62:488-95; (1988).

Suarez et al., "Comparisons of Highly Virulent H5N1 Influenza A Viruses Isolated from Humans and Chickens from Hong Kong", Journal of Virology, vol. 72, No. 8 (1998).

Subbarao et al., "The Attenuation Phenotype Conferred by the M Gene of the Influenza A/Ann Arbor/6/60 Cold-Adapted Virus (H2N2) on the . . . " Virus Res., 25:37-50; (1992).

Subbarao et al., 1995, "Sequential addition of temperature-sensitive missense mutations into the PB2 gene of influenza A . . . ", J. of Virology 69(10):5969-5977.

Subbarao, Kanta et al., 2003, "Evaluation of a Genetically Modified Reassortant H5N1 Influenza A Virus Vaccine Candidate . . . " Virology 305:192-200.

Suguitan et al., 2006, "Live, attenuated influenza A H5N1 candidate vaccines . . . ", PLoS Med. Sep. 2006;3(9):e360.

Szewczyk et al., 1988, "Purification, Thioredoxin Renaturation, and Reconstituted Activity of the Three Subunits of the Influenza . . . ", Proc. Natl. Acad. Sci. USA 85:7907-7911.

Taylor et al., 1990, "Newcastle Disease Virus Fusion Protein Expressed in a Fowlpox Virus Recombinant Confers Protection in Chickens", J. Virol. 64:1441-1450.

US 2005-0287172 A1 Final Rejection mailed Jun. 1, 2007.

US 2005-0287172 A1 HA Sequence Search Results mailed Jun. 1, 2007.

US 2005-0287172 A1 NA Sequence Search Results mailed Jun. 1, 2007.

Ward et al., 1988, "Direct Measurement of the Poliovirus RNA Polymerase Error Frequency in Vitro", J. Virol. 62:558-562.

Wareing, J.M., et al, 2001, "Immunogenic and Isotype-Specific Responses to Russian and US Cold-Adapted Influenza A Vaccine Donor . . . ", J. of Medical Virology 65:171-177.

Webby et al., 2004, "Responsiveness to a pandemic alert: use of reverse genetics for rapid development of influenza vaccines", Lancet 363:1099-1103.

Whelan et al., 1995, "Efficient recovery of infectious vesicular stomatitis virus entirely from cDNA clones", Proc.Natl.Acad.Sci. USA 92:8388-8392.

Xu et al., 1995 #AAB06964 (abstract only).

Xu et al., 1996, "Genetic Variation in Neuraminidase Genes of Influenza A (H3N2) Viruses", Virology 224:175-183.

Xu, Xiyan, et al., 1999 "Genetic Characterization of the Pathogenic Influenza A /Goose/Guangdong/1/96 (H5N1) Virus: . . . ", Article ID viro. 1999.9820. Virology 261:15-19.

Yamanaka et al., 1991, "In vivo analysis of the promoter structure of the influenza virus RNA genome using a transfection system . . . ," Proc Natl Acad Sci USA 88: 5369-5373.

Yu et al., 1995, "Functional cDNA clones of the human respiratory syncytial (RS) virus N, P, and L proteins support replication . . . ", J Virol. 69(4):2412-19.

Yusoff et al., 1987, "Nucleotide Sequence Analysis of the L Gene of Newcastle Disease Virus: Homologies with Sendi and Vesicular Stomatitis.", Nucleic Acids Res. 15:3961-76.

Zaghouani et al., 1991, "Induction of antibodies to the envelope protein of the human immunodeficiency virus by immunization . . . ", Proc. Natl. Acad Sci. USA 88:5645-5649.

Zaghouani et al., 1992, "Cells Expressing an H Chain to Gene Carrying a Viral T Cell Epitope Are Lysed by Specific Cytolytic T Cells", J. Immunol. 148:3604-3609.

Zhang and Air, 1994, "Expression of Functional Influenza Virus A Polymerase Proteins and Template from Cloned cDNAs . . . ", Biochem. & Biophys. Res. Commun. 200:95-101.

Zhang et al., "Persistence of four related human munodeficiency virus subtypes during the course of zidovudine therapy . . . ", J. Virol. 1994 68: 425-432.

Zhou et al., 1999, "Rapid evolution of H5N1 influenza viruses . . . ," J. Virol. 73(4):3366-74.

Zhou, Yan, et al., "Membrane-Anchored Incorporation of a Foreign Protein in Recombinant Influenza Virions", Article No. VY989169, Virology, 1998, vol. 246, pp. 83-94.

Zobel et al., 1993, "RNA polymerase I catalysed transcription of insert viral cDNA", Nucleic Acids Res. 21(16):3607-14.

* cited by examiner

Figure 1

VN/1203/2004 wildtype HA:

CCT CAA AGA GAG AGA AGA AAA AAG AGA → GGA TTA TTT
Pro Gln Arg Glu Arg Arg Lys Lys Arg   Gly Leu Phe

Modified HA:

CCT CAA AGA GAG <u>ACT</u>              <u>CGA</u> → GGA TTA TTT
Pro Gln Arg Glu <u>Thr</u>              <u>Arg</u>   Gly Leu Phe

→ Site of cleavage of into HA1 and HA2 domains.

Residues that were mutagenized are underlined.

Figure 2

Virus isolation from swabs

| Virus | Mortality (dead/total) | Oropharyngeal | | Cloacal | | Antibody detected/ total |
|---|---|---|---|---|---|---|
| | | # shedding/ total | Mean log$_{10}$ titer (EID$_{50}$) | # shedding/ total | Mean log$_{10}$ titer (EID$_{50}$) | |
| 1997, 2003 and 2004 H5N1 wt | 8/8 | 8/8 | >6.3 | 8/8 | >4.5 | NA |
| 1997, 2003 and 2004 H5N1 ca | 0/8 | 0/8 | <0.9 | 0/8 | <0.9 | 0/8 |

*Chickens were inoculated intranasally with $10^6$ TCID$_{50}$ of virus.*

Figure 3

| | $LD_{50}$ in mice |
|---|---|
| A/AA/6/60 ca | $>10^7$ TCID$_{50}$ |
| A/HK/491/97 | $10^2$ TCID$_{50}$ |
| 1997 H5N1/AA ca | $>10^7$ TCID$_{50}$ |
| A/HK/213/2003 | $10^6$ TCID$_{50}$ |
| 2003 H5N1/AA ca | $>10^7$ TCID$_{50}$ |
| A/Vietnam/1203/2004 | $10^{0.4}$ TCID$_{50}$ |
| 2004 H5N1/AA ca | $>10^7$ TCID$_{50}$ |

Figure 4

| Tissue | Virus | Average fold difference in titer over 3 days |
|---|---|---|
| LUNGS | A/AA/6/60 | 93 |
| | 1997 H5N1 | 501 |
| | 2003 H5N1 | 12 |
| | 2004 H5N1 | 430 |
| NASAL TURBINATES | A/AA/6/60 | 32 |
| | 1997 H5N1 | 185 |
| | 2003 H5N1 | none |
| | 2004 H5N1 | 100 |

$10^6$ $TCID_{50}$ of virus was administered intranasally and tissues were harvested on days 2, 3 or 4 post-infection. Virus titers are expressed as $\log_{10}$ $TCID_{50}/g$ of tissue.

Figure 6

| Immunizing virus | Geometric mean serum HAI Ab titers against indicated virus | | |
|---|---|---|---|
| | 1997 wt | 2003 wt | 2004 wt |
| 2003 ca | 20 | 213.6 | 20 |
| 2003 wt | 20 | 394 | 20 |

An undetectable titer is assigned a value of 20

Figure 7

| Immunizing virus | Geometric mean serum neutralizing Ab titers against indicated virus | | |
|---|---|---|---|
| | 1997 wt | 2003 wt | 2004 wt |
| 2003 ca | 10 | 59.2 | 10 |
| 2003 wt | 10 | 93.3 | 10 |

An undetectable titer is assigned a value of 10

| Immunization | Mean reduction in titer in lungs following | | | | |
| --- | --- | --- | --- | --- | --- |
| | Homologous challenge | Heterologous H5N1 challenge | | | |
| | | 1997 wt | 2003 wt | 2004 wt | |
| 1997 ca | 2.5 | NA | 3.0 | 0.7 | |
| 2003 ca | >5.8 | 2.3 | NA | 2.9 | |
| 2004 ca | 2.0 | 1.4 | >5.7 | NA | |

Figure 10

| Immunization | Mean reduction in titer in NT following | | | | |
|---|---|---|---|---|---|
| | Homologous challenge | Heterologous H5N1 challenge | | | |
| | | 1997 wt | 2003 wt | 2004 wt | |
| 1997 ca | 4.3 | NA | >1.2 | 2.6 | |
| 2003 ca | >1.2 | 3.7 | NA | >3.3 | |
| 2004 ca | 1.6 | 4.2 | >3.5 | NA | | ary application of application
INFLUENZA HEMAGGLUTININ AND NEURAMINIDASE VARIANTS

CROSS REFERENCE TO RELATED APPLICATIONS

This application is a divisional application of application Ser. No. 11/133,346 filed May 20, 2005, allowed, which claims the benefit under 35 U.S.C. §119 (e) of U.S. Provisional Application Nos. 60/574,553 filed May 25, 2004 and 60/657,554, filed Feb. 28, 2005, the disclosures of each of which are incorporated herein in their entirety for all purposes.

BACKGROUND OF THE INVENTION

Vaccines against various and evolving strains of influenza are important from a community health stand point, as well as commercially, since each year numerous individuals are infected with different strains and types of influenza virus. Infants, the elderly, those without adequate health care and immuno-compromised persons are at special risk of death from such infections. Compounding the problem of influenza infections is that novel influenza strains evolve readily and can spread amongst various species, thereby necessitating the continuous production of new vaccines.

Numerous vaccines capable of producing a protective immune response specific for such different and influenza viruses/virus strains have been produced for over 50 years and include whole virus vaccines, split virus vaccines, surface antigen vaccines and live attenuated virus vaccines. However, while appropriate formulations of any of these vaccine types are capable of producing a systemic immune response, live attenuated virus vaccines have the advantage of also being able to stimulate local mucosal immunity in the respiratory tract. Considerable work in the production of influenza viruses, and fragments thereof, for production of vaccines has been done by the present inventors and co-workers; see, e.g., U.S. Application Nos. 60/420,708, filed Oct. 23, 2002; 60/574,117, filed May 24, 2004; 10/423,828, filed Apr. 25, 2003; 60/578,962, filed Jun. 12, 2004; and 10/870,690 filed Jun. 16, 2004, the disclosure of which is incorporated by reference herein.

Because of the continual emergence (or re-emergence) of different influenza strains, new influenza vaccines are continually desired. Such vaccines typically are created using antigenic moieties of the newly emergent virus strains, thus, polypeptides and polynucleotides of novel, newly emergent, or newly re-emergent virus strains (especially sequences of antigenic genes) are highly desirable.

The present invention provides new and/or newly isolated influenza hemagglutinin and neuraminidase variants that are capable of use in production of numerous types of vaccines as well as in research, diagnostics, etc. Numerous other benefits will become apparent upon review of the following.

SUMMARY OF THE INVENTION

In some aspects herein, the invention comprises an isolated or recombinant polypeptide that is selected from: the polypeptides encoded by any one of the sequences of SEQ ID NO:1 through SEQ ID NO:10, any one of the polypeptides encoded by SEQ ID NO:1 through SEQ ID NO:10; any one of the polypeptides of SEQ ID NO:11 through SEQ ID NO:20; only the open reading frame of the polypeptides of SEQ ID NO:11 through SEQ ID NO:20; alternative (e.g., the mature form without the signal peptide, or without the 5' and 3' sequences outside of the open reading frame, or the sequences as expressed on the surface of a virus (e.g., influenza)) forms of the polypeptide of SEQ ID NO:11-20; any polypeptide that is encoded by a polynucleotide sequence which hybridizes under highly stringent conditions over substantially the entire length of a polynucleotide sequence of SEQ ID NO:1 through SEQ ID NO:10; any polypeptide that is encoded by a polynucleotide sequence which hybridizes under highly stringent conditions to a polynucleotide sequence of SEQ ID NO:1 through SEQ ID NO:10; and, a fragment of any of the above wherein the sequence comprises a hemagglutinin or neuraminidase polypeptide, or a fragment of a hemagglutinin or neuraminidase polypeptide, preferably where the fragments generate an antibody that specifically binds a full length polypeptide of the invention. In various embodiments, the isolated or recombinant polypeptides of the invention are substantially identical to about 300 contiguous amino acid residues of any of the above polypeptides. In yet other embodiments, the invention comprises isolated or recombinant polypeptides, that comprise an amino acid sequence that is substantially identical over at least about 350 amino acids; over at least about 400 amino acids; over at least about 450 amino acids; over at least about 500 amino acids; over at least about 502 amino acids; over at least about 550 amino acids; over at least about 559 amino acids; over at least about 565 amino acids; or over at least about 566 amino acids contiguous of any of the above polypeptides. In some embodiments, the polypeptide sequence (e.g., as listed in the sequence listing herein) comprises less than 565, 559, etc. amino acids. In such embodiments, the shorter listed polypeptides optionally comprise less than 565, 559, etc. amino acids. In yet other embodiments, the polypeptides of the invention optionally comprise fusion proteins, proteins with a leader sequence, a precursor polypeptide, proteins with a secretion signal or a localization signal, or proteins with an epitope tag, an E-tag, or a His epitope tag. In still other embodiments, the invention comprises a polypeptide comprising a sequence having at least 85%, at least 90%, at least 93%, at least 95%, at least 98%, at least 98.5%, at least 99%, at least 99.2%, at least 99.4%, at least 99.6%, at least 99.8%, or at least 99.9% sequence identity to at least one polypeptide listed above. The sequences of the invention are also shown in Appendix 1 and in the sequence listings herein. The hemagglutinin sequences of the invention can comprise both those sequences with unmodified and modified polybasic cleavage sites (thereby allowing growth of the viruses in eggs). The hemagglutinin polypeptide sequences of SEQ ID NOS:11-20 comprise the endogenous amino terminal signal peptide sequences, however, the hemagglutinin polypeptide sequences of the invention also include the mature (amino terminal signal peptide cleaved) form of the hemagglutinin polypeptides. The cleavage sites of any hemagglutinin polypeptide sequence of any influenza strain can be routinely measured or predicted using any number of methods in the art.

In other aspects, the invention comprises a composition with one or more polypeptide listed above, or fragments thereof. The invention also includes polypeptides that are specifically bound by a polyclonal antisera raised against at least 1 antigen that comprises at least one amino acid sequence described above, or a fragment thereof. Such antibodies specific for the polypeptides described above are also features of the invention. The polypeptides of the invention are optionally immunogenic.

The invention also encompasses immunogenic compositions comprising an immunologically effective amount of one or more of any of the polypeptides described above as well as methods for stimulating the immune system of an individual to produce a protective immune response against influenza virus by administering to the individual an immunologically effective amount of any of the above polypeptides in a physiologically acceptable carrier.

Additionally, the invention includes recombinant influenza virus that comprises one or more of the polypeptides or polynucleotides above, in addition to immunogenic compositions comprising an immunologically effective amount of such recombinant influenza virus. Methods for stimulating the immune system of an individual to produce a protective immune response against influenza virus, through administering an immunologically effective amount of such recombinant influenza virus in a physiologically acceptable carrier are also part of the invention.

In other aspects, the invention comprises an isolated or recombinant nucleic acid that is selected from: any one of the polynucleotide sequences SEQ ID NO:1 through SEQ ID NO:10 (or complementary sequences thereof), any one of the polynucleotide sequences encoding a polypeptide of SEQ ID NO:11 through SEQ ID NO:20 (or complementary polynucleotide sequences thereof), a polynucleotide sequence which hybridizes under highly stringent conditions over substantially the entire length of any of the above polynucleotide sequences, and a polynucleotide sequence comprising all or a fragment of any of such polynucleotide sequences wherein the sequence preferably encodes a hemagglutinin or neuraminidase polypeptide or a fragment of a hemagglutinin or neuraminidase polypeptide. The invention also includes an isolated or recombinant nucleic acid that encodes an amino acid sequence which is substantially identical over at least about 300 amino acids of any of the above nucleic acids, or over at least about 350 amino acids; over at least about 400 amino acids; over at least about 450 amino acids; over at least about 500 amino acids; over at least about 502 amino acids; over at least about 550 amino acids; over at least about 559 amino acids; over at least about 565 amino acids; or over at least about 566 amino acids of any of the above nucleic acids. Again, in situations wherein the amino acid is less than, e.g., 566, 565, 559, etc. in length (e.g., see, Sequence Listing) then it should be understood that the length is optionally less than 566, 565, 559, etc. The invention also includes any of the above nucleic acids that comprise a hemagglutinin or neuraminidase polypeptide, or one or more fragments of one or more hemagglutinin or neuraminidase polypeptide. Other aspects of the invention include isolated or recombinant nucleic acids that encode a polypeptide (optionally a hemagglutinin or neuraminidase polypeptide) whose sequence has at least 98% identity, at least 98.5% identity, at least 99% identity, at least 99.2% identity, at least 99.4% identity, at least 99.6% identity, at least 99.8% identity, or at least 99.9% identity to at least one of the above described polynucleotides. The invention also includes isolated or recombinant nucleic acids encoding a polypeptide of hemagglutinin or neuraminidase produced by mutating or recombining one or more above described polynucleotide sequences. The polynucleotide sequences of the invention can optionally comprise one or more of, e.g., a leader sequence, a precursor sequence, or an epitope tag sequence or the like, and can optionally encode a fusion protein (e.g., with one or more additional nucleic acid sequences).

In yet other embodiments, the invention comprises a composition of matter having two or more above described nucleic acids (e.g., a library comprising at least about 2, 5, 10, 50 or more nucleic acids). Such compositions can optionally be produced by cleaving one or more above described nucleic acid (e.g., mechanically, chemically, enzymatically with a restriction endonuclease/RNAse/DNAse, etc.). Other compositions of the invention include, e.g., compositions produced by incubating one or more above described nucleic acid in the presence of deoxyribonucleotide triphosphates and a thermostable nucleic acid polymerase.

The invention also encompasses cells comprising at least one of the above described nucleic acids, or a cleaved or amplified fragment or product thereof. Such cells can optionally express a polypeptide encoded by such nucleic acid. Other embodiments of the invention include vectors (e.g., plasmids, cosmids, phage, viruses, virus fragments, etc.) comprising any of above described nucleic acids. Such vectors can optionally comprise an expression vector. Preferred expression vectors of the invention include, but are not limited to, vectors comprising pol I promoter and terminator sequences or vectors using both the pol I and pol II promoters "the polI/polII promoter system" (e.g., Zobel et al., Nucl. Acids Res. 1993, 21:3607; US20020164770; Neumann et al., Proc. Natl. Acad. Sci. USA 1999, 96:9345; Fodor et al., J. Virol. 1999, 73:9679; and US20030035814). Cells transduced by such vectors are also within the current invention.

In some embodiments, the invention encompasses a virus (e.g., an influenza virus) comprising one or more above described nucleic acids (e.g., encoding hemagglutinin and/or neuraminidase), or one or more fragments thereof. Immunogenic compositions comprising such virus are also part of the current invention. Such viruses can comprises a reassortment virus such as a 6:2 reassortment virus (e.g., comprising 6 gene encoding regions from one or more donor virus and 2 gene encoding regions from one or more above described nucleotide sequence (or one or more fragment thereof) which can optionally comprise hemagglutinin and/or neuraminidase). Reassortment viruses (optionally live viruses) of the invention can include donor viruses that are one or more of, e.g., cold-sensitive, cold-adapted, or an attenuated. For example, reassortment viruses can comprise e.g., A/Ann Arbor/6/60, PR8, etc. Reassortment viruses of the invention may alternatively exclude A/Ann Arbor/6/60. One preferred embodiment of the invention is a reassortant influenza virus, wherein the virus is a 6:2 reassortment influenza virus and comprises 6 gene encoding regions from A/Ann Arbor/6/60 and 2 gene encoding regions that encode a polypeptide selected from the group consisting of: the polypeptides of SEQ ID NOS:11-20. In an alternative embodiment, a reassortant influenza virus of the invention includes a 6:2 reassortment influenza virus, wherein said virus comprises 6 gene encoding regions from one or more donor viruses other than A/Ann Arbor/6/60 and 2 gene encoding regions that encode a polypeptide selected from the group consisting of: the polypeptides of SEQ ID NOS:11-20. In another alternative embodiment, a reassortant influenza virus of the invention includes a 6:2 reassortment influenza virus, wherein said virus comprises 6 gene encoding regions from one or more donor viruses other than A/Ann Arbor/6/60 and 2 gene encoding regions, wherein the 2 gene encoding regions are HA or NA polypeptides from any pandemic influenza strain. Methods of producing recombinant influenza virus through culturing a host cell harboring an influenza virus in a suitable culture medium under conditions permitting expression of nucleic acid and, isolating the recombinant influenza virus from one or more of the host cell or the medium are also part of the invention.

In other embodiments herein, the invention comprises immunogenic compositions having an immunologically effective amount of any of the above described recombinant influenza virus. Other embodiments include methods for stimulating the immune system of an individual to produce a protective immune response against influenza virus by administering to the individual an immunologically effective amount of any of the recombinant influenza virus described above (optionally in a physiologically effective carrier).

Other aspects of the invention include methods of producing an isolated or recombinant polypeptide by culturing any host cell above, in a suitable culture medium under conditions permitting expression of nucleic acid and, isolating the polypeptide from one or more of the host cells or the medium in which is the cells are grown.

Immunogenic compositions are also features of the invention. For example, immunogenic compositions comprising one or more of any of the polypeptides and/or nucleic acids described above and, optionally, an excipient such as a pharmaceutically acceptable excipient or one or more pharmaceutically acceptable administration component. Immunogenic compositions of the invention can also comprise any one or more above described virus as well (e.g., along with one or more pharmaceutically acceptable administration component).

Methods of producing immunogenic responses in a subject through administration of an effective amount of any of the above viruses (or immunogenic compositions) to a subject are also within the current invention. Additionally, methods of prophylactic or therapeutic treatment of a viral infection (e.g., viral influenza) in a subject through administration of any one or more above described virus (or immunogenic compositions) in an amount effective to produce an immunogenic response against the viral infection are also part of the current invention. Subjects for such treatment can include mammals (e.g., humans). Such methods can also comprise in vivo administration to the subject as well as in vitro or ex vivo administration to one or more cells of the subject. Additionally, such methods can also comprise administration of a composition of the virus and a pharmaceutically acceptable excipient that are administered to the subject in an amount effect to prophylactically or therapeutically treat the viral infection.

In other aspects the invention includes compositions of matter comprising nucleic acid sequences encoding hemagglutinin and/or neuraminidase polypeptides of one or more pandemic influenza strain and nucleic acid sequences encoding one or more polypeptide of A/Ann Arbor/6/60. Additionally, the invention includes compositions of matter comprising nucleic acid sequences encoding hemagglutinin and/or neuraminidase polypeptides of one or more pandemic influenza strain and nucleic acid sequences encoding one or more polypeptide of PR8 or A/Ann Arbor/6/60. Such sequences can include those listed in the Sequence Listing herein. Additionally, preferred embodiments of the invention include compositions of matter comprising sequences encoding hemagglutinin and/or neuraminidase of one or more pandemic influenza strain and nucleic acid sequences encoding a selected backbone strain in a 6:2 reassortment. Such compositions preferably include sequences encoding the hemagglutinin and neuraminidase selected from the Sequence Listing herein and a backbone strain, wherein the backbone strain is PR8 or A/Ann Arbor/6/60. The invention also includes such compositions as described above wherein the hemagglutinin comprises a modified polybasic cleavage site. The invention also includes live attenuated influenza vaccine comprising such above compositions.

These and other objects and features of the invention will become more fully apparent when the following detailed description is read in conjunction with the accompanying figures and appendix.

BRIEF DESCRIPTION OF THE DRAWINGS

FIG. 1: Shows modifications engineered into the HA gene of VN/1203/2004 to remove the polybasic cleavage site. VN/1203/2004 wild type HA polybasic cleavage site nucleotide and amino acid sequences are shown as SEQ ID NO: 21 and 22, respectively. Modified HA cleavage site nucleotide and amino acid sequences are shown as nucleotides 1037-1063 of SEQ ID NO: 1 and residues 337-345 of SEQ ID NO: 11, respectively.

FIG. 2: Displays results showing that intranasally administered H5N1 ca reassortant viruses do not replicate in chickens.

FIG. 3: Illustrates that the H5N1/AA ca vaccine candidates are not lethal to mice.

FIG. 4: Illustrates that the 1997 and 2004 H5N1 ca reassortant viruses are restricted in replication in mice.

FIG. 6: Shows the serum HAI Ab titers elicited in mice following a single i.n. dose of vaccine.

FIG. 7: Shows serum neutralizing Ab titers elicited in mice following a single i.n. dose of vaccine.

FIG. 8: Illustrates that H5N1 ca reassortant viruses protect mice from lethal challenges with 50, 500 or 5000 $LD_{50}$ of wild-type H5N1 viruses.

FIG. 9: Illustrates the efficacy of protection from pulmonary replication of homologous and heterologous H5N1 challenge viruses in mice.

FIG. 10: Illustrates the efficacy of protection from replication of homologous and heterologous H5N1 challenge viruses in the upper respiratory tract of mice.

DETAILED DESCRIPTION

Figure 5:
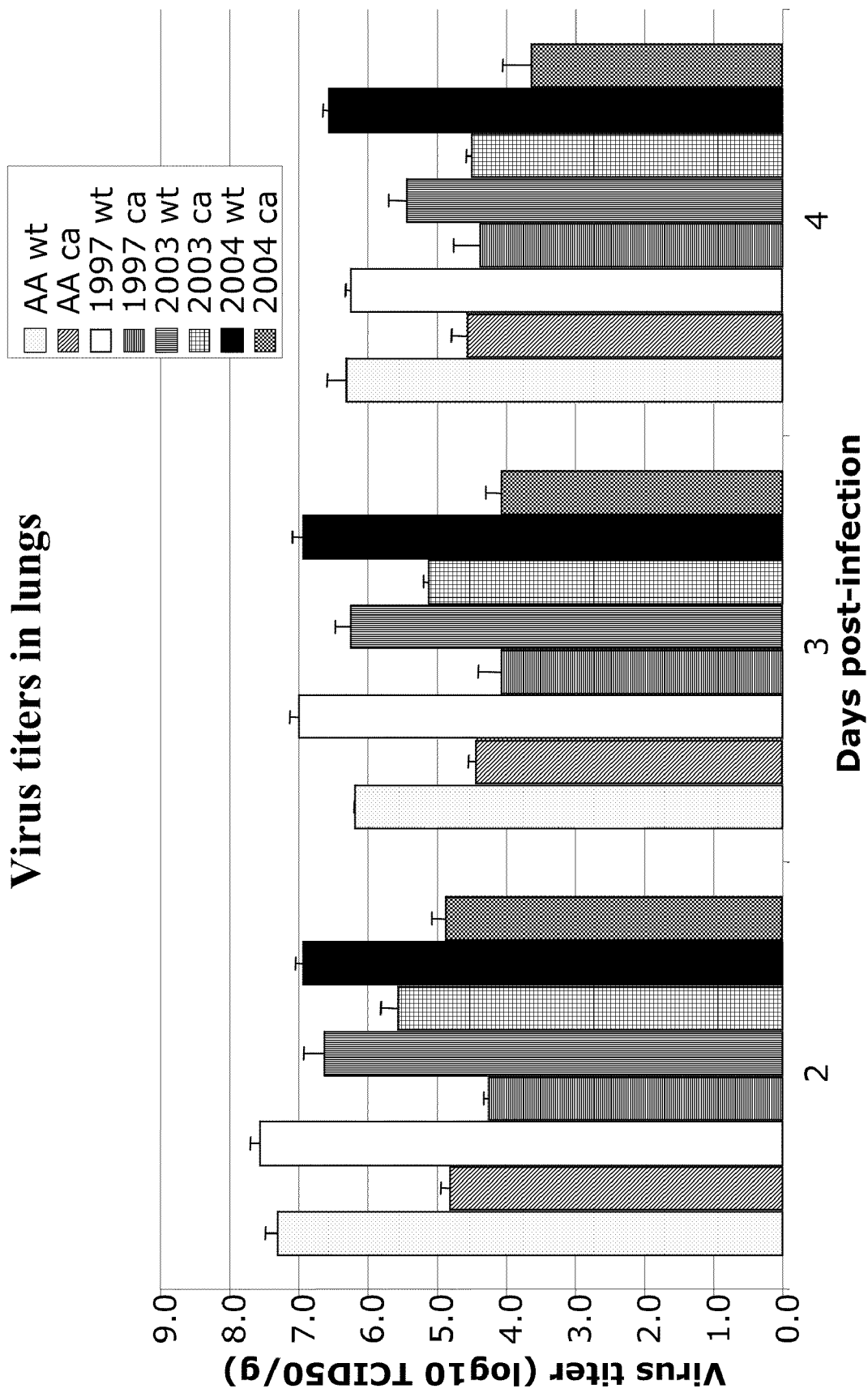
FIG. 5: Illustrates that the reassortant H5N1/AA ca influenza viruses are restricted in replication in lungs of mice.

The present invention includes polypeptide and polynucleotide sequences of influenza hemagglutinin and neuraminidase as well as vectors, compositions and the like comprising such sequences and methods of their use. Additional features of the invention are described in more detail herein.

Definitions

Unless defined otherwise, all technical and scientific terms used herein have the same meaning as commonly understood by one of ordinary skill in the art to which the invention pertains. The following definitions supplement those in the art and are directed to the current application and are not necessarily to be imputed to any related or unrelated case, e.g., to any commonly owned patent or application. Although any methods and materials similar or equivalent to those described herein can be used in the practice for testing of the present invention, the preferred materials and methods are described herein. Accordingly, the terminology used herein is for the purpose of describing particular embodiments only, and is not intended to be limiting.

As used in this specification and the appended claims, the singular forms "a," "an" and "the" include plural referents unless the context clearly dictates otherwise. Thus, for example, reference to "a virus" includes a plurality of viruses; reference to a "host cell" includes mixtures of host cells, and the like.

An "amino acid sequence" is a polymer of amino acid residues (a protein, polypeptide, etc.) or a character string representing an amino acid polymer, depending on context.

The terms "nucleic acid," "polynucleotide," "polynucleotide sequence" and "nucleic acid sequence" refer to single-stranded or double-stranded deoxyribonucleotide or ribonucleotide polymers, chimeras or analogues thereof, or a character string representing such, depending on context. As used herein, the term optionally includes polymers of analogs of naturally occurring nucleotides having the essential nature of natural nucleotides in that they hybridize to single-stranded nucleic acids in a manner similar to naturally occurring nucleotides (e.g., peptide nucleic acids). Unless otherwise indicated, a particular nucleic acid sequence of this invention optionally encompasses complementary sequences in addition to the sequence explicitly indicated. From any specified polynucleotide sequence, either the given nucleic acid or the complementary polynucleotide sequence (e.g., the complementary nucleic acid) can be determined.

The term "nucleic acid" or "polynucleotide" also encompasses any physical string of monomer units that can be corresponded to a string of nucleotides, including a polymer of nucleotides (e.g., a typical DNA or RNA polymer), PNAs, modified oligonucleotides (e.g., oligonucleotides comprising bases that are not typical to biological RNA or DNA in solution, such as 2'-O-methylated oligonucleotides), and the like. A nucleic acid can be e.g., single-stranded or double-stranded.

A "subsequence" is any portion of an entire sequence, up to and including the complete sequence. Typically, a subsequence comprises less than the full-length sequence. A "unique subsequence" is a subsequence that is not found in any previously determined influenza polynucleotide or polypeptide sequence The term "variant" with respect to a polypeptide refers to an amino acid sequence that is altered by one or more amino acids with respect to a reference sequence. The variant can have "conservative" changes, wherein a substituted amino acid has similar structural or chemical properties, e.g., replacement of leucine with isoleucine. Alternatively, a variant can have "nonconservative" changes, e.g., replacement of a glycine with a tryptophan. Analogous minor variation can also include amino acid deletion or insertion, or both. Guidance in determining which amino acid residues can be substituted, inserted, or deleted without eliminating biological or immunological activity can be found using computer programs well known in the art, for example, DNASTAR software. Examples of conservative substitutions are also described herein.

The term "gene" is used broadly to refer to any nucleic acid associated with a biological function. Thus, genes include coding sequences and/or the regulatory sequences required for their expression. The term "gene" applies to a specific genomic sequence, as well as to a cDNA or an mRNA encoded by that genomic sequence.

Genes also include non-expressed nucleic acid segments that, for example, form recognition sequences for other proteins. Non-expressed regulatory sequences include "promoters" and "enhancers," to which regulatory proteins such as transcription factors bind, resulting in transcription of adjacent or nearby sequences. A "tissue specific" promoter or enhancer is one that regulates transcription in a specific tissue type or cell type, or types.

"Expression of a gene" or "expression of a nucleic acid" means transcription of DNA into RNA (optionally including modification of the RNA, e.g., splicing), translation of RNA into a polypeptide (possibly including subsequent modification of the polypeptide, e.g., post-translational modification), or both transcription and translation, as indicated by the context.

An "open reading frame" or "ORF" is a possible translational reading frame of DNA or RNA (e.g., of a gene), which is capable of being translated into a polypeptide. That is, the reading frame is not interrupted by stop codons. However, it should be noted that the term ORF does not necessarily indicate that the polynucleotide is, in fact, translated into a polypeptide.

The term "vector" refers to the means by which a nucleic acid can be propagated and/or transferred between organisms, cells, or cellular components. Vectors include plasmids, viruses, bacteriophages, pro-viruses, phagemids, transposons, artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that is not autonomously replicating. In many, but not all, common embodiments, the vectors of the present invention are plasmids.

An "expression vector" is a vector, such as a plasmid that is capable of promoting expression, as well as replication of a nucleic acid incorporated therein. Typically, the nucleic acid to be expressed is "operably linked" to a promoter and/or enhancer, and is subject to transcription regulatory control by the promoter and/or enhancer.

A "bi-directional expression vector" is characterized by two alternative promoters oriented in the opposite direction relative to a nucleic acid situated between the two promoters, such that expression can be initiated in both orientations resulting in, e.g., transcription of both plus (+) or sense strand, and negative (−) or antisense strand RNAs.

A "polypeptide" is a polymer comprising two or more amino acid residues (e.g., a peptide or a protein). The polymer can optionally comprise modifications such as glycosylation or the like. The amino acid residues of the polypeptide can be natural or non-natural and can be unsubstituted, unmodified, substituted or modified.

In the context of the invention, the term "isolated" refers to a biological material, such as a virus, a nucleic acid or a protein, which is substantially free from components that normally accompany or interact with it in its naturally occurring environment. The isolated biological material optionally comprises additional material not found with the biological material in its natural environment, e.g., a cell or wild-type virus. For example, if the material is in its natural environment, such as a cell, the material can have been placed at a location in the cell (e.g., genome or genetic element) not native to such material found in that environment. For example, a naturally occurring nucleic acid (e.g., a coding sequence, a promoter, an enhancer, etc.) becomes isolated if it is introduced by non-naturally occurring means to a locus of the genome (e.g., a vector, such as a plasmid or virus vector, or amplicon) not native to that nucleic acid. Such nucleic acids are also referred to as "heterologous" nucleic acids. An isolated virus, for example, is in an environment (e.g., a cell culture system, or purified from cell culture) other than the native environment of wild-type virus (e.g., the nasopharynx of an infected individual).

The term "chimeric" or "chimera," when referring to a virus, indicates that the virus includes genetic and/or polypeptide components derived from more than one parental viral strain or source. Similarly, the term "chimeric" or "chimera," when referring to a viral protein, indicates that the protein includes polypeptide components (i.e., amino acid subsequences) derived from more than one parental viral strain or source.

The term "recombinant" indicates that the material (e.g., a nucleic acid or protein) has been artificially or synthetically (non-naturally) altered by human intervention. The alteration can be performed on the material within, or removed from, its natural environment or state. Specifically, e.g., an influenza virus is recombinant when it is produced by the expression of a recombinant nucleic acid. For example, a "recombinant nucleic acid" is one that is made by recombining nucleic acids, e.g., during cloning, DNA shuffling or other procedures, or by chemical or other mutagenesis; a "recombinant polypeptide" or "recombinant protein" is a polypeptide or protein which is produced by expression of a recombinant nucleic acid; and a "recombinant virus", e.g., a recombinant influenza virus, is produced by the expression of a recombinant nucleic acid.

The term "reassortant," when referring to a virus, indicates that the virus includes genetic and/or polypeptide components derived from more than one parental viral strain or source. For example, a 7:1 reassortant includes 7 viral genomic segments (or gene segments) derived from a first parental virus, and a single complementary viral genomic segment, e.g., encoding a hemagglutinin or neuraminidase of the invention. A 6:2 reassortant includes 6 genomic segments, most commonly the 6 internal genes from a first parental virus, and two complementary segments, e.g., hemagglutinin and neuraminidase, from a different parental virus.

The term "introduced" when referring to a heterologous or isolated nucleic acid refers to the incorporation of a nucleic acid into a eukaryotic or prokaryotic cell where the nucleic acid can be incorporated into the genome of the cell (e.g., chromosome, plasmid, plastid or mitochondrial DNA), converted into an autonomous replicon, or transiently expressed (e.g., transfected mRNA). The term includes such methods as "infection," "transfection," "transformation" and "transduction." In the context of the invention a variety of methods can be employed to introduce nucleic acids into cells, including electroporation, calcium phosphate precipitation, lipid mediated transfection (lipofection), etc.

The term "host cell" means a cell that contains a heterologous nucleic acid, such as a vector, and supports the replication and/or expression of the nucleic acid. Host cells can be prokaryotic cells such as E. coli, or eukaryotic cells such as yeast, insect, amphibian, avian or mammalian cells, including human cells. Exemplary host cells can include, e.g., Vero (African green monkey kidney) cells, BHK (baby hamster kidney) cells, primary chick kidney (PCK) cells, Madin-Darby Canine Kidney (MDCK) cells, Madin-Darby Bovine Kidney (MDBK) cells, 293 cells (e.g., 293T cells), and COS cells (e.g., COS1, COS7 cells), etc.

An "immunologically effective amount" of influenza virus is an amount sufficient to enhance an individual's (e.g., a human's) own immune response against a subsequent exposure to influenza virus. Levels of induced immunity can be monitored, e.g., by measuring amounts of neutralizing secretory and/or serum antibodies, e.g., by plaque neutralization, complement fixation, enzyme-linked immunosorbent, or microneutralization assay.

A "protective immune response" against influenza virus refers to an immune response exhibited by an individual (e.g., a human) that is protective against disease when the individual is subsequently exposed to and/or infected with such influenza virus. In some instances, the influenza virus (e.g., naturally circulating) can still cause infection, but it cannot cause a serious infection. Typically, the protective immune response results in detectable levels of host engendered serum and secretory antibodies that are capable of neutralizing virus of the same strain and/or subgroup (and possibly also of a different, non-vaccine strain and/or subgroup) in vitro and in vivo.

As used herein, an "antibody" is a protein comprising one or more polypeptides substantially or partially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. A typical immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively. Antibodies exist as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region thereby converting the $(Fab')_2$ dimer into a Fab' monomer. The Fab' monomer is essentially a Fab with part of the hinge region (see, Fundamental Immunology, W. E. Paul, ed., Raven Press, N.Y. (1999), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein, includes antibodies or fragments either produced by the modification of whole antibodies or synthesized de novo using recombinant DNA methodologies. Antibodies include, e.g., polyclonal antibodies, monoclonal antibodies, multiple or single chain antibodies, including single chain Fv (sFv or scFv) antibodies in which a variable heavy and a variable light chain are joined together (directly or through a peptide linker) to form a continuous polypeptide, and humanized or chimeric antibodies.

Influenza Virus

The polypeptides and polynucleotides of the invention, e.g., SEQ ID NO: 1-20, are variants of influenza HA and NA sequences. In general, influenza viruses are made up of an internal ribonucleoprotein core containing a segmented single-stranded RNA genome and an outer lipoprotein envelope lined by a matrix protein. The genome of influenza viruses is composed of eight segments of linear (−) strand ribonucleic acid (RNA), encoding the immunogenic hemagglutinin (HA) and neuraminidase (NA) proteins, and six internal core polypeptides: the nucleocapsid nucleoprotein (NP); matrix proteins (M); non-structural proteins (NS); and 3 RNA polymerase (PA, PB1, PB2) proteins. During replication, the genomic viral RNA is transcribed into (+) strand messenger RNA and (−) strand genomic cRNA in the nucleus of the host cell. Each of the eight genomic segments is packaged into ribonucleoprotein complexes that contain, in addition to the RNA, NP and a polymerase complex (PB1, PB2, and PA).

Influenza is commonly grouped into influenza A and influenza B categories. Influenza A and influenza B viruses each contain eight segments of single stranded RNA with negative polarity. The influenza A genome encodes eleven polypeptides. Segments 1-3 encode three polypeptides, making up a RNA-dependent RNA polymerase. Segment 1 encodes the polymerase complex protein PB2. The remaining polymerase proteins PB1 and PA are encoded by segment 2 and segment 3, respectively. In addition, segment 1 of some influenza strains encodes a small protein, PB1-F2, produced from an alternative reading frame within the PB1 coding region. Segment 4 encodes the hemagglutinin (HA) surface glycoprotein involved in cell attachment and entry during infection. Segment 5 encodes the nucleocapsid nucleoprotein (NP) polypeptide, the major structural component associated with viral RNA. Segment 6 encodes a neuraminidase (NA) envelope glycoprotein. Segment 7 encodes two matrix proteins, designated M1 and M2, which are translated from differentially spliced mRNAs. Segment 8 encodes NS1 and NS2, two nonstructural proteins, which are translated from alternatively spliced mRNA variants. The eight genome segments of influenza B encode 11 proteins. The three largest genes code for components of the RNA polymerase, PB1, PB2 and PA. Segment 4 encodes the HA protein. Segment 5 encodes NP. Segment 6 encodes the NA protein and the NB protein. Both proteins, NB and NA, are translated from overlapping reading frames of a bicistronic mRNA. Segment 7 of influenza B also encodes two proteins: M1 and BM2. The smallest segment encodes two products: NS1 is translated from the full length RNA, while NS2 is translated from a spliced mRNA variant.

Influenza Virus Vaccines

The sequences, compositions and methods herein are primarily, but not solely, concerned with production of influenza viruses for vaccines. Historically, influenza virus vaccines have primarily been produced in embryonated hen eggs using strains of virus selected or based on empirical predictions of relevant strains. More recently, reassortant viruses have been produced that incorporate selected hemagglutinin and/or neuraminidase antigens in the context of an approved attenuated, temperature sensitive master strain. Following culture of the virus through multiple passages in hen eggs, influenza viruses are recovered and, optionally, inactivated, e.g., using formaldehyde and/or β-propiolactone (or alternatively used in live attenuated vaccines). Thus, it will be appreciated that HA and NA sequences (e.g., SEQ ID NO: 1-20) are quite useful in constructing influenza vaccines. The current invention includes viruses/vaccines comprising HA and/or NA sequences of pandemic influenza strains (including wherein the HA sequences comprise modified polybasic cleavage sites such as the modifications described herein); and including wherein the viruses/vaccines comprise a ca backbone such as A/AA/6/60 or the backbone of PR8.

Attempts at producing recombinant and reassortant vaccines in cell culture have been hampered by the inability of some of the strains approved for vaccine production to grow efficiently under standard cell culture conditions. However, prior work by the inventors and their coworkers provided a vector system, and methods for producing recombinant and reassortant viruses in culture, thus, making it possible to rapidly produce vaccines corresponding to one or many selected antigenic strains of virus, e.g., either A or B strains, various subtypes or substrains, etc., e.g., comprising the HA and/or NA sequences herein. See, Multi-Plasmid System for the production of Influenza virus, U.S. Application No. 60/420,708, filed Oct. 23, 2002, U.S. application Ser. No. 10/423,828, filed Apr. 25, 2003 and U.S. Application 60/574,117 filed May 24, 2004. Typically, the cultures are maintained in a system, such as a cell culture incubator, under controlled humidity and $CO_2$, at constant temperature using a temperature regulator, such as a thermostat to insure that the temperature does not exceed 35° C. Reassortant influenza viruses can be readily obtained by introducing a subset of vectors corresponding to genomic segments of a master influenza virus, in combination with complementary segments derived from strains of interest (e.g., HA and/or NA antigenic variants herein). Typically, the master strains are selected on the basis of desirable properties relevant to vaccine administration. For example, for vaccine production, e.g., for production of a live attenuated vaccine, the master donor virus strain may be selected for an attenuated phenotype, cold adaptation and/or temperature sensitivity. As explained elsewhere herein and, e.g., in U.S. patent application Ser. No. 10/423,828, etc., various embodiments of the invention utilize A/Ann Arbor (AA)/6/60 influenza strain as a "backbone" upon which to add HA and/or NA genes (e.g., such as those sequences listed herein, etc.) to create desired reassortant viruses. Thus, for example, in a 6:2 reassortant, 2 genes (i.e., NA and HA) would be from the influenza strain(s) against which an immunogenic reaction is desired, while the other 6 genes would be from the Ann Arbor strain, or other backbone strain, etc. The Ann Arbor virus is useful for its cold adapted, attenuated, temperature sensitive attributes. Of course, it will be appreciated that the HA and NA sequences herein are capable of reassortment with a number of other virus genes or virus types (e.g., a number of different "backbones" such as PR8, etc., containing the other influenza genes present in a reassortant, namely, the non-HA and non-NA genes Various embodiments herein can comprise live attenuated vaccines, having the HA and/or NA sequences herein, for pandemic influenza. Such vaccines typically comprise, e.g., the HA and/or NA sequences of SEQ ID NO: 11-20, or their corresponding nucleotides of SEQ ID NO: 1-10. One problem arising from growth of vaccine virus strains (e.g., reassortants) in eggs is that avian strains (which can be involved in pandemics) can kill the eggs in which the vaccines are to be produced and are, thus, hard to manipulate, produce, etc. through use of traditional (non-plasmid rescue) reassortant production. Such avian strains are of interest since evidence indicates they can result in influenza in humans and possible pandemics. Thus, use of plasmid-rescue systems to create/manipulate influenza reassortants with pandemic strains such as various avian sequences (e.g., the HA and NA sequences herein) are quite desirable and are features of the invention. It will be appreciated, however, that the current sequences are also capable of use with non-plasmid or traditional systems.

Aquatic birds (among others) can be infected by influenza A viruses of 15 hemagglutinin (HA) and 9 neuraminidase (NA) subtypes. Such birds can serve as a reservoir from which novel influenza subtypes can be introduced into human populations and cause pandemics. The observation that avian H7N7 influenza A viruses infected humans in The Netherlands in 2003 and avian H5N1 and H9N2 viruses infected humans in Hong Kong and China earlier, raise concerns that these (and other) subtypes have the potential to cause pandemics. Thus, vaccines are needed to prevent human infections with avian influenza A viruses. Live, attenuated influenza A virus vaccines against human influenza viruses were recently licensed in the United States. See above. Such vaccines are reassortant H1N1 and H3N2 viruses in which the internal protein genes of A/Ann Arbor (AA)/6/60 (H2N2) cold adapted (ca) virus confer the cold adapted, attenuation and temperature sensitive phenotypes of the AA ca virus on the reassortant viruses (i.e., the ones having the hemagglutinin and neuraminidase genes from the non-Ann Arbor strain). Classical genetic reassortment and plasmid-based reverse genetics techniques have been applied to generate reassortant viruses that contain the hemagglutinin and neuraminidase genes from avian influenza A viruses (H4-H14 subtypes) and six internal gene segments from the AA ca virus. Such reassortant viruses are features of the invention. See the HA and NA gene sequences below. These viruses bear biological properties that are desirable in candidate vaccines because the phenotypes associated with the AA ca virus are present in the reassortant viruses. The generation and evaluation of these reassortant viruses as seed viruses for vaccines are important steps in pandemic preparedness. It is contemplated that clinical trials can establish the safety, infectivity and immunogenicity of such live attenuated pandemic vaccines. Other embodiments of the invention include reassortant viruses (e.g., those used in vaccines) comprising pandemic antigenic genes HA and/or NA from, e.g., avian, porcine, etc., pandemic virus strains in addition to those listed herein, to produce pandemic vaccines which are created through plasmid-rescue reassortment (e.g., reassortment with A/Ann Arbor 6/60 (i.e., A/AA/6/60), PR8, etc. Methods of construction and use of such viruses and vaccines are also included. "Pandemic virus strains" as used herein is defined as an influenza strain A virus subtype that it is not circulating in the human population, that is declared to be a pandemic strain by the Centers for Disease Control or the World Health Organization or generally acknowledged as such within the scientific community.

In various embodiments herein, the antigenic sequences (e.g., the HA sequences) as well as viruses and vaccines from such viruses comprise modified polybasic cleavage sites. Some highly pathogenic avian pandemic influenza strains comprise multiple basic amino acid cleavage sites within hemagglutinin sequences. See, e.g., Li et al., *J. of Infectious Diseases*, 179:1132-8, 1999. Such cleavage sites, in typical embodiments herein, are, e.g., modified or altered in their sequences in comparison to the wild-type sequences from which the current sequences are derived (e.g., to disable the cleavage or reduce the cleavage there, etc.). Such modifications/alterations can be different in different strains due to the various sequences of the cleavage sites in the wild-type sequences. For example, 4 polybasic residues (RRKK: residues 6-9 of SEQ ID NO:22) at 326-329 of mature H5 are typically removed in sequences herein (as compared to wt). See sequence listing and FIG. 1. In various embodiments, the polybasic cleavage sites can be modified in a number of ways (all of which are contained within the invention). For example, the polybasic cleavage site can be removed one amino acid at a time (e.g., one R removed, two Rs removed, RRK removed, or RRKK (residues 6-9 of SEQ ID NO:22) removed). Additionally, the amino acid residue directly upstream of the cleavage site can also be removed or altered (e.g., from an R to a T, etc.); also, the nucleotides encoding the amino acid residue directly after the cleavage site can also be modified. See, e.g., FIG. 1 for an illustration of cleavage site modification. In addition, hemagglutinin polypeptide sequences of influenza virus comprise amino terminal signal peptide sequences, thus, the hemagglutinin polypeptide sequences of the invention include both the mature (amino terminal signal peptide cleaved) form of the hemagglutinin polypeptides and the pre-cleaved form of hemagglutinin. The cleavage sites of any hemagglutinin polypeptide sequence of any influenza strain can be routinely measured or predicted using any number of methods in the art.

The terms "temperature sensitive," "cold adapted" and "attenuated" as applied to viruses (typically used as vaccines or for vaccine production) which optionally encompass the current sequences, are well known in the art. For example, the term "temperature sensitive" (ts) indicates, e.g., that the virus exhibits a 100 fold or greater reduction in titer at 39° C. relative to 33° C. for influenza A strains, or that the virus exhibits a 100 fold or greater reduction in titer at 37° C. relative to 33° C. for influenza B strains. The term "cold adapted" (ca) indicates that the virus exhibits growth at 25° C. within 100 fold of its growth at 33° C., while the term "attenuated" (att) indicates that the virus replicates in the upper airways of ferrets but is not detectable in their lung tissues, and does not cause influenza-like illness in the animal. It will be understood that viruses with intermediate phenotypes, i.e., viruses exhibiting titer reductions less than 100 fold at 39° C. (for A strain viruses) or 37° C. (for B strain viruses), or exhibiting growth at 25° C. that is more than 100 fold than its growth at 33° C. (e.g., within 200 fold, 500 fold, 1000 fold, 10,000 fold less), and/or exhibit reduced growth in the lungs relative to growth in the upper airways of ferrets (i.e., partially attenuated) and/or reduced influenza like illness in the animal, are also useful viruses and can be used in conjunction with the HA and NA sequences herein.

Again, the HA and NA sequences of the current invention are optionally utilized in such plasmid reassortment vaccines (and/or in other ts, cs, ca, and/or att viruses and vaccines). However, it should be noted that the HA and NA sequences, etc. of the invention are not limited to specific vaccine compositions or production methods, and can, thus, be utilized in substantially any vaccine type or vaccine production method which utilizes strain specific HA and NA antigens (e.g., any of SEQ ID NO: 11-20 or the corresponding nucleotides in SEQ ID NO: 1-10).

FluMist™

As mentioned previously, numerous examples and types of influenza vaccine exist. An exemplary influenza vaccine is FluMist™ which is a live, attenuated vaccine that protects children and adults from influenza illness (Belshe et al. (1998) *The efficacy of live attenuated, cold-adapted, trivalent, intranasal influenza virus vaccine in children* N Engl J Med 338:1405-12; Nichol et al. (1999) *Effectiveness of live, attenuated intranasal influenza virus vaccine in healthy, working adults: a randomized controlled trial* JAMA 282: 137-44). In typical, and preferred, embodiments, the methods and compositions of the current invention are preferably adapted to/used with production of FluMist™ vaccine. However, it will be appreciated by those skilled in the art that the sequences, methods, compositions, etc. herein are also adaptable to production of similar or even different viral vaccines.

FluMist™ vaccine strains contain, e.g., HA and NA gene segments derived from the strains (e.g., wild-type strains) to which the vaccine is addressed along with six gene segments, PB1, PB2, PA, NP, M and NS, from a common master donor virus (MDV). The HA sequences herein, thus, are part of various FluMist™ formulations. The MDV for influenza A strains of FluMist™ (MDV-A), was created by serial passage of the wild-type A/Ann Arbor/6/60 (A/AA/6/60) strain in primary chicken kidney tissue culture at successively lower temperatures (Maassab (1967) *Adaptation and growth characteristics of influenza virus at 25 degrees C Nature* 213:612-4). MDV-A replicates efficiently at 25° C. (ca, cold adapted), but its growth is restricted at 38 and 39° C. (ts, temperature sensitive). Additionally, this virus does not replicate in the lungs of infected ferrets (att, attenuation). The ts phenotype is believed to contribute to the attenuation of the vaccine in humans by restricting its replication in all but the coolest regions of the respiratory tract. The stability of this property has been demonstrated in animal models and clinical studies. In contrast to the ts phenotype of influenza strains created by chemical mutagenesis, the ts property of MDV-A does not revert following passage through infected hamsters or in shed isolates from children (for a recent review, see Murphy & Coelingh (2002) *Principles underlying the development and use of live attenuated cold-adapted influenza A and B virus vaccines Viral Immunol* 15:295-323).

Clinical studies in over 20,000 adults and children involving 12 separate 6:2 reassortant strains have shown that these vaccines are attenuated, safe and efficacious (Belshe et al. (1998) *The efficacy of live attenuated, cold-adapted, trivalent, intranasal influenza virus vaccine in children N Engl J Med* 338:1405-12; Boyce et al. (2000) *Safety and immunogenicity of adjuvanted and unadjuvanted subunit influenza vaccines administered intranasally to healthy adults Vaccine* 19:217-26; Edwards et al. (1994) *A randomized controlled trial of cold adapted and inactivated vaccines for the prevention of influenza A disease J Infect Dis* 169:68-76; Nichol et al. (1999) *Effectiveness of live, attenuated intranasal influenza virus vaccine in healthy, working adults: a randomized controlled trial JAMA* 282: 137-44). Reassortants carrying the six internal genes of MDV-A and the two HA and NA gene segments of a wild-type virus (i.e., a 6:2 reassortant) consistently maintain ca, ts and att phenotypes (Maassab et al. (1982) *Evaluation of a cold-recombinant influenza virus vaccine in ferrets J. Infect. Dis.* 146:780-900).

Production of such reasserted virus using B strains of influenza is more difficult, however, recent work (see, e.g., Multi-Plasmid System for the Production of Influenza Virus, U.S. Application No. 60/420,708, filed Oct. 23, 2002, U.S. application Ser. No. 10/423,828, filed Apr. 25, 2003, and U.S. Application No. 60/574,117, filed May 24, 2004) has shown an eight plasmid system for the generation of influenza B virus entirely from cloned cDNA. Methods for the production of attenuated live influenza A and B virus suitable for vaccine formulations, such as live virus vaccine formulations useful for intranasal administration were also shown.

The system and methods described previously are useful for the rapid production in cell culture of recombinant and reassortant influenza A and B viruses, including viruses suitable for use as vaccines, including live attenuated vaccines, such as vaccines suitable for intranasal administration. The sequences (e.g., SEQ ID NO: 1-10 and the corresponding amino acids in SEQ ID NO: 11-20), methods, etc. of the current invention, are optionally used in conjunction with, or in combination with, such previous work involving, e.g., reasserted influenza viruses for vaccine production to produce viruses for vaccines.

Methods and Compositions for Prophylactic Administration of Vaccines

As stated above, alternatively, or in addition to, use in production of FluMist™ vaccine, the current invention can be used in other vaccine formulations. In general, recombinant and reassortant viruses of the invention (e.g., those comprising polynucleotides of SEQ ID NO:1-10 or polypeptides of SEQ ID NO:11-20, or fragments thereof) can be administered prophylactically in an immunologically effective amount and in an appropriate carrier or excipient to stimulate an immune response specific for one or more strains of influenza virus as determined by the HA and/or NA sequence. Typically, the carrier or excipient is a pharmaceutically acceptable carrier or excipient, such as sterile water, aqueous saline solution, aqueous buffered saline solutions, aqueous dextrose solutions, aqueous glycerol solutions, ethanol, or combinations thereof. The preparation of such solutions insuring sterility, pH, isotonicity, and stability is effected according to protocols established in the art. Generally, a carrier or excipient is selected to minimize allergic and other undesirable effects, and to suit the particular route of administration, e.g., subcutaneous, intramuscular, intranasal, etc.

A related aspect of the invention provides methods for stimulating the immune system of an individual to produce a protective immune response against influenza virus. In the methods, an immunologically effective amount of a recombinant influenza virus (e.g., comprising an HA and/or NA molecule of the invention), an immunologically effective amount of a polypeptide of the invention, and/or an immunologically effective amount of a nucleic acid of the invention is administered to the individual in a physiologically acceptable carrier.

Generally, the influenza viruses of the invention are administered in a quantity sufficient to stimulate an immune response specific for one or more strains of influenza virus (i.e., against the HA and/or NA strains of the invention). Preferably, administration of the influenza viruses elicits a protective immune response to such strains. Dosages and methods for eliciting a protective immune response against one or more influenza strains are known to those of skill in the art. See, e.g., U.S. Pat. No. 5,922,326; Wright et al., *Infect. Immun.* 37:397-400 (1982); Kim et al., *Pediatrics* 52:56-63 (1973); and Wright et al., *J. Pediatr.* 88:931-936 (1976). For example, influenza viruses are provided in the range of about 1-1000 $HID_{50}$ (human infectious dose), i.e., about $10^5$-$10^8$ pfu (plaque forming units) per dose administered. Typically, the dose will be adjusted within this range based on, e.g., age, physical condition, body weight, sex, diet, time of administration, and other clinical factors. The prophylactic vaccine formulation is systemically administered, e.g., by subcutaneous or intramuscular injection using a needle and syringe, or a needle-less injection device. Alternatively, the vaccine formulation is administered intranasally, either by drops, large particle aerosol (greater than about 10 microns), or spray into the upper respiratory tract. While any of the above routes of delivery results in a protective systemic immune response, intranasal administration confers the added benefit of eliciting mucosal immunity at the site of entry of the influenza virus. For intranasal administration, attenuated live virus vaccines are often preferred, e.g., an attenuated, cold adapted and/or temperature sensitive recombinant or reassortant influenza virus. See above. While stimulation of a protective immune response with a single dose is preferred, additional dosages can be administered, by the same or different route, to achieve the desired prophylactic effect.

Typically, the attenuated recombinant influenza of this invention as used in a vaccine is sufficiently attenuated such that symptoms of infection, or at least symptoms of serious infection, will not occur in most individuals immunized (or otherwise infected) with the attenuated influenza virus. In some instances, the attenuated influenza virus can still be capable of producing symptoms of mild illness (e.g., mild upper respiratory illness) and/or of dissemination to unvaccinated individuals. However, its virulence is sufficiently abrogated such that severe lower respiratory tract infections do not occur in the vaccinated or incidental host.

Alternatively, an immune response can be stimulated by ex vivo or in vivo targeting of dendritic cells with influenza viruses comprising the sequences herein. For example, proliferating dendritic cells are exposed to viruses in a sufficient amount and for a sufficient period of time to permit capture of the influenza antigens by the dendritic cells. The cells are then transferred into a subject to be vaccinated by standard intravenous transplantation methods.

While stimulation of a protective immune response with a single dose is preferred, additional dosages can be administered, by the same or different route, to achieve the desired prophylactic effect. In neonates and infants, for example, multiple administrations may be required to elicit sufficient levels of immunity. Administration can continue at intervals throughout childhood, as necessary to maintain sufficient levels of protection against wild-type influenza infection. Similarly, adults who are particularly susceptible to repeated or serious influenza infection, such as, for example, health care workers, day care workers, family members of young children, the elderly, and individuals with compromised cardiopulmonary function may require multiple immunizations to establish and/or maintain protective immune responses. Levels of induced immunity can be monitored, for example, by measuring amounts of neutralizing secretory and serum antibodies, and dosages adjusted or vaccinations repeated as necessary to elicit and maintain desired levels of protection.

Optionally, the formulation for prophylactic administration of the influenza viruses also contains one or more adjuvants for enhancing the immune response to the influenza antigens. Suitable adjuvants include: complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, bacille Calmette-Guerin (BCG), *Corynebacterium parvum*, and the synthetic adjuvant QS-21.

If desired, prophylactic vaccine administration of influenza viruses can be performed in conjunction with administration of one or more immunostimulatory molecules. Immunostimulatory molecules include various cytokines, lymphokines and chemokines with immunostimulatory, immunopotentiating, and pro-inflammatory activities, such as interleukins (e.g., IL-1, IL-2, IL-3, IL-4, IL-12, IL-13); growth factors (e.g., granulocyte-macrophage (GM)-colony stimulating factor (CSF)); and other immunostimulatory molecules, such as macrophage inflammatory factor, Flt3 ligand, B7.1; B7.2, etc. The immunostimulatory molecules can be administered in the same formulation as the influenza viruses, or can be administered separately. Either the protein (e.g., an HA and/or NA polypeptide of the invention, e.g., any of SEQ ID NO: 11-20) or an expression vector comprising a nucleic acid (e.g., any of SEQ ID NO: 1-10) encoding the protein can be administered to produce an immunostimulatory effect.

The above described methods are useful for therapeutically and/or prophylactically treating a disease or disorder, typically influenza, by introducing a vector of the invention comprising a heterologous polynucleotide encoding a therapeutically or prophylactically effective HA and/or NA polypeptide (or peptide) or HA and/or NA RNA (e.g., an antisense RNA or ribozyme) into a population of target cells in vitro, ex vivo or in vivo. Typically, the polynucleotide encoding the polypeptide (or peptide), or RNA, of interest is operably linked to appropriate regulatory sequences as described above in the sections entitled "Expression Vectors" and "Additional Expression Elements." Optionally, more than one heterologous coding sequence is incorporated into a single vector or virus. For example, in addition to a polynucleotide encoding a therapeutically or prophylactically active HA and/or NA polypeptide or RNA, the vector can also include additional therapeutic or prophylactic polypeptides, e.g., antigens, co-stimulatory molecules, cytokines, antibodies, etc., and/or markers, and the like.

Although vaccination of an individual with an attenuated influenza virus of a particular strain of a particular subgroup can induce cross-protection against influenza virus of different strains and/or subgroups, cross-protection can be enhanced, if desired, by vaccinating the individual with attenuated influenza virus from at least two strains, e.g., each of which represents a different subgroup. Additionally, vaccine combinations can optionally include mixes of pandemic vaccines (e.g., those against pandemic influenza strains such as various avian strains, see, e.g., the sequences herein, or other pandemic strains) and non-pandemic strains. Vaccine mixtures (or multiple vaccinations) can comprise components from human strains and/or non-human influenza strains (e.g., avian and human, etc.). Similarly, the attenuated influenza virus vaccines of this invention can optionally be combined with vaccines that induce protective immune responses against other infectious agents.

Polynucleotides of the Invention

It is well known in the art that the HA and NA polynucleotide segments of influenza viruses comprise both a coding region (encoding the ORF) and noncoding regions (NCRs), both 5' and 3' of the HA and NA coding sequence. An example of these NCRs are shown in SEQ ID NOS:1-9 (outside of the ORFs). It is also known that primers can be made to these NCRs to facilitate amplification of the entire HA and NA segments of influenza virus. (see, e.g., Hoffmann et al. Arch Virol. 2001 December; 146(12):2275-89). Further, it is known that the NCRs of the HA and NA of influenza may increase the efficiency of achieving reassortants. Therefore, the polynucleotide sequences of these NCRs (including fragments and variants (e.g., at least about 60%, or at least 70%, or at least 80%, or at least 90%, or at least about 91% or at least about 92%, or at least about 93%, or at least about 94%, or at least about 95%, or at least about 96%, or at least about 97%, or at least about 98%, or at least about 98.5%, or at least about 98.7%, or at least about 99%, or at least about 99.1%, or at least about 99.2%, or at least about 99.3%, or at least about 99.4%, or at least about 99.5%, or at least about 99.6% or at least about 99.7%, or at least about 99.8%, or at least about 99.9% identity) thereof) are within the scope of this invention. When amplifying the HA and NA segments of any pandemic strain, one could make and use polynucleotide primers to bind conserved (e.g., among related strains) regions of the HA and NA NCRs for amplification (e.g., by RT-PCR). In one embodiment, HA and NA polynucleotides of the invention include both the NCR and ORF of the HA and NA sequences (including fragments and variants (e.g., at least about 60%, or at least 70%, or at least 80%, or at least 90%, or at least about 91% or at least about 92%, or at least about 93%, or at least about 94%, or at least about 95%, or at least about 96%, or at least about 97%, or at least about 98%, or at least about 98.5%, or at least about 98.7%, or at least about 99%, or at least about 99.1%, or at least about 99.2%, or at least about 99.3%, or at least about 99.4%, or at least about 99.5%, or at least about 99.6% or at least about 99.7%, or at least about 99.8%, or at least about 99.9%) thereof) of pandemic virus strains. In alternative embodiments, the HA and NA polynucleotides of the invention exclude the NCR, but include the ORF (including fragments and variants (e.g., at least about 60%, or at least 70%, or at least 80%, or at least 90%, or at least about 91% or at least about 92%, or at least about 93%, or at least about 94%, or at least about 95%, or at least about 96%, or at least about 97%, or at least about 98%, or at least about 98.5%, or at least about 98.7%, or at least about 99%, or at least about 99.1%, or at least about 99.2%, or at least about 99.3%, or at least about 99.4%, or at least about 99.5%, or at least about 99.6% or at least about 99.7%, or at least about 99.8%, or at least about 99.9% thereof)) of the HA and NA sequences of pandemic virus strains (e.g., SEQ ID NOS: 1-9).

The HA and NA polynucleotides of the invention, e.g., SEQ ID NO:1 through SEQ ID NO:10, and fragments thereof, are optionally used in a number of different capacities alternative to, or in addition to, the vaccines described above. Other exemplary uses are described herein for illustrative purpose and not as limitations on the actual range of uses. Different methods of construction, purification, and characterization of the nucleotide sequences of the invention are also described herein. In some embodiments, nucleic acids including one or more polynucleotide sequence of the invention are favorably used as probes for the detection of corresponding or related nucleic acids in a variety of contexts, such as in nucleic hybridization experiments, e.g., to find and/or characterize homologous influenza variants (e.g., homologues to the sequences herein, etc.) infecting other species or in different influenza outbreaks, etc. The probes can be either DNA or RNA molecules, such as restriction fragments of genomic or cloned DNA, cDNAs, PCR amplification products, transcripts, and oligonucleotides, and can vary in length from oligonucleotides as short as about 10 nucleotides in length to full length sequences or cDNAs in excess of 1 kb or more. For example, in some embodiments, a probe of the invention includes a polynucleotide sequence or subsequence selected, e.g., from among SEQ ID NO: 1 through SEQ ID NO: 10, or sequences complementary thereto. Alternatively, polynucleotide sequences that are variants of one of the above-designated sequences are used as probes. Most typically, such variants include one or a few conservative nucleotide variations. For example, pairs (or sets) of oligonucleotides can be selected, in which the two (or more) polynucleotide sequences are conservative variations of each other, wherein one polynucleotide sequence corresponds identically to a first variant or and the other(s) corresponds identically to additional variants. Such pairs of oligonucleotide probes are particularly useful, e.g., for specific hybridization experiments to detect polymorphic nucleotides or to, e.g., detect homologous influenza HA and NA variants, e.g., homologous to the current HA and NA sequences, infecting other species or present in different (e.g., either temporally and/or geographically different) influenza outbreaks. In other applications, probes are selected that are more divergent, that is probes that are at least about 91% (or about 92%, about 93%, about 94%, about 95%, about 96%, about 97%, about 98%, about 98.5%, about 98.7%, about 99%, about 99.1%, about 99.2%, about 99.3%, about 99.4%, about 99.5%, or about 99.6% or more about 99.7%, about 99.8%, about 99.9% or more) identical are selected.

The probes of the invention, e.g., as exemplified by sequences derived from the sequences herein, can also be used to identify additional useful polynucleotide sequences according to procedures routine in the art. In one set of embodiments, one or more probes, as described above, are utilized to screen libraries of expression products or chromosomal segments (e.g., expression libraries or genomic libraries) to identify clones that include sequences identical to, or with significant sequence similarity to, e.g., one or more probe of the sequences herein, i.e., variants, homologues, etc. It will be understood that in addition to such physical methods as library screening, computer assisted bioinformatic approaches, e.g., BLAST and other sequence homology search algorithms, and the like, can also be used for identifying related polynucleotide sequences. Polynucleotide sequences identified in this manner are also a feature of the invention.

Oligonucleotide probes are optionally produced via a variety of methods well known to those skilled in the art. Most typically, they are produced by well known synthetic methods, such as the solid phase phosphoramidite triester method described by Beaucage and Caruthers (1981) *Tetrahedron Letts* 22(20): 1859-1862, e.g., using an automated synthesizer, or as described in Needham-Van Devanter et al. (1984) *Nucl Acids Res,* 12:6159-6168. Oligonucleotides can also be custom made and ordered from a variety of commercial sources known to persons of skill. Purification of oligonucleotides, where necessary, is typically performed by either native acrylamide gel electrophoresis or by anion-exchange HPLC as described in Pearson and Regnier (1983) *J Chrom* 255: 137-149. The sequence of the synthetic oligonucleotides can be verified using the chemical degradation method of Maxam and Gilbert (1980) in Grossman and Moldave (eds.) Academic Press, New York, *Methods in Enzymology* 65:499-560. Custom oligos can also easily be ordered from a variety of commercial sources known to persons of skill.

In other circumstances, e.g., relating to attributes of cells or organisms expressing the polynucleotides and polypeptides of the invention (e.g., those harboring virus comprising the sequences of the invention), probes that are polypeptides, peptides or antibodies are favorably utilized. For example, isolated or recombinant polypeptides, polypeptide fragments and peptides derived from any of the amino acid sequences of the invention (e.g., SEQ ID NO: 11-20) and/or encoded by polynucleotide sequences of the invention, e.g., selected from SEQ ID NO: 1 through SEQ ID NO: 10, are favorably used to identify and isolate antibodies, e.g., from phage display libraries, combinatorial libraries, polyclonal sera, and the like. Polypeptide fragments of the inventions include a peptide or polypeptide comprising an amino acid sequence of at least 5 contiguous amino acid residues, or at least 10 contiguous amino acid residues, or at least 15 contiguous amino acid residues, or at least 20 contiguous amino acid residues, or at least 25 contiguous amino acid residues, or at least 40 contiguous amino acid residues, or at least 50 contiguous amino acid residues, or at least 60 contiguous amino residues, or at least 70 contiguous amino acid residues, or at least contiguous 80 amino acid residues, or at least contiguous 90 amino acid residues, or at least contiguous 100 amino acid residues, or at least contiguous 125 amino acid residues, or at least 150 contiguous amino acid residues, or at least contiguous 175 amino acid residues, or at least contiguous 200 amino acid residues, or at least contiguous 250 amino acid residues, or at least contiguous 350, or at least contiguous 400, or at least contiguous 450, or at least contiguous 500, or at least contiguous 550 amino acid residues of the amino acid sequence an HA or NA polypeptide of the invention (e.g., SEQ ID Nos: 11-20). Polynucleotides encoding said polypeptide fragments and antibodies that specifically bind said polypeptides are also preferred embodiments of the invention.

Antibodies specific for any a polypeptide sequence or subsequence, e.g., of SEQ ID NO: 11 through SEQ ID NO: 20, and/or encoded by polynucleotide sequences of the invention, e.g., selected from SEQ ID NO: 1 through SEQ ID NO: 10, are likewise valuable as probes for evaluating expression products, e.g., from cells or tissues. In addition, antibodies are particularly suitable for evaluating expression of proteins comprising amino acid subsequences, e.g., of those given herein, or encoded by polynucleotides sequences of the invention, e.g., selected from those shown herein, in situ, in a tissue array, in a cell, tissue or organism, e.g., an organism infected by an unidentified influenza virus or the like. Antibodies can be directly labeled with a detectable reagent, or detected indirectly by labeling of a secondary antibody specific for the heavy chain constant region (i.e., isotype) of the specific antibody. Additional details regarding production of specific antibodies are provided below.

Diagnostic Assays

The nucleic acid sequences of the present invention can be used in diagnostic assays to detect influenza (and/or hemagglutinin and/or neuraminidase) in a sample, to detect hemagglutinin-like and/or neuraminidase-like sequences, and to detect strain differences in clinical isolates of influenza using either chemically synthesized or recombinant polynucleotide fragments, e.g., selected from the sequences herein. For example, fragments of the hemagglutinin and/or neuraminidase sequences comprising at least between 10 and 20 nucleotides can be used as primers to amplify nucleic acids using polymerase chain reaction (PCR) methods well known in the art (e.g., reverse transcription-PCR) and as probes in nucleic acid hybridization assays to detect target genetic material such as influenza RNA in clinical specimens.

The probes of the invention, e.g., as exemplified by unique subsequences selected from those given herein, can also be used to identify additional useful polynucleotide sequences (such as to characterize additional strains of influenza) according to procedures routine in the art. In one set of preferred embodiments, one or more probes, as described above, are utilized to screen libraries of expression products or cloned viral nucleic acids (i.e., expression libraries or genomic libraries) to identify clones that include sequences identical to, or with significant sequence identity to the sequences herein. In turn, each of these identified sequences can be used to make probes, including pairs or sets of variant probes as described above. It will be understood that in addition to such physical methods as library screening, computer assisted bioinformatic approaches, e.g., BLAST and other sequence homology search algorithms, and the like, can also be used for identifying related polynucleotide sequences.

The probes of the invention are particularly useful for detecting the presence and for determining the identity of influenza nucleic acids in cells, tissues or other biological samples (e.g., a nasal wash or bronchial lavage). For example, the probes of the invention are favorably utilized to determine whether a biological sample, such as a subject (e.g., a human subject) or model system (such as a cultured cell sample) has been exposed to, or become infected with influenza, or particular strain(s) of influenza. Detection of hybridization of the selected probe to nucleic acids originating in (e.g., isolated from) the biological sample or model system is indicative of exposure to or infection with the virus (or a related virus) from which the probe polynucleotide is selected.

It will be appreciated that probe design is influenced by the intended application. For example, where several allele-specific probe-target interactions are to be detected in a single assay, e.g., on a single DNA chip, it is desirable to have similar melting temperatures for all of the probes. Accordingly, the lengths of the probes are adjusted so that the melting temperatures for all of the probes on the array are closely similar (it will be appreciated that different lengths for different probes may be needed to achieve a particular $T_m$ where different probes have different GC contents). Although melting temperature is a primary consideration in probe design, other factors are optionally used to further adjust probe construction, such as selecting against primer self-complementarity and the like.

Vectors, Promoters and Expression Systems

The present invention includes recombinant constructs incorporating one or more of the nucleic acid sequences described herein. Such constructs optionally include a vector, for example, a plasmid, a cosmid, a phage, a virus, a bacterial artificial chromosome (BAC), a yeast artificial chromosome (YAC), etc., into which one or more of the polynucleotide sequences of the invention, e.g., comprising any of SEQ ID NO: 1 through SEQ ID NO:10, or a subsequence thereof etc., has been inserted, in a forward or reverse orientation. For example, the inserted nucleic acid can include a viral chromosomal sequence or cDNA including all or part of at least one of the polynucleotide sequences of the invention. In one embodiment, the construct further comprises regulatory sequences, including, for example, a promoter, operably linked to the sequence. Large numbers of suitable vectors and promoters are known to those of skill in the art, and are commercially available.

The polynucleotides of the present invention can be included in any one of a variety of vectors suitable for generating sense or antisense RNA, and optionally, polypeptide (or peptide) expression products (e.g., a hemagglutinin and/or neuraminidase molecule of the invention, or fragments thereof). Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, pseudorabies, adenovirus, adeno-associated virus, retroviruses and many others (e.g., pCDL). Any vector that is capable of introducing genetic material into a cell, and, if replication is desired, which is replicable in the relevant host can be used.

In an expression vector, the HA and/or NA polynucleotide sequence of interest is physically arranged in proximity and orientation to an appropriate transcription control sequence (e.g., promoter, and optionally, one or more enhancers) to direct mRNA synthesis. That is, the polynucleotide sequence of interest is operably linked to an appropriate transcription control sequence. Examples of such promoters include: LTR or SV40 promoter, *E. coli* lac or trp promoter, phage lambda $P_L$ promoter, and other promoters known to control expression of genes in prokaryotic or eukaryotic cells or their viruses.

A variety of promoters are suitable for use in expression vectors for regulating transcription of influenza virus genome segments. In certain embodiments, the cytomegalovirus (CMV) DNA dependent RNA Polymerase II (Pol II) promoter is utilized. If desired, e.g., for regulating conditional expression, other promoters can be substituted which induce RNA transcription under the specified conditions, or in the specified tissues or cells. Numerous viral and mammalian, e.g., human promoters are available, or can be isolated according to the specific application contemplated. For example, alternative promoters obtained from the genomes of animal and human viruses include such promoters as the adenovirus (such as Adenovirus 2), papilloma virus, hepatitis-B virus, polyoma virus, and Simian Virus 40 (SV40), and various retroviral promoters. Mammalian promoters include, among many others, the actin promoter, immunoglobulin promoters, heat-shock promoters, and the like.

Transcription is optionally increased by including an enhancer sequence. Enhancers are typically short, e.g., 10-500 bp, cis-acting DNA elements that act in concert with a promoter to increase transcription. Many enhancer sequences have been isolated from mammalian genes (hemoglobin, elastase, albumin, alpha-fetoprotein, and insulin), and eukaryotic cell viruses. The enhancer can be spliced into the vector at a position 5' or 3' to the heterologous coding sequence, but is typically inserted at a site 5' to the promoter. Typically, the promoter, and if desired, additional transcription enhancing sequences are chosen to optimize expression in the host cell type into which the heterologous DNA is to be introduced (Scharf et al. (1994) *Heat stress promoters and transcription factors Results Probl Cell Differ* 20:125-62; Kriegler et al. (1990) *Assembly of enhancers, promoters, and splice signals to control expression of transferred genes Methods in Enzymol* 185: 512-27). Optionally, the amplicon can also contain a ribosome binding site or an internal ribosome entry site (IRES) for translation initiation.

The vectors of the invention also favorably include sequences necessary for the termination of transcription and for stabilizing the mRNA, such as a polyadenylation site or a terminator sequence. Such sequences are commonly available from the 5' and, occasionally 3', untranslated regions of eukaryotic or viral DNAs or cDNAs. In one embodiment, the SV40 polyadenylation signal sequences can provide a bi-directional polyadenylation site that insulates transcription of (+) strand mRNA molecules from the PolI promoter initiating replication of the (−) strand viral genome.

In addition, as described above, the expression vectors optionally include one or more selectable marker genes to provide a phenotypic trait for selection of transformed host cells, in addition to genes previously listed, markers such as dihydrofolate reductase or neomycin resistance are suitable for selection in eukaryotic cell culture.

The vector containing the appropriate nucleic acid sequence as described above, as well as an appropriate promoter or control sequence, can be employed to transform a host cell permitting expression of the protein. While the vectors of the invention can be replicated in bacterial cells, most frequently it will be desirable to introduce them into mammalian cells, e.g., Vero cells, BHK cells, MDCK cell, 293 cells, COS cells, or the like, for the purpose of expression.

As described elsewhere, the HA and NA sequences herein, in various embodiments, can be comprised within plasmids involved in plasmid-rescue reassortment. See, e.g. U.S. Application Nos. 60/420,708, filed Oct. 23, 2002; 60/574,117, filed May 24, 2004; 10/423,828, filed Apr. 25, 2003; 60/578,962, filed Jun. 12, 2004; and 10/870,690 filed Jun. 16, 2004; and US20020164770, which are incorporated by reference herein. For example, preferred expression vectors of the invention include, but are not limited to, vectors comprising pol I promoter and terminator sequences or vectors using both the pol I and pol II promoters "the polI/polII promoter system" (e.g., Zobel et al., Nucl. Acids Res. 1993, 21:3607; US20020164770; Neumann et al., Proc. Natl. Acad. Sci. USA 1999, 96:9345; Fodor et al., J. Virol. 1999, 73:9679; and US20030035814). The reassortants produced can include the HA and NA genes arranged with the 6 other influenza genes from the A/Ann Arbor/6/60 donor strain (and/or derivatives and modifications thereof), the PR8 donor strain backbone, the A/Leningrad/17 donor strain backbone, etc. Other backbone strains are described, for example, in 20040137013 and 20030147916, which are incorporated by reference herein.

Additional Expression Elements

Most commonly, the genome segment encoding the influenza virus HA and/or NA protein includes any additional sequences necessary for its expression, including translation into a functional viral protein. In other situations, a minigene, or other artificial construct encoding the viral proteins, e.g., an HA and/or NA protein, can be employed. Again, in such case, it is often desirable to include specific initiation signals that aid in the efficient translation of the heterologous coding sequence. These signals can include, e.g., the ATG initiation codon and adjacent sequences. To insure translation of the entire insert, the initiation codon is inserted in the correct reading frame relative to the viral protein. Exogenous transcriptional elements and initiation codons can be of various origins, both natural and synthetic. The efficiency of expression can be enhanced by the inclusion of enhancers appropriate to the cell system in use.

If desired, polynucleotide sequences encoding additional expressed elements, such as signal sequences, secretion or localization sequences, and the like can be incorporated into the vector, usually, in-frame with the polynucleotide sequence of interest, e.g., to target polypeptide expression to a desired cellular compartment, membrane, or organelle, or to direct polypeptide secretion to the periplasmic space or into the cell culture media. Such sequences are known to those of skill, and include secretion leader peptides, organelle targeting sequences (e.g., nuclear localization sequences, ER retention signals, mitochondrial transit sequences), membrane localization/anchor sequences (e.g., stop transfer sequences, GPI anchor sequences), and the like.

Where translation of a polypeptide encoded by a nucleic acid sequence of the invention is desired, additional translation specific initiation signals can improve the efficiency of translation. These signals can include, e.g., an ATG initiation codon and adjacent sequences, an IRES region, etc. In some cases, for example, full-length cDNA molecules or chromosomal segments including a coding sequence incorporating, e.g., a polynucleotide sequence of the invention (e.g., as in the sequences herein), a translation initiation codon and associated sequence elements are inserted into the appropriate expression vector simultaneously with the polynucleotide sequence of interest. In such cases, additional translational control signals frequently are not required. However, in cases where only a polypeptide coding sequence, or a portion thereof, is inserted, exogenous translational control signals, including, e.g., an ATG initiation codon is often provided for expression of the relevant sequence. The initiation codon is put in the correct reading frame to ensure transcription of the polynucleotide sequence of interest. Exogenous transcriptional elements and initiation codons can be of various origins, both natural and synthetic. The efficiency of expression can be enhanced by the inclusion of enhancers appropriate to the cell system in use (see, e.g., Scharf D. et al. (1994) *Results Probl Cell Differ* 20:125-62; Bittner et al. (1987) *Methods in Enzymol* 153:516-544).

Production of Recombinant Virus

Negative strand RNA viruses can be genetically engineered and recovered using a recombinant reverse genetics approach (see, e.g., U.S. Pat. No. 5,166,057 to Palese et al.). Such method was originally applied to engineer influenza viral genomes (Luytjes et al. (1989) Cell 59:1107-1113; Enami et al. (1990) *Proc. Natl. Acad. Sci. USA* 92:11563-11567), and has been successfully applied to a wide variety of segmented and nonsegmented negative strand RNA viruses, e.g., rabies (Schnell et al. (1994) *EMBO J.* 13: 4195-4203); VSV (Lawson et al. (1995) *Proc. Natl. Acad. Sci. USA* 92: 4477-4481); measles virus (Radecke et al. (1995) *EMBO J.* 14:5773-5784); rinderpest virus (Baron & Barrett (1997) *J. Virol.* 71: 1265-1271); human parainfluenza virus (Hoffman & Banerjee (1997) *J. Virol.* 71: 3272-3277; Dubin et al. (1997) *Virology* 235:323-332); SV5 (He et al. (1997) *Virology* 237:249-260); canine distemper virus (Gassen et al. (2000) *J. Virol.* 74:10737-44); and Sendai virus (Park et al. (1991)

*Proc. Natl. Acad. Sci. USA* 88: 5537-5541; Kato et al. (1996) *Genes to Cells* 1:569-579). Those of skill in the art will be familiar with these and similar techniques to produce influenza virus comprising the HA and NA sequences of the invention. Recombinant influenza viruses produced according to such methods are also a feature of the invention, as are recombinant influenza virus comprising one or more nucleic acids and/or polypeptides of the invention.

Cell Culture and Expression Hosts

The present invention also relates to host cells that are introduced (transduced, transformed or transfected) with vectors of the invention, and the production of polypeptides of the invention by recombinant techniques. Host cells are genetically engineered (i.e., transduced, transformed or transfected) with a vector, such as an expression vector, of this invention. As described above, the vector can be in the form of a plasmid, a viral particle, a phage, etc. Examples of appropriate expression hosts include: bacterial cells, such as *E. coli, Streptomyces*, and *Salmonella typhimurium*; fungal cells, such as *Saccharomyces cerevisiae, Pichia pastoris*, and *Neurospora crassa*; or insect cells such as *Drosophila* and *Spodoptera frugiperda.*

Most commonly, mammalian cells are used to culture the HA and NA molecules of the invention. Suitable host cells for the replication of influenza virus include, e.g., Vero cells, BHK cells, MDCK cells, 293 cells and COS cells, including 293T cells, COS7 cells or the like. Commonly, co-cultures including two of the above cell lines, e.g., MDCK cells and either 293T or COS cells are employed at a ratio, e.g., of 1:1, to improve replication efficiency. Typically, cells are cultured in a standard commercial culture medium, such as Dulbecco's modified Eagle's medium supplemented with serum (e.g., 10% fetal bovine serum), or in serum free medium, under controlled humidity and $CO_2$ concentration suitable for maintaining neutral buffered pH (e.g., at pH between 7.0 and 7.2). Optionally, the medium contains antibiotics to prevent bacterial growth, e.g., penicillin, streptomycin, etc., and/or additional nutrients, such as L-glutamine, sodium pyruvate, non-essential amino acids, additional supplements to promote favorable growth characteristics, e.g., trypsin, β-mercaptoethanol, and the like.

The engineered host cells can be cultured in conventional nutrient media modified as appropriate for activating promoters, selecting transformants, or amplifying the inserted polynucleotide sequences. The culture conditions, such as temperature, pH and the like, are typically those previously used with the particular host cell selected for expression, and will be apparent to those skilled in the art and in the references cited herein, including, e.g., Freshney (1994) *Culture of Animal Cells, a Manual of Basic Technique,* 3$^{rd}$ edition, Wiley-Liss, New York and the references cited therein. Other helpful references include, e.g., Paul (1975) *Cell and Tissue Culture,* 5$^{th}$ ed., Livingston, Edinburgh; Adams (1980) *Laboratory Techniques in Biochemistry and Molecular Biology-Cell Culture for Biochemists*, Work and Burdon (eds.) Elsevier, Amsterdam. Additional details regarding tissue culture procedures of particular interest in the production of influenza virus in vitro include, e.g., Merten et al. (1996) *Production of influenza virus in cell cultures for vaccine preparation*. in Cohen and Shafferman (eds.) *Novel Strategies in Design and Production of Vaccines*, which is incorporated herein in its entirety for all purposes. Additionally, variations in such procedures adapted to the present invention are readily determined through routine experimentation and will be familiar to those skilled in the art.

Cells for production of influenza virus (e.g., having the HA and/or NA sequences of the invention) can be cultured in serum-containing or serum free medium. In some case, e.g., for the preparation of purified viruses, it is typically desirable to grow the host cells in serum free conditions. Cells can be cultured in small scale, e.g., less than 25 ml medium, culture tubes or flasks or in large flasks with agitation, in rotator bottles, or on microcarrier beads (e.g., DEAE-Dextran microcarrier beads, such as Dormacell, Pfeifer & Langen; Superbead, Flow Laboratories; styrene copolymer-tri-methylamine beads, such as Hillex, SoloHill, Ann Arbor) in flasks, bottles or reactor cultures. Microcarrier beads are small spheres (in the range of 100-200 microns in diameter) that provide a large surface area for adherent cell growth per volume of cell culture. For example a single liter of medium can include more than 20 million microcarrier beads providing greater than 8000 square centimeters of growth surface. For commercial production of viruses, e.g., for vaccine production, it is often desirable to culture the cells in a bioreactor or fermenter. Bioreactors are available in volumes from under 1 liter to in excess of 100 liters, e.g., Cyto3 Bioreactor (Osmonics, Minnetonka, Minn.); NBS bioreactors (New Brunswick Scientific, Edison, N.J.); laboratory and commercial scale bioreactors from B. Braun Biotech International (B. Braun Biotech, Melsungen, Germany).

Regardless of the culture volume, in many desired aspects of the current invention, it is important that the cultures be maintained at an appropriate temperature, to insure efficient recovery of recombinant and/or reassortant influenza virus using temperature dependent multi plasmid systems (see, e.g., Multi-Plasmid System for the Production of Influenza Virus, U.S. Application No. 60/420,708, filed Oct. 23, 2002, U.S. application Ser. No. 10/423,828, filed Apr. 25, 2003, and U.S. Application No. 60/574,117, filed May 24, 2004), heating of virus solutions for filtration, etc. Typically, a regulator, e.g., a thermostat, or other device for sensing and maintaining the temperature of the cell culture system and/or other solution, is employed to insure that the temperature is at the correct level during the appropriate period (e.g., virus replication, etc.).

In some embodiments herein (e.g., wherein reasserted viruses are to be produced from segments on vectors) vectors comprising influenza genome segments are introduced (e.g., transfected) into host cells according to methods well known in the art for introducing heterologous nucleic acids into eukaryotic cells, including, e.g., calcium phosphate co-precipitation, electroporation, microinjection, lipofection, and transfection employing polyamine transfection reagents. For example, vectors, e.g., plasmids, can be transfected into host cells, such as COS cells, 293T cells or combinations of COS or 293T cells and MDCK cells, using the polyamine transfection reagent TransIT-LT1 (Mirus) according to the manufacturer's instructions in order to produce reasserted viruses, etc. Thus, in one example, approximately 1 μg of each vector is introduced into a population of host cells with approximately 2 μl of TransIT-LT1 diluted in 160 μl medium, preferably serum-free medium, in a total volume of 200 μl. The DNA:transfection reagent mixtures are incubated at room temperature for 45 minutes followed by addition of 800 μl of medium. The transfection mixture is added to the host cells, and the cells are cultured as described via other methods well known to those skilled in the art. Accordingly, for the production of recombinant or reassortant viruses in cell culture, vectors incorporating each of the 8 genome segments, (PB2, PB1, PA, NP, M, NS, HA and NA, e.g., of the invention) are mixed with approximately 20 μl TransIT-LT1 and transfected into host cells. Optionally, serum-containing medium is replaced prior to transfection with serum-free medium, e.g., Opti-MEM I, and incubated for 4-6 hours.

Alternatively, electroporation can be employed to introduce such vectors incorporating influenza genome segments into host cells. For example, plasmid vectors incorporating an influenza A or influenza B virus are favorably introduced into Vero cells using electroporation according to the following procedure. In brief, approximately $5\times10^6$ Vero cells, e.g., grown in Modified Eagle's Medium (MEM) supplemented with 10% Fetal Bovine Serum (FBS) are resuspended in 0.4 ml OptiMEM and placed in an electroporation cuvette. Twenty micrograms of DNA in a volume of up to 25 μl is added to the cells in the cuvette, which is then mixed gently by tapping. Electroporation is performed according to the manufacturer's instructions (e.g., BioRad Gene Pulser II with Capacitance Extender Plus connected) at 300 volts, 950 microFarads with a time constant of between 28-33 msec. The cells are remixed by gently tapping and approximately 1-2 minutes following electroporation 0.7 ml MEM with 10% FBS is added directly to the cuvette. The cells are then transferred to two wells of a standard 6 well tissue culture dish containing 2 ml MEM, 10% FBS. The cuvette is washed to recover any remaining cells and the wash suspension is divided between the two wells. Final volume is approximately 3.5 mL. The cells are then incubated under conditions permissive for viral growth, e.g., at approximately 33° C. for cold adapted strains.

In mammalian host cells, a number of expression systems, such as viral-based systems, can be utilized. In cases where an adenovirus is used as an expression vector, a coding sequence is optionally ligated into an adenovirus transcription/translation complex consisting of the late promoter and tripartite leader sequence. Insertion in a nonessential E1 or E3 region of the viral genome will result in a viable virus capable of expressing the polypeptides of interest in infected host cells (Logan and Shenk (1984) *Proc Natl Acad Sci* 81:3655-3659). In addition, transcription enhancers, such as the rous sarcoma virus (RSV) enhancer, can be used to increase expression in mammalian host cells.

A host cell strain is optionally chosen for its ability to modulate the expression of the inserted sequences or to process the expressed protein in the desired fashion. Such modifications of the protein include, but are not limited to, acetylation, carboxylation, glycosylation, phosphorylation, lipidation and acylation. Post-translational processing, which cleaves a precursor form into a mature form, of the protein is sometimes important for correct insertion, folding and/or function. Additionally proper location within a host cell (e.g., on the cell surface) is also important. Different host cells such as COS, CHO, BHK, MDCK, 293, 293T, COS7, etc. have specific cellular machinery and characteristic mechanisms for such post-translational activities and can be chosen to ensure the correct modification and processing of the current introduced, foreign protein.

For long-term, high-yield production of recombinant proteins encoded by, or having subsequences encoded by, the polynucleotides of the invention, stable expression systems are optionally used. For example, cell lines, stably expressing a polypeptide of the invention, are transfected using expression vectors that contain viral origins of replication or endogenous expression elements and a selectable marker gene. For example, following the introduction of the vector, cells are allowed to grow for 1-2 days in an enriched media before they are switched to selective media. The purpose of the selectable marker is to confer resistance to selection, and its presence allows growth and recovery of cells that successfully express the introduced sequences. Thus, resistant clumps of stably transformed cells, e.g., derived from single cell type, can be proliferated using tissue culture techniques appropriate to the cell type.

Host cells transformed with a nucleotide sequence encoding a polypeptide of the invention are optionally cultured under conditions suitable for the expression and recovery of the encoded protein from cell culture. The cells expressing said protein can be sorted, isolated and/or purified. The protein or fragment thereof produced by a recombinant cell can be secreted, membrane-bound, or retained intracellularly, depending on the sequence (e.g., depending upon fusion proteins encoding a membrane retention signal or the like) and/or the vector used.

Expression products corresponding to the nucleic acids of the invention can also be produced in non-animal cells such as plants, yeast, fungi, bacteria and the like. In addition to Sambrook, Berger and Ausubel, all infra, details regarding cell culture can be found in Payne et al. (1992) *Plant Cell and Tissue Culture in Liquid Systems* John Wiley & Sons, Inc. New York, N.Y.; Gamborg and Phillips (eds.) (1995) *Plant Cell, Tissue and Organ Culture*; Fundamental Methods Springer Lab Manual, Springer-Verlag (Berlin Heidelberg New York) and Atlas and Parks (eds.) *The Handbook of Microbiological Media* (1993) CRC Press, Boca Raton, Fla.

In bacterial systems, a number of expression vectors can be selected depending upon the use intended for the expressed product. For example, when large quantities of a polypeptide or fragments thereof are needed for the production of antibodies, vectors that direct high-level expression of fusion proteins that are readily purified are favorably employed. Such vectors include, but are not limited to, multifunctional *E. coli* cloning and expression vectors such as BLUESCRIPT (Stratagene), in which the coding sequence of interest, e.g., sequences comprising those found herein, etc., can be ligated into the vector in-frame with sequences for the amino-terminal translation initiating methionine and the subsequent 7 residues of beta-galactosidase producing a catalytically active beta galactosidase fusion protein; pIN vectors (Van Heeke & Schuster (1989) *J Biol Chem* 264:5503-5509); pET vectors (Novagen, Madison Wis.); and the like. Similarly, in the yeast *Saccharomyces cerevisiae* a number of vectors containing constitutive or inducible promoters such as alpha factor, alcohol oxidase and PGH can be used for production of the desired expression products. For reviews, see Ausubel, infra, and Grant et al., (1987); *Methods in Enzymology* 153: 516-544.

Nucleic Acid Hybridization

Comparative hybridization can be used to identify nucleic acids (e.g., SEQ ID NO: 1-10) of the invention, including conservative variations of nucleic acids of the invention. This comparative hybridization method is a preferred method of distinguishing nucleic acids of the invention. In addition, target nucleic acids which hybridize to the nucleic acids represented by, e.g., those shown herein under high, ultra-high and ultra-ultra-high stringency conditions are features of the invention. Examples of such nucleic acids include those with one or a few silent or conservative nucleic acid substitutions as compared to a given nucleic acid sequence.

A test target nucleic acid is said to specifically hybridize to a probe nucleic acid when it hybridizes at least one-half as well to the probe as to the perfectly matched complementary target, i.e., with a signal to noise ratio at least one-half as high as hybridization of the probe and target under conditions in which a perfectly matched probe binds to a perfectly matched complementary target with a signal to noise ratio that is at least about 5×-10× as high as that observed for hybridization to any of the unmatched target nucleic acids.

Nucleic acids "hybridize" when they associate, typically in solution. Nucleic acids hybridize due to a variety of well-characterized physico-chemical forces, such as hydrogen bonding, solvent exclusion, base stacking and the like. Numerous protocols for nucleic acid hybridization are well known in the art. An extensive guide to the hybridization of nucleic acids is found in Tijssen (1993) *Laboratory Techniques in Biochemistry and Molecular Biology—Hybridization with Nucleic Acid Probes* part I chapter 2, "Overview of principles of hybridization and the strategy of nucleic acid probe assays," (Elsevier, New York), as well as in Ausubel, Sambrook, and Berger and Kimmel, all below. Hames and Higgins (1995) *Gene Probes* 1 IRL Press at Oxford University Press, Oxford, England, (Hames and Higgins 1) and Hames and Higgins (1995) *Gene Probes* 2 IRL Press at Oxford University Press, Oxford, England (Hames and Higgins 2) provide details on the synthesis, labeling, detection and quantification of DNA and RNA, including oligonucleotides.

An example of stringent hybridization conditions for hybridization of complementary nucleic acids which have more than 100 complementary residues on a filter in a Southern or northern blot is 50% formalin with 1 mg of heparin at 42° C., with the hybridization being carried out overnight. An example of stringent wash conditions comprises a 0.2×SSC wash at 65° C. for 15 minutes (see, Sambrook, infra for a description of SSC buffer and other nucleic acid hybridization parameters). Often the high stringency wash is preceded by a low stringency wash to remove background probe signal. An example low stringency wash is 2×SSC at 40° C. for 15 minutes. In general, a signal to noise ratio of 5× (or higher) than that observed for an unrelated probe in the particular hybridization assay indicates detection of a specific hybridization.

After hybridization, unhybridized nucleic acids can be removed by a series of washes, the stringency of which can be adjusted depending upon the desired results. Low stringency washing conditions (e.g., using higher salt and lower temperature) increase sensitivity, but can produce nonspecific hybridization signals and high background signals. Higher stringency conditions (e.g., using lower salt and higher temperature that is closer to the $T_m$) lower the background signal, typically with primarily the specific signal remaining. See, also, Rapley, R. and Walker, J. M. eds., *Molecular Biomethods Handbook* (Humana Press, Inc. 1998).

"Stringent hybridization wash conditions" in the context of nucleic acid hybridization experiments such as Southern and northern hybridizations are sequence dependent, and are different under different environmental parameters. An extensive guide to the hybridization of nucleic acids is found in Tijssen (1993), supra, and in Hames and Higgins, 1 and 2. Stringent hybridization and wash conditions can easily be determined empirically for any test nucleic acid. For example, in determining highly stringent hybridization and wash conditions, the hybridization and wash conditions are gradually increased (e.g., by increasing temperature, decreasing salt concentration, increasing detergent concentration and/or increasing the concentration of organic solvents such as formalin in the hybridization or wash), until a selected set of criteria is met. For example, the hybridization and wash conditions are gradually increased until a probe binds to a perfectly matched complementary target with a signal to noise ratio that is at least 5× as high as that observed for hybridization of the probe to an unmatched target.

In general, a signal to noise ratio of at least 2× (or higher, e.g., at least 5×, 10×, 20×, 50×, 100×, or more) than that observed for an unrelated probe in the particular hybridization assay indicates detection of a specific hybridization. Detection of at least stringent hybridization between two sequences in the context of the present invention indicates relatively strong structural similarity to, e.g., the nucleic acids of the present invention provided in the sequence listings herein.

"Very stringent" conditions are selected to be equal to the thermal melting point ($T_m$) for a particular probe. The $T_m$ is the temperature (under defined ionic strength and pH) at which 50% of the test sequence hybridizes to a perfectly matched probe. For the purposes of the present invention, generally, "highly stringent" hybridization and wash conditions are selected to be about 5° C. lower than the $T_m$ for the specific sequence at a defined ionic strength and pH (as noted below, highly stringent conditions can also be referred to in comparative terms). Target sequences that are closely related or identical to the nucleotide sequence of interest (e.g., "probe") can be identified under stringent or highly stringent conditions. Lower stringency conditions are appropriate for sequences that are less complementary.

"Ultra high-stringency" hybridization and wash conditions are those in which the stringency of hybridization and wash conditions are increased until the signal to noise ratio for binding of a probe to a perfectly matched complementary target nucleic acid is at least 10× as high as that observed for hybridization to any unmatched target nucleic acids. A target nucleic acid which hybridizes to a probe under such conditions, with a signal to noise ratio of at least one-half that of the perfectly matched complementary target nucleic acid is said to bind to the probe under ultra-high stringency conditions.

In determining stringent or highly stringent hybridization (or even more stringent hybridization) and wash conditions, the hybridization and wash conditions are gradually increased (e.g., by increasing temperature, decreasing salt concentration, increasing detergent concentration and/or increasing the concentration of organic solvents, such as formamide, in the hybridization or wash), until a selected set of criteria are met. For example, the hybridization and wash conditions are gradually increased until a probe comprising one or more polynucleotide sequences of the invention, e.g., sequences or unique subsequences selected from those given herein (e.g., SEQ ID NO: 1-10) and/or complementary polynucleotide sequences, binds to a perfectly matched complementary target (again, a nucleic acid comprising one or more nucleic acid sequences or subsequences selected from those given herein and/or complementary polynucleotide sequences thereof), with a signal to noise ratio that is at least 2× (and optionally 5×, 10×, or 100× or more) as high as that observed for hybridization of the probe to an unmatched target (e.g., a polynucleotide sequence comprising one or more sequences or subsequences selected from known influenza sequences present in public databases such as GenBank at the time of filing, and/or complementary polynucleotide sequences thereof), as desired.

Using the polynucleotides of the invention, or subsequences thereof, novel target nucleic acids can be obtained; such target nucleic acids are also a feature of the invention. For example, such target nucleic acids include sequences that hybridize under stringent conditions to a unique oligonucleotide probe corresponding to any of the polynucleotides of the invention, e.g., SEQ ID NO: 1-10).

Similarly, even higher levels of stringency can be determined by gradually increasing the hybridization and/or wash conditions of the relevant hybridization assay. For example, those in which the stringency of hybridization and wash conditions are increased until the signal to noise ratio for binding of the probe to the perfectly matched complementary target nucleic acid is at least 10×, 20×, 50×, 100×, or 500× or more as high as that observed for hybridization to any unmatched target nucleic acids. The particular signal will depend on the label used in the relevant assay, e.g., a fluorescent label, a colorimetric label, a radioactive label, or the like. A target nucleic acid which hybridizes to a probe under such conditions, with a signal to noise ratio of at least one-half that of the perfectly matched complementary target nucleic acid is said to bind to the probe under ultra-ultra-high stringency conditions and are also features of the invention.

Nucleic acids that do not hybridize to each other under stringent conditions are still substantially identical if the polypeptides which they encode are substantially identical. This occurs, e.g., when a copy of a nucleic acid is created using the maximum codon degeneracy permitted by the genetic code.

Cloning, Mutagenesis and Expression of Biomolecules of Interest

General texts which describe molecular biological techniques, which are applicable to the present invention, such as cloning, mutation, cell culture and the like, include Berger and Kimmel, *Guide to Molecular Cloning Techniques, Methods in Enzymology* volume 152 Academic Press, Inc., San Diego, Calif. (Berger); Sambrook et al., *Molecular Cloning—A Laboratory Manual* (3rd Ed.), Vol. 1-3, Cold Spring Harbor Laboratory, Cold Spring Harbor, N.Y., 2000 ("Sambrook") and *Current Protocols in Molecular Biology*, F. M. Ausubel et al., eds., Current Protocols, a joint venture between Greene Publishing Associates, Inc. and John Wiley & Sons, Inc., (supplemented through 2002) ("Ausubel")). These texts describe mutagenesis, the use of vectors, promoters and many other relevant topics related to, e.g., the generation of HA and/or NA molecules, etc.

Various types of mutagenesis are optionally used in the present invention, e.g., to produce and/or isolate, e.g., novel or newly isolated HA and/or NA molecules and/or to further modify/mutate the polypeptides (e.g., HA and NA molecules as in SEQ ID NO: 11-20) of the invention. They include but are not limited to site-directed, random point mutagenesis, homologous recombination (DNA shuffling), mutagenesis using uracil containing templates, oligonucleotide-directed mutagenesis, phosphorothioate-modified DNA mutagenesis, mutagenesis using gapped duplex DNA or the like. Additional suitable methods include point mismatch repair, mutagenesis using repair-deficient host strains, restriction-selection and restriction-purification, deletion mutagenesis, mutagenesis by total gene synthesis, double-strand break repair, and the like. Mutagenesis, e.g., involving chimeric constructs, is also included in the present invention. In one embodiment, mutagenesis can be guided by known information of the naturally occurring molecule or altered or mutated naturally occurring molecule, e.g., sequence, sequence comparisons, physical properties, crystal structure or the like.

The above texts and examples found herein describe these procedures as well as the following publications (and references cited within): Sieber, et al., *Nature Biotechnology*, 19:456-460 (2001); Ling et al., *Approaches to DNA mutagenesis: an overview*, Anal Biochem 254(2): 157-178 (1997); Dale et al., *Oligonucleotide-directed random mutagenesis using the phosphorothioate method*, Methods Mol Biol 57:369-374 (1996); I. A. Lorimer, I. Pastan, *Nucleic Acids Res* 23, 3067-8 (1995); W. P. C. Stemmer, *Nature* 370, 389-91 (1994); Arnold, *Protein engineering for unusual environments*, Current Opinion in Biotechnology 4:450-455 (1993); Bass et al., *Mutant Trp repressors with new DNA-binding specificities*, Science 242:240-245 (1988); Fritz et al., *Oligonucleotide-directed construction of mutations: a gapped duplex DNA procedure without enzymatic reactions in vitro*, Nucl Acids Res 16: 6987-6999 (1988); Kramer et al., *Improved enzymatic in vitro reactions in the gapped duplex DNA approach to oligonucleotide-directed construction of mutations*, Nucl Acids Res 16: 7207 (1988); Sakamar and Khorana, *Total synthesis and expression of a gene for the a-subunit of bovine rod outer segment guanine nucleotide-binding protein (transducin)*, Nucl Acids Res 14: 6361-6372 (1988); Sayers et al., *Y-T Exonucleases in phosphorothioate-based oligonucleotide-directed mutagenesis*, Nucl Acids Res 16:791-802 (1988); Sayers et al., *Strand specific cleavage of phosphorothioate-containing DNA by reaction with restriction endonucleases in the presence of ethidium bromide*, (1988) Nucl Acids Res 16: 803-814; Carter, *Improved oligonucleotide-directed mutagenesis using M13 vectors*, Methods in Enzymol 154: 382-403 (1987); Kramer & Fritz *Oligonucleotide-directed construction of mutations via gapped duplex DNA*, Methods in Enzymol 154:350-367 (1987); Kunkel, *The efficiency of oligonucleotide directed mutagenesis*, in *Nucleic Acids & Molecular Biology* (Eckstein, F. and Lilley, D. M. J. eds., Springer Verlag, Berlin)) (1987); Kunkel et al., *Rapid and efficient site-specific mutagenesis without phenotypic selection*, Methods in Enzymol 154, 367-382 (1987); Zoller & Smith, *Oligonucleotide-directed mutagenesis: a simple method using two oligonucleotide primers and a single-stranded DNA template*, Methods in Enzymol 154:329-350 (1987); Carter, *Site-directed mutagenesis*, Biochem J 237:1-7 (1986); Eghtedarzadeh & Henikoff, *Use of oligonucleotides to generate large deletions*, Nucl Acids Res 14: 5115 (1986); Mandecki, *Oligonucleotide-directed double-strand break repair in plasmids of Escherichia coli: a method for site-specific mutagenesis*, Proc Natl Acad Sci USA, 83:7177-7181 (1986); Nakamaye & Eckstein, *Inhibition of restriction endonuclease Nci I cleavage by phosphorothioate groups and its application to oligonucleotide-directed mutagenesis*, Nucl Acids Res 14: 9679-9698 (1986); Wells et al., *Importance of hydrogen-bond formation in stabilizing the transition state of subtilisin*, Phil Trans R Soc Lond A 317: 415-423 (1986); Botstein & Shortle, *Strategies and applications of in vitro mutagenesis*, Science 229:1193-1201 (1985); Carter et al., *Improved oligonucleotide site-directed mutagenesis using M13 vectors*, Nucl Acids Res 13: 4431-4443 (1985); Grundström et al., *Oligonucleotide-directed mutagenesis by microscale 'shot-gun' gene synthesis*, Nucl Acids Res 13: 3305-3316 (1985); Kunkel, *Rapid and efficient site-specific mutagenesis without phenotypic selection*, Proc Natl Acad Sci USA 82:488-492 (1985); Smith, *In vitro mutagenesis*, Ann Rev Genet. 19:423-462 (1985); Taylor et al., *The use of phosphorothioate-modified DNA in restriction enzyme reactions to prepare nicked DNA*, Nucl Acids Res 13: 8749-8764 (1985); Taylor et al., *The rapid generation of oligonucleotide-directed mutations at high frequency using phosphorothioate-modified DNA*, Nucl Acids Res 13: 8765-8787 (1985); Wells et al., *Cassette mutagenesis: an efficient method for generation of multiple mutations at defined sites*, Gene 34:315-323 (1985); Kramer et al., *The gapped duplex DNA approach to oligonucleotide-directed mutation construction*, Nucl Acids Res 12: 9441-9456 (1984); Kramer et al., *Point Mismatch Repair*, Cell 38:879-887 (1984); Nambiar et al., *Total synthesis and cloning of a gene coding for the ribonuclease S protein*, Science 223: 1299-1301 (1984); Zoller & Smith, *Oligonucleotide-directed mutagenesis of DNA fragments cloned into M13 vectors*, Methods in Enzymol 100: 468-500 (1983); and Zoller & Smith, *Oligonucleotide-directed mutagenesis using M13-derived vectors: an efficient and general procedure for the production of point mutations in any DNA fragment*, Nucl Acids Res 10:6487-6500 (1982).

Additional details on many of the above methods can be found in *Methods in Enzymol* Volume 154, which also describes useful controls for trouble-shooting problems with various mutagenesis, gene isolation, expression, and other methods.

Oligonucleotides, e.g., for use in mutagenesis of the present invention, e.g., mutating libraries of the HA and/or NA molecules of the invention, or altering such, are typically synthesized chemically according to the solid phase phosphoramidite triester method described by Beaucage and Caruthers, *Tetrahedron Letts* 22(20):1859-1862, (1981) e.g., using an automated synthesizer, as described in Needham-VanDevanter et al., *Nucleic Acids Res,* 12:6159-6168 (1984).

In addition, essentially any nucleic acid can be custom or standard ordered from any of a variety of commercial sources, such as The Midland Certified Reagent Company (mcrc@oligos.com), The Great American Gene Company (www.genco.com), ExpressGen Inc. (www.expressgen.com), Operon Technologies Inc. (Alameda, Calif.) and many others. Similarly, peptides and antibodies can be custom ordered from any of a variety of sources, such as PeptidoGenic (available at pkim@ccnet.com), HTI Bio-products, Inc. (www.htibio.com), BMA Biomedicals Ltd. (U.K.), Bio-Synthesis, Inc., and many others.

The present invention also relates to host cells and organisms comprising a HA and/or NA molecule or other polypeptide and/or nucleic acid of the invention, e.g., SEQ ID NO:1-20. Host cells are genetically engineered (e.g., transformed, transduced or transfected) with the vectors of this invention, which can be, for example, a cloning vector or an expression vector. The vector can be, for example, in the form of a plasmid, a bacterium, a virus, a naked polynucleotide, or a conjugated polynucleotide. The vectors are introduced into cells and/or microorganisms by standard methods including electroporation (see, From et al., *Proc Natl Acad Sci USA* 82, 5824 (1985), infection by viral vectors, high velocity ballistic penetration by small particles with the nucleic acid either within the matrix of small beads or particles, or on the surface (Klein et al., *Nature* 327, 70-73 (1987)). Berger, Sambrook, and Ausubel provide a variety of appropriate transformation methods. See, above.

Several well-known methods of introducing target nucleic acids into bacterial cells are available, any of which can be used in the present invention. These include: fusion of the recipient cells with bacterial protoplasts containing the DNA, electroporation, projectile bombardment, and infection with viral vectors, etc. Bacterial cells can be used to amplify the number of plasmids containing DNA constructs of this invention. The bacteria are grown to log phase and the plasmids within the bacteria can be isolated by a variety of methods known in the art (see, for instance, Sambrook). In addition, a plethora of kits are commercially available for the purification of plasmids from bacteria, (see, e.g., EasyPrep™, FlexiPrep™, both from Pharmacia Biotech; StrataClean™, from Stratagene; and, QIAprep™ from Qiagen). The isolated and purified plasmids are then further manipulated to produce other plasmids, used to transfect cells or incorporated into related vectors to infect organisms. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Vectors are suitable for replication and integration in prokaryotes, eukaryotes, or optionally both. See, Giliman & Smith, *Gene* 8:81 (1979); Roberts, et al., *Nature,* 328:731 (1987); Schneider, B., et al., *Protein Exr Purif* 6435:10 (1995); Ausubel, Sambrook, Berger (all supra). A catalogue of Bacteria and Bacteriophages useful for cloning is provided, e.g., by the ATCC, e.g., *The ATCC Catalogue of Bacteria and Bacteriophage* (1992) Gherna et al. (eds.) published by the ATCC. Additional basic procedures for sequencing, cloning and other aspects of molecular biology and underlying theoretical considerations are also found in Watson et al. (1992) *Recombinant DNA Second Edition* Scientific American Books, NY. See, above. Further vectors useful with the sequences herein are illustrated above in the section concerning production of influenza virus for vaccines and the references cited therein.

Polypeptide Production and Recovery

Following transduction of a suitable host cell line or strain and growth of the host cells to an appropriate cell density, the selected promoter is induced by appropriate means (e.g., temperature shift or chemical induction) and cells are cultured for an additional period. In some embodiments, a secreted polypeptide product, e.g., a HA and/or NA polypeptide as in a secreted fusion protein form, etc., is then recovered from the culture medium. In other embodiments, a virus particle containing a HA and/or a NA polypeptide of the invention is produced from the cell. Alternatively, cells can be harvested by centrifugation, disrupted by physical or chemical means, and the resulting crude extract retained for further purification. Eukaryotic or microbial cells employed in expression of proteins can be disrupted by any convenient method, including freeze-thaw cycling, sonication, mechanical disruption, or use of cell lysing agents, or other methods, which are well know to those skilled in the art. Additionally, cells expressing a HA and/or a NA polypeptide product of the invention can be utilized without separating the polypeptide from the cell. In such situations, the polypeptide of the invention is optionally expressed on the cell surface and is examined thus (e.g., by having HA and/or NA molecules (or fragments thereof, e.g., comprising fusion proteins or the like) on the cell surface bind antibodies, etc. Such cells are also features of the invention.

Expressed polypeptides can be recovered and purified from recombinant cell cultures by any of a number of methods well known in the art, including ammonium sulfate or ethanol precipitation, acid extraction, anion or cation exchange chromatography, phosphocellulose chromatography, hydrophobic interaction chromatography, affinity chromatography (e.g., using any of the tagging systems known to those skilled in the art), hydroxylapatite chromatography, and lectin chromatography. Protein refolding steps can be used, as desired, in completing configuration of the mature protein. Also, high performance liquid chromatography (HPLC) can be employed in the final purification steps. In addition to the references noted herein, a variety of purification methods are well known in the art, including, e.g., those set forth in Sandana (1997) *Bioseparation of Proteins*, Academic Press, Inc.; and Bollag et al. (1996) *Protein Methods, 2$^{nd}$ Edition* Wiley-Liss, NY; Walker (1996) *The Protein Protocols Handbook* Humana Press, NJ, Harris and Angal (1990) *Protein Purification Applications: A Practical Approach* IRL Press at Oxford, Oxford, England; Harris and Angal *Protein Purification Methods: A Practical Approach* IRL Press at Oxford, Oxford, England; Scopes (1993) *Protein Purification: Principles and Practice* 3$^{rd}$ *Edition* Springer Verlag, NY; Janson and Ryden (1998) *Protein Purification: Principles, High*

*Resolution Methods and Applications, Second Edition* Wiley-VCH, NY; and Walker (1998) *Protein Protocols on CD-ROM* Humana Press, NJ.

When the expressed polypeptides of the invention are produced in viruses, the viruses are typically recovered from the culture medium, in which infected (transfected) cells have been grown. Typically, crude medium is clarified prior to concentration of influenza viruses. Common methods include ultrafiltration, adsorption on barium sulfate and elution, and centrifugation. For example, crude medium from infected cultures can first be clarified by centrifugation at, e.g., 1000-2000×g for a time sufficient to remove cell debris and other large particulate matter, e.g., between 10 and 30 minutes. Optionally, the clarified medium supernatant is then centrifuged to pellet the influenza viruses, e.g., at 15,000×g, for approximately 3-5 hours. Following resuspension of the virus pellet in an appropriate buffer, such as STE (0.01 M Tris-HCl; 0.15 M NaCl; 0.0001 M EDTA) or phosphate buffered saline (PBS) at pH 7.4, the virus is concentrated by density gradient centrifugation on sucrose (60%-12%) or potassium tartrate (50%-10%). Either continuous or step gradients, e.g., a sucrose gradient between 12% and 60% in four 12% steps, are suitable. The gradients are centrifuged at a speed, and for a time, sufficient for the viruses to concentrate into a visible band for recovery. Alternatively, and for most large-scale commercial applications, virus is elutriated from density gradients using a zonal-centrifuge rotor operating in continuous mode. Additional details sufficient to guide one of skill through the preparation of influenza viruses from tissue culture are provided, e.g., in Furminger. *Vaccine Production*, in Nicholson et al. (eds.) *Textbook of Influenza* pp. 324-332; Merten et al. (1996) *Production of influenza virus in cell cultures for vaccine preparation*, in Cohen & Shafferman (eds.) *Novel Strategies in Design and Production of Vaccines* pp. 141-151, and U.S. Pat. No. 5,690,937. If desired, the recovered viruses can be stored at −80° C. in the presence of sucrose-phosphate-glutamate (SPG) as a stabilizer Alternatively, cell-free transcription/translation systems can be employed to produce polypeptides comprising an amino acid sequence or subsequence of, e.g., the sequences given herein such as SEQ ID NO: 11-20, or encoded by the polynucleotide sequences of the invention, e.g., SEQ ID NO: 1-10. A number of suitable in vitro transcription and translation systems are commercially available. A general guide to in vitro transcription and translation protocols is found in Tymms (1995) *In vitro Transcription and Translation Protocols: Methods in Molecular Biology* Volume 37, Garland Publishing, NY.

In addition, the polypeptides, or subsequences thereof, e.g., subsequences comprising antigenic peptides, can be produced manually or by using an automated system, by direct peptide synthesis using solid-phase techniques (see, Stewart et al. (1969) *Solid-Phase Peptide Synthesis*, WH Freeman Co, San Francisco; Merrifield J (1963) *J Am Chem Soc* 85:2149-2154). Exemplary automated systems include the Applied Biosystems 431A Peptide Synthesizer (Perkin Elmer, Foster City, Calif.). If desired, subsequences can be chemically synthesized separately, and combined using chemical methods to provide full-length polypeptides.

Modified Amino Acids

Expressed polypeptides of the invention can contain one or more modified amino acids. The presence of modified amino acids can be advantageous in, for example, (a) increasing polypeptide serum half-life, (b) reducing/increasing polypeptide antigenicity, (c) increasing polypeptide storage stability, etc. Amino acid(s) are modified, for example, co-translationally or post-translationally during recombinant production (e.g., N-linked glycosylation at N—X—S/T motifs during expression in mammalian cells) or modified by synthetic means (e.g., via PEGylation).

Non-limiting examples of a modified amino acid include a glycosylated amino acid, a sulfated amino acid, a prenylated (e.g., farnesylated, geranylgeranylated) amino acid, an acetylated amino acid, an acylated amino acid, a PEG-ylated amino acid, a biotinylated amino acid, a carboxylated amino acid, a phosphorylated amino acid, and the like, as well as amino acids modified by conjugation to, e.g., lipid moieties or other organic derivatizing agents. References adequate to guide one of skill in the modification of amino acids are replete throughout the literature. Example protocols are found in Walker (1998) *Protein Protocols on CD-ROM* Human Press, Towata, N.J.

Fusion Proteins

The present invention also provides fusion proteins comprising fusions of the sequences of the invention (e.g., encoding HA and/or NA polypeptides as exampled by SEQ ID NO: 11-20) or fragments thereof with, e.g., immunoglobulins (or portions thereof), sequences encoding, e.g., GFP (green fluorescent protein), or other similar markers, etc. Nucleotide sequences encoding such fusion proteins are another aspect of the invention. Fusion proteins of the invention are optionally used for, e.g., similar applications (including, e.g., therapeutic, prophylactic, diagnostic, experimental, etc. applications as described herein) as the non-fusion proteins of the invention. In addition to fusion with immunoglobulin sequences and marker sequences, the proteins of the invention are also optionally fused with, e.g., sequences which allow sorting of the fusion proteins and/or targeting of the fusion proteins to specific cell types, regions, etc.

Antibodies

The polypeptides of the invention can be used to produce antibodies specific for the polypeptides given herein and/or polypeptides encoded by the polynucleotides of the invention, e.g., those shown herein, and conservative variants thereof. Antibodies specific for the above mentioned polypeptides are useful, e.g., for diagnostic and therapeutic purposes, e.g., related to the activity, distribution, and expression of target polypeptides.

Antibodies specific for the polypeptides of the invention can be generated by methods well known in the art. Such antibodies can include, but are not limited to, polyclonal, monoclonal, chimeric, humanized, single chain, Fab fragments and fragments produced by an Fab expression library.

Polypeptides do not require biological activity for antibody production (e.g., full length functional hemagglutinin or neuraminidase is not required). However, the polypeptide or oligopeptide must be antigenic. Peptides used to induce specific antibodies typically have an amino acid sequence of at least about 4 amino acids, and often at least 5 or 10 amino acids. Short stretches of a polypeptide can be fused with another protein, such as keyhole limpet hemocyanin, and antibody produced against the chimeric molecule.

Numerous methods for producing polyclonal and monoclonal antibodies are known to those of skill in the art, and can be adapted to produce antibodies specific for the polypeptides of the invention, and/or encoded by the polynucleotide sequences of the invention, etc. See, e.g., Coligan (1991) *Current Protocols in Immunology* Wiley/Greene, NY; Paul (ed.) (1998) *Fundamental Immunology, Fourth Edition*, Lippincott-Raven, Lippincott Williams & Wilkins; Harlow and Lane (1989) *Antibodies: A Laboratory Manual* Cold Spring Harbor Press, NY; Stites et al. (eds.) *Basic and Clinical Immunology* (4th ed.) Lange Medical Publications, Los Altos, Calif., and references cited therein; Goding (1986)

*Monoclonal Antibodies: Principles and Practice* (2d ed.) Academic Press, New York, N.Y.; and Kohler and Milstein (1975) *Nature* 256: 495-497. Other suitable techniques for antibody preparation include selection of libraries of recombinant antibodies in phage or similar vectors. See, Huse et al. (1989) *Science* 246: 1275-1281; and Ward, et al. (1989) *Nature* 341: 544-546. Specific monoclonal and polyclonal antibodies and antisera will usually bind with a $K_D$ of, e.g., at least about 0.1 µM, at least about 0.01 µM or better, and, typically and at least about 0.001 µM or better.

For certain therapeutic applications, humanized antibodies are desirable. Detailed methods for preparation of chimeric (humanized) antibodies can be found in U.S. Pat. No. 5,482, 856. Additional details on humanization and other antibody production and engineering techniques can be found in Borrebaeck (ed.) (1995) *Antibody Engineering, 2nd Edition* Freeman and Company, NY (Borrebaeck); McCafferty et al. (1996) *Antibody Engineering, A Practical Approach* IRL at Oxford Press, Oxford, England (McCafferty), and Paul (1995) *Antibody Engineering Protocols* Humana Press, Towata, N.J. (Paul). Additional details regarding specific procedures can be found, e.g., in Ostberg et al. (1983), *Hybridoma* 2: 361-367, Ostberg, U.S. Pat. No. 4,634,664, and Engelman et al., U.S. Pat. No. 4,634,666.

Defining Polypeptides by Immunoreactivity

Because the polypeptides of the invention provide a variety of new polypeptide sequences (e.g., comprising HA and NA molecules), the polypeptides also provide new structural features which can be recognized, e.g., in immunological assays. The generation of antisera which specifically bind the polypeptides of the invention, as well as the polypeptides which are bound by such antisera, are features of the invention.

For example, the invention includes polypeptides (e.g., HA and NA molecules) that specifically bind to or that are specifically immunoreactive with an antibody or antisera generated against an immunogen comprising an amino acid sequence selected from one or more of the sequences given herein (e.g., SEQ ID NO: 11-20), etc. To eliminate cross-reactivity with other homologues, the antibody or antisera is subtracted with the HA and/or NA molecules found in public databases at the time of filing, e.g., the "control" polypeptide (s). Where the other control sequences correspond to a nucleic acid, a polypeptide encoded by the nucleic acid is generated and used for antibody/antisera subtraction purposes.

In one typical format, the immunoassay uses a polyclonal antiserum which was raised against one or more polypeptide comprising one or more of the sequences corresponding to the sequences herein (e.g., SEQ ID NO: 11-20), etc. or a substantial subsequence thereof (i.e., at least about 30% of the full length sequence provided). The set of potential polypeptide immunogens derived from the present sequences are collectively referred to below as "the immunogenic polypeptides." The resulting antisera is optionally selected to have low cross-reactivity against the control hemagglutinin and/or neuraminidase homologues and any such cross-reactivity is removed, e.g., by immunoabsorbtion, with one or more of the control hemagglutinin and neuraminidase homologues, prior to use of the polyclonal antiserum in the immunoassay.

In order to produce antisera for use in an immunoassay, one or more of the immunogenic polypeptides is produced and purified as described herein. For example, recombinant protein can be produced in a recombinant cell. An inbred strain of mice (used in this assay because results are more reproducible due to the virtual genetic identity of the mice) is immunized with the immunogenic protein(s) in combination with a standard adjuvant, such as Freund's adjuvant, and a standard mouse immunization protocol (see, e.g., Harlow and Lane (1988) *Antibodies, A Laboratory Manual*, Cold Spring Harbor Publications, New York, for a standard description of antibody generation, immunoassay formats and conditions that can be used to determine specific immunoreactivity). Additional references and discussion of antibodies is also found herein and can be applied here to defining polypeptides by immunoreactivity. Alternatively, one or more synthetic or recombinant polypeptide derived from the sequences disclosed herein is conjugated to a carrier protein and used as an immunogen.

Polyclonal sera are collected and titered against the immunogenic polypeptide in an immunoassay, for example, a solid phase immunoassay with one or more of the immunogenic proteins immobilized on a solid support. Polyclonal antisera with a titer of $10^6$ or greater are selected, pooled and subtracted with the control hemagglutinin and/or neuraminidase polypeptide(s) to produce subtracted pooled titered polyclonal antisera.

The subtracted pooled titered polyclonal antisera are tested for cross reactivity against the control homologue(s) in a comparative immunoassay. In this comparative assay, discriminatory binding conditions are determined for the subtracted titered polyclonal antisera which result in at least about a 5-10 fold higher signal to noise ratio for binding of the titered polyclonal antisera to the immunogenic polypeptides as compared to binding to the control homologues. That is, the stringency of the binding reaction is adjusted by the addition of non-specific competitors such as albumin or non-fat dry milk, and/or by adjusting salt conditions, temperature, and/or the like. These binding conditions are used in subsequent assays for determining whether a test polypeptide (a polypeptide being compared to the immunogenic polypeptides and/or the control polypeptides) is specifically bound by the pooled subtracted polyclonal antisera. In particular, test polypeptides which show at least a 2-5× higher signal to noise ratio than the control receptor homologues under discriminatory binding conditions, and at least about a ½ signal to noise ratio as compared to the immunogenic polypeptide(s), shares substantial structural similarity with the immunogenic polypeptide as compared to the known receptor, etc., and is, therefore a polypeptide of the invention.

In another example, immunoassays in the competitive binding format are used for detection of a test polypeptide. For example, as noted, cross-reacting antibodies are removed from the pooled antisera mixture by immunoabsorption with the control polypeptides. The immunogenic polypeptide(s) are then immobilized to a solid support which is exposed to the subtracted pooled antisera. Test proteins are added to the assay to compete for binding to the pooled subtracted antisera. The ability of the test protein(s) to compete for binding to the pooled subtracted antisera as compared to the immobilized protein(s) is compared to the ability of the immunogenic polypeptide(s) added to the assay to compete for binding (the immunogenic polypeptides compete effectively with the immobilized immunogenic polypeptides for binding to the pooled antisera). The percent cross-reactivity for the test proteins is calculated, using standard calculations.

In a parallel assay, the ability of the control protein(s) to compete for binding to the pooled subtracted antisera is optionally determined as compared to the ability of the immunogenic polypeptide(s) to compete for binding to the antisera. Again, the percent cross-reactivity for the control polypeptide (s) is calculated, using standard calculations. Where the percent cross-reactivity is at least 5-10× as high for the test polypeptides as compared to the control polypeptide(s) and or where the binding of the test polypeptides is approximately in the range of the binding of the immunogenic polypeptides, the test polypeptides are said to specifically bind the pooled subtracted antisera.

In general, the immunoabsorbed and pooled antisera can be used in a competitive binding immunoassay as described herein to compare any test polypeptide to the immunogenic and/or control polypeptide(s). In order to make this comparison, the immunogenic, test and control polypeptides are each assayed at a wide range of concentrations and the amount of each polypeptide required to inhibit 50% of the binding of the subtracted antisera to, e.g., an immobilized control, test or immunogenic protein is determined using standard techniques. If the amount of the test polypeptide required for binding in the competitive assay is less than twice the amount of the immunogenic polypeptide that is required, then the test polypeptide is said to specifically bind to an antibody generated to the immunogenic protein, provided the amount is at least about 5-10× as high as for the control polypeptide.

As an additional determination of specificity, the pooled antisera is optionally fully immunosorbed with the immunogenic polypeptide(s) (rather than the control polypeptide(s)) until little or no binding of the resulting immunogenic polypeptide subtracted pooled antisera to the immunogenic polypeptide(s) used in the immunosorbtion is detectable. This fully immunosorbed antisera is then tested for reactivity with the test polypeptide. If little or no reactivity is observed (i.e., no more than 2× the signal to noise ratio observed for binding of the fully immunosorbed antisera to the immunogenic polypeptide), then the test polypeptide is specifically bound by the antisera elicited by the immunogenic protein.

Nucleic Acid and Polypeptide Sequence Variants

As described herein, the invention provides for nucleic acid polynucleotide sequences and polypeptide amino acid sequences, e.g., hemagglutinin and neuraminidase sequences, and, e.g., compositions and methods comprising said sequences. Examples of said sequences are disclosed herein (e.g., SEQ ID NO: 1-20). However, one of skill in the art will appreciate that the invention is not necessarily limited to those sequences disclosed herein and that the present invention also provides many related and unrelated sequences with the functions described herein, e.g., encoding a HA and/or a NA molecule.

One of skill will also appreciate that many variants of the disclosed sequences are included in the invention. For example, conservative variations of the disclosed sequences that yield a functionally identical sequence are included in the invention. Variants of the nucleic acid polynucleotide sequences, wherein the variants hybridize to at least one disclosed sequence, are considered to be included in the invention. Unique subsequences of the sequences disclosed herein, as determined by, e.g., standard sequence comparison techniques, are also included in the invention.

Silent Variations

Due to the degeneracy of the genetic code, any of a variety of nucleic acid sequences encoding polypeptides and/or viruses of the invention are optionally produced, some which can bear lower levels of sequence identity to the HA and NA nucleic acid and polypeptide sequences herein. The following provides a typical codon table specifying the genetic code, found in many biology and biochemistry texts.

TABLE 1

Codon Table

| Amino acids | | | Codon |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

The codon table shows that many amino acids are encoded by more than one codon. For example, the codons AGA, AGG, CGA, CGC, CGG, and CGU all encode the amino acid arginine. Thus, at every position in the nucleic acids of the invention where an arginine is specified by a codon, the codon can be altered to any of the corresponding codons described above without altering the encoded polypeptide. It is understood that U in an RNA sequence corresponds to T in a DNA sequence.

Such "silent variations" are one species of "conservatively modified variations," discussed below. One of skill will recognize that each codon in a nucleic acid (except ATG, which is ordinarily the only codon for methionine, and TTG, which is ordinarily the only codon for tryptophan) can be modified by standard techniques to encode a functionally identical polypeptide. Accordingly, each silent variation of a nucleic acid which encodes a polypeptide is implicit in any described sequence. The invention, therefore, explicitly provides each and every possible variation of a nucleic acid sequence encoding a polypeptide of the invention that could be made by selecting combinations based on possible codon choices. These combinations are made in accordance with the standard triplet genetic code (e.g., as set forth in Table 1, or as is commonly available in the art) as applied to the nucleic acid sequence encoding a hemagglutinin or a neuraminidase polypeptide of the invention. All such variations of every nucleic acid herein are specifically provided and described by consideration of the sequence in combination with the genetic code. One of skill is fully able to make these silent substitutions using the methods herein.

Conservative Variations

Owing to the degeneracy of the genetic code, "silent substitutions" (i.e., substitutions in a nucleic acid sequence which do not result in an alteration in an encoded polypeptide) are an implied feature of every nucleic acid sequence of the invention which encodes an amino acid. Similarly, "conservative amino acid substitutions," in one or a few amino acids in an amino acid sequence are substituted with different amino acids with highly similar properties, are also readily identified as being highly similar to a disclosed construct such as those herein. Such conservative variations of each disclosed sequence are a feature of the present invention.

"Conservative variations" of a particular nucleic acid sequence refers to those nucleic acids which encode identical or essentially identical amino acid sequences, or, where the nucleic acid does not encode an amino acid sequence, to essentially identical sequences, see, Table 2 below. One of skill will recognize that individual substitutions, deletions or additions which alter, add or delete a single amino acid or a small percentage of amino acids (typically less than 5%, more typically less than 4%, 3%, 2% or 1%) in an encoded sequence are "conservatively modified variations" where the alterations result in the deletion of an amino acid, addition of an amino acid, or substitution of an amino acid with a chemically similar amino acid. Thus, "conservative variations" of a listed polypeptide sequence of the present invention include substitutions of a small percentage, typically less than 5%, more typically less than 4%, 3%, 2% or 1%, of the amino acids of the polypeptide sequence, with a conservatively selected amino acid of the same conservative substitution group. Finally, the addition of sequences which do not alter the encoded activity of a nucleic acid molecule, such as the addition of a non-functional sequence, is a conservative variation of the basic nucleic acid.

TABLE 2

Conservative Substitution Groups

| 1 | Alanine (A) | Serine (S) | Threonine (T) | |
|---|---|---|---|---|
| 2 | Aspartic acid (D) | Glutamic acid (E) | | |
| 3 | Asparagine (N) | Glutamine (Q) | | |
| 4 | Arginine (R) | Lysine (K) | | |
| 5 | Isoleucine (I) | Leucine (L) | Methionine (M) | Valine (V) |
| 6 | Phenylalanine (F) | Tyrosine (Y) | Tryptophan (W) | |

Unique Polypeptide and Polynucleotide Subsequences

In one aspect, the invention provides a nucleic acid which comprises a unique subsequence in a nucleic acid selected from the sequence of HA and NA molecules disclosed herein, e.g., SEQ ID NO: 1-10. The unique subsequence is unique as compared to a nucleic acids corresponding to nucleic acids such as, e.g., those found in GenBank or other similar public databases at the time of filing. Alignment can be performed using, e.g., BLAST set to default parameters. Any unique subsequence is useful, e.g., as a probe to identify the nucleic acids of the invention. See, above.

Similarly, the invention includes a polypeptide which comprises a unique subsequence in a polypeptide selected from the sequence of HA and NA molecules disclosed herein, e.g., SEQ ID NO: 11-20. Here, the unique subsequence is unique as compared to a polypeptide corresponding to, e.g., the amino acid corresponding to polynucleotide sequences found in, e.g., GenBank or other similar public databases at the time of filing.

The invention also provides for target nucleic acids which hybridize under stringent conditions to a unique coding oligonucleotide which encodes a unique subsequence in a polypeptide selected from the sequences of HA and NA molecules of the invention wherein the unique subsequence is unique as compared to a polypeptide corresponding to any of the control polypeptides (sequences of, e.g., the nucleic acids corresponding to those found in, e.g., GenBank or other similar public databases at the time of filing). Unique sequences are determined as noted above.

Sequence Comparison Identity and Homology

The terms "identical" or percent "identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described below (or other algorithms available to persons of skill) or by visual inspection.

The phrase "substantially identical," in the context of two nucleic acids or polypeptides (e.g., DNAs encoding a HA or NA molecule, or the amino acid sequence of a HA or NA molecule) refers to two or more sequences or subsequences that have at least about 90%, preferably 91%, most preferably 92%, 93%, 94%, 95%, 96%, 97%, 98%, 98.5%, 99%, 99.1%, 99.2%, 99.3%, 99.4%, 99.5%, 99.6%, 99.7%, 99.8%, 99.9% or more nucleotide or amino acid residue identity, when compared and aligned for maximum correspondence, as measured using a sequence comparison algorithm or by visual inspection. Such "substantially identical" sequences are typically considered to be "homologous," without reference to actual ancestry. Preferably, "substantial identity" exists over a region of the amino acid sequences that is at least about 200 residues in length, more preferably over a region of at least about 250 residues, and most preferably the sequences are substantially identical over at least about 300 residues, 350 residues, 400 residues, 425 residues, 450 residues, 475 residues, 480 residues, 490 residues, 495 residues, 499 residues, 500 residues, 502 residues, 559 residues, 565 residues, or 566 residues, or over the full length of the two sequences to be compared.

For sequence comparison and homology determination, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv Appl Math* 2:482 (1981), by the homology alignment algorithm of Needleman & Wunsch, *J Mol Biol* 48:443 (1970), by the search for similarity method of Pearson & Lipman, *Proc Natl Acad Sci USA* 85:2444 (1988), by computerized implementations of algorithms such as GAP, BESTFIT, FASTA, and TFASTA in the Wisconsin Genetics Software Package, Genetics Computer Group, 575 Science Dr., Madison, Wis., or by visual inspection (see generally, Ausubel et al., supra).

One example of an algorithm that is suitable for determining percent sequence identity and sequence similarity is the BLAST algorithm, which is described in Altschul et al., *J Mol Biol* 215:403-410 (1990). Software for performing BLAST analyses is publicly available through the National Center for Biotechnology Information (www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (see, Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see, Henikoff & Henikoff (1989) *Proc Natl Acad Sci USA* 89:10915).

In addition to calculating percent sequence identity, the BLAST algorithm also performs a statistical analysis of the similarity between two sequences (see, e.g., Karlin & Altschul, *Proc Natl Acad Sci USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Another example of a useful sequence alignment algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle (1987) *J. Mol. Evol.* 35:351-360. The method used is similar to the method described by Higgins & Sharp (1989) *CABIOS* 5:151-153. The program can align, e.g., up to 300 sequences of a maximum length of 5,000 letters. The multiple alignment procedure begins with the pairwise alignment of the two most similar sequences, producing a cluster of two aligned sequences. This cluster can then be aligned to the next most related sequence or cluster of aligned sequences. Two clusters of sequences can be aligned by a simple extension of the pairwise alignment of two individual sequences. The final alignment is achieved by a series of progressive, pairwise alignments. The program can also be used to plot a dendogram or tree representation of clustering relationships. The program is run by designating specific sequences and their amino acid or nucleotide coordinates for regions of sequence comparison.

An additional example of an algorithm that is suitable for multiple DNA, or amino acid, sequence alignments is the CLUSTALW program (Thompson, J. D. et al. (1994) *Nucl. Acids. Res.* 22: 4673-4680). CLUSTALW performs multiple pairwise comparisons between groups of sequences and assembles them into a multiple alignment based on homology. Gap open and Gap extension penalties can be, e.g., 10 and 0.05 respectively. For amino acid alignments, the BLOSUM algorithm can be used as a protein weight matrix. See, e.g., Henikoff and Henikoff (1992) *Proc. Natl. Acad. Sci. USA* 89: 10915-10919.

Digital Systems

The present invention provides digital systems, e.g., computers, computer readable media and integrated systems comprising character strings corresponding to the sequence information herein for the nucleic acids and isolated or recombinant polypeptides herein, including, e.g., the sequences shown herein, and the various silent substitutions and conservative substitutions thereof. Integrated systems can further include, e.g., gene synthesis equipment for making genes corresponding to the character strings.

Various methods known in the art can be used to detect homology or similarity between different character strings (see, above), or can be used to perform other desirable functions such as to control output files, provide the basis for making presentations of information including the sequences and the like. Examples include BLAST, discussed supra. Computer systems of the invention can include such programs, e.g., in conjunction with one or more data file or data base comprising a sequence as noted herein.

Thus, different types of homology and similarity of various stringency and length between various HA or NA sequences or fragments, etc. can be detected and recognized in the integrated systems herein. For example, many homology determination methods have been designed for comparative analysis of sequences of biopolymers, for spell-checking in word processing, and for data retrieval from various databases. With an understanding of double-helix pair-wise complement interactions among 4 principal nucleobases in natural polynucleotides, models that simulate annealing of complementary homologous polynucleotide strings can also be used as a foundation of sequence alignment or other operations typically performed on the character strings corresponding to the sequences herein (e.g., word-processing manipulations, construction of figures comprising sequence or subsequence character strings, output tables, etc.).

Thus, standard desktop applications such as word processing software (e.g., Microsoft Word™ or Corel WordPerfect™) and database software (e.g., spreadsheet software such as Microsoft Excel™, Corel Quattro Pro™, or database programs such as Microsoft Access™, Paradox™, GeneWorks™, or MacVector™ or other similar programs) can be adapted to the present invention by inputting a character string corresponding to one or more polynucleotides and polypeptides of the invention (either nucleic acids or proteins, or both). For example, a system of the invention can include the foregoing software having the appropriate character string information, e.g., used in conjunction with a user interface (e.g., a GUI in a standard operating system such as a Windows, Macintosh or LINUX system) to manipulate strings of characters corresponding to the sequences herein. As noted, specialized alignment programs such as BLAST can also be incorporated into the systems of the invention for alignment of nucleic acids or proteins (or corresponding character strings).

Systems in the present invention typically include a digital computer with data sets entered into the software system comprising any of the sequences herein. The computer can be, e.g., a PC (Intel x86 or Pentium chip-compatible DOS™, OS2™ WINDOWS™ WINDOWSNT™, WINDOWS95™, WINDOWS2000™, WINDOWS98™, LINUX based machine, a MACINTOSH™, Power PC, or a UNIX based (e.g., SUN™ work station) machine) or other commercially available computer that is known to one of skill. Software for aligning or otherwise manipulating sequences is available, or can easily be constructed by one of skill using a standard programming language such as Visualbasic, PERL, Fortran, Basic, Java, or the like.

Any controller or computer optionally includes a monitor which is often a cathode ray tube ("CRT") display, a flat panel display (e.g., active matrix liquid crystal display, liquid crystal display), or others. Computer circuitry is often placed in a box which includes numerous integrated circuit chips, such as a microprocessor, memory, interface circuits, and others. The box also optionally includes a hard disk drive, a floppy disk drive, a high capacity removable drive such as a writeable CD-ROM, and other common peripheral elements. Inputting devices such as a keyboard or mouse optionally provide for input from a user and for user selection of sequences to be compared or otherwise manipulated in the relevant computer system.

The computer typically includes appropriate software for receiving user instructions, either in the form of user input into a set parameter fields, e.g., in a GUI, or in the form of preprogrammed instructions, e.g., preprogrammed for a variety of different specific operations. The software then converts these instructions to appropriate language for instructing the operation, e.g., of appropriate mechanisms or transport controllers to carry out the desired operation. The software can also include output elements for controlling nucleic acid synthesis (e.g., based upon a sequence or an alignment of sequences herein), comparisons of samples for differential gene expression, or other operations.

Kits and Reagents

The present invention is optionally provided to a user as a kit. For example, a kit of the invention contains one or more nucleic acid, polypeptide, antibody, or cell line described herein (e.g., comprising, or with, a HA and/or NA molecule of the invention). The kit can contain a diagnostic nucleic acid or polypeptide, e.g., antibody, probe set, e.g., as a cDNA microarray packaged in a suitable container, or other nucleic acid such as one or more expression vector. The kit can also further comprise, one or more additional reagents, e.g., substrates, labels, primers, for labeling expression products, tubes and/or other accessories, reagents for collecting samples, buffers, hybridization chambers, cover slips, etc. The kit optionally further comprises an instruction set or user manual detailing preferred methods of using the kit components for discovery or application of diagnostic sets, etc.

When used according to the instructions, the kit can be used, e.g., for evaluating a disease state or condition, for evaluating effects of a pharmaceutical agent or other treatment intervention on progression of a disease state or condition in a cell or organism, or for use as a vaccine, etc.

In an additional aspect, the present invention provides system kits embodying the methods, composition, systems and apparatus herein. System kits of the invention optionally comprise one or more of the following: (1) an apparatus, system, system component or apparatus component; (2) instructions for practicing methods described herein, and/or for operating the apparatus or apparatus components herein and/or for using the compositions herein. In a further aspect, the present invention provides for the use of any apparatus, apparatus component, composition or kit herein, for the practice of any method or assay herein, and/or for the use of any apparatus or kit to practice any assay or method herein.

Additionally, the kits can include one or more translation system as noted above (e.g., a cell) with appropriate packaging material, containers for holding the components of the kit, instructional materials for practicing the methods herein and/or the like. Similarly, products of the translation systems (e.g., proteins such as HA and/or NA molecules) can be provided in kit form, e.g., with containers for holding the components of the kit, instructional materials for practicing the methods herein and/or the like.

To facilitate use of the methods and compositions of the invention, any of the vaccine components and/or compositions, e.g., reasserted virus in allantoic fluid, etc., and additional components, such as, buffer, cells, culture medium, useful for packaging and infection of influenza viruses for experimental or therapeutic vaccine purposes, can be packaged in the form of a kit. Typically, the kit contains, in addition to the above components, additional materials which can include, e.g., instructions for performing the methods of the invention, packaging material, and a container.

EXAMPLES

Construction and Analysis of H5N1 ca Viruses and Vaccines

Various sequences herein comprising H5N1 HA/NA sequences were used to create influenza viruses and vaccines. The HA sequences in such vaccines were altered from wild-type by removal of the polybasic cleavage site within the HA. The HA/NA sequences were reasserted (in a 6:2 reassortment) with A/AA/6/60 (an att, ca virus, see above).

Three strains of H5N1 influenza were used in this example: A/VN/1203/2004, A/HK/491/97, and A/HK/213/2003. Such strains are also referred to within this example as the '97, '03, and '04 strains based on their year designations. The percent similarity of the HA genes of such three strains is 95-96%. FIG. 1 illustrates modification of the polybasic cleavage site of an exemplary HA sequence, the '04 HA sequences, used to construct the viruses/vaccines. As stated previously, various embodiments of the invention comprise sequences which have differing regions of the polybasic cleavage site removed. See above.

As stated, the modified H5N1 sequences (i.e., the modified '97, '03, and '04 genes) were used to construct 6:2 reassortant viruses with A/AA/6/60. It will be appreciated, and is pointed out elsewhere herein, that other desirable backbones could also have been used (e.g., PR8, etc.).

In the 6:2 reassortants of this example, the HA and NA gene sequences were derived from the wild type parent virus and the remaining genes were characterized by sequence analysis as derived from the A/AA/6/60 ca parent virus. The reasserted viruses replicated to 8.0-8.5 $\log_{10}TCID_{50}$ in eggs. However, it will be appreciated that other embodiments wherein the $\log_{10}TCID_{50}$ comprises from about 7.0 to about 9.0, from about 7.5-8.5, or from about 8.0-8.5 are also claimed within the invention. The cleavability of the modified HA in the constructed viruses by endogenous proteases was restricted in vitro and the viruses were dependent on trypsin (e.g., from about 0.1 ug/ml to about 1.0 ug/ml) for growth. The constructed viruses were temperature sensitive in vitro.

The H5N1 ca reassortant viruses (having the modified '97, '03, or '04 HA genes) were not highly pathogenic for chickens. For example, when 4-week-old SPF white Plymouth Rock chickens were inoculated intravenously with a 1:10 dilution of stock virus ($10^{8-8.75}$ TCID$_{50}$/ml) and observed for 10 days, it was observed that 8 out of 8 chickens died within 1-2 days when wild-type '97, '03, and '04 H5N1 were used, while 0 of 8 chickens died when the H5N1 ca reassortant viruses were used. As can be seen in FIG. 2, the intranasally administered H5N1 ca reassortant viruses did not replicate in chickens.

The H5N1/AA ca reassortants were also not lethal for mice. See FIG. 3, which also shows the TCID$_{50}$ for the H5N1 wild-type strains. FIG. 4 shows that the 1997 and 2004 H5N1 ca reassortant viruses were restricted in replication in mice. FIG. 5, shows that the H5N1 ca reassorted viruses are restricted in replication in lungs of mice.

A comparison of the serum HAI antibody titers elicited in mice following a single intranasal dose of vaccine (2003 ca as compared against 2003 wild-type), is shown in FIG. 6.

FIG. 7 shows similar measurements, but using serum neutralizing antibody titers.

Figure 8:
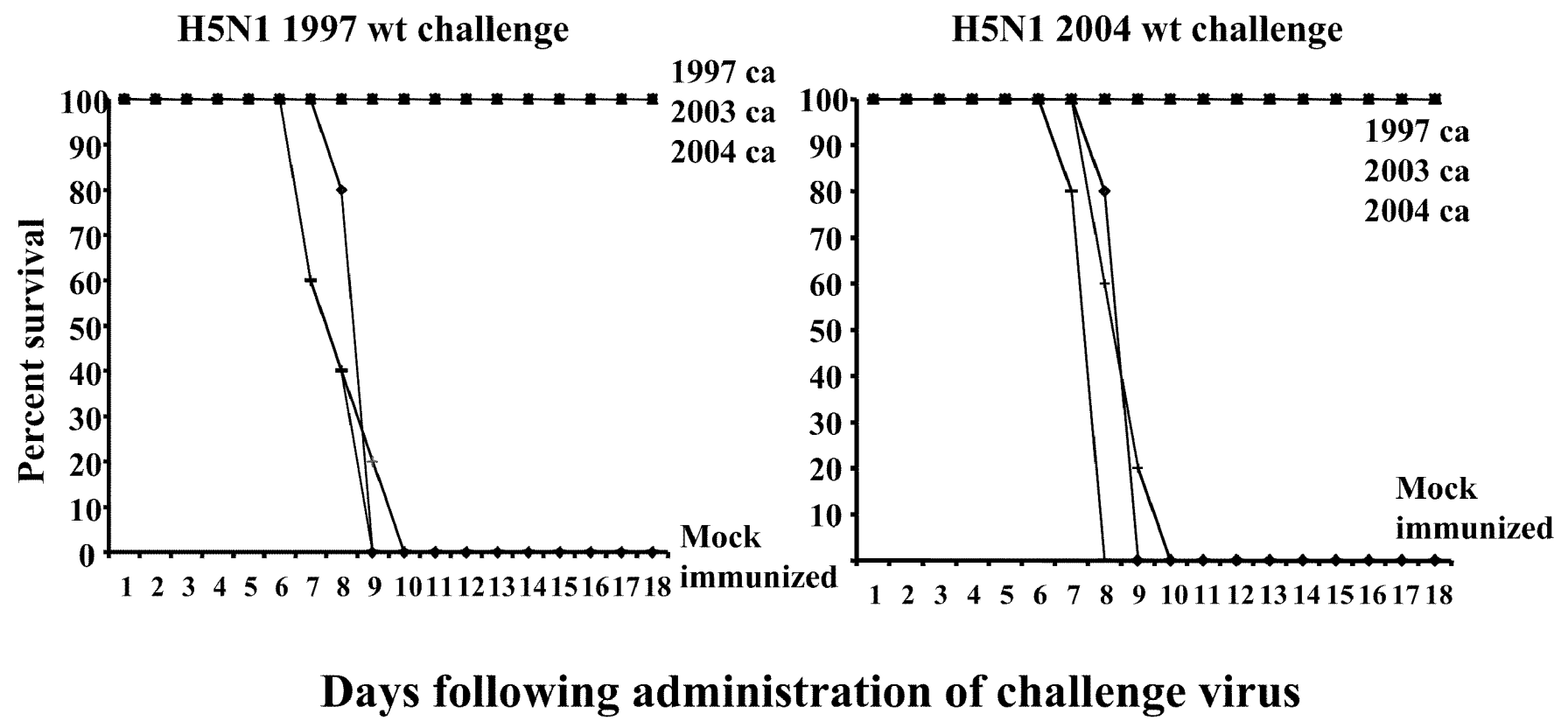

FIG. 8 displays that the H5N1 ca reassortant viruses protect mice from lethal challenge with 50, 500, or 5,000 LD$_{50}$ of wild-type H5N1 virus. FIG. 9 shows the efficacy of protection from pulmonary replication of homologous and heterologous H5N1 challenge viruses in mice. As can be seen, the ca reassortants replicated less well than the wild-type viruses did. FIG. 10 shows related data using upper respiratory tracts of mice. Those of skill in the art will be familiar with homologous and heterologous challenges (e.g., testing whether 2003 vaccine protects against a 2003 wild-type challenge (homologous) or whether a 2003 vaccine protects against a 1997 wild-type challenge (heterologous), etc.).

Figure 11:
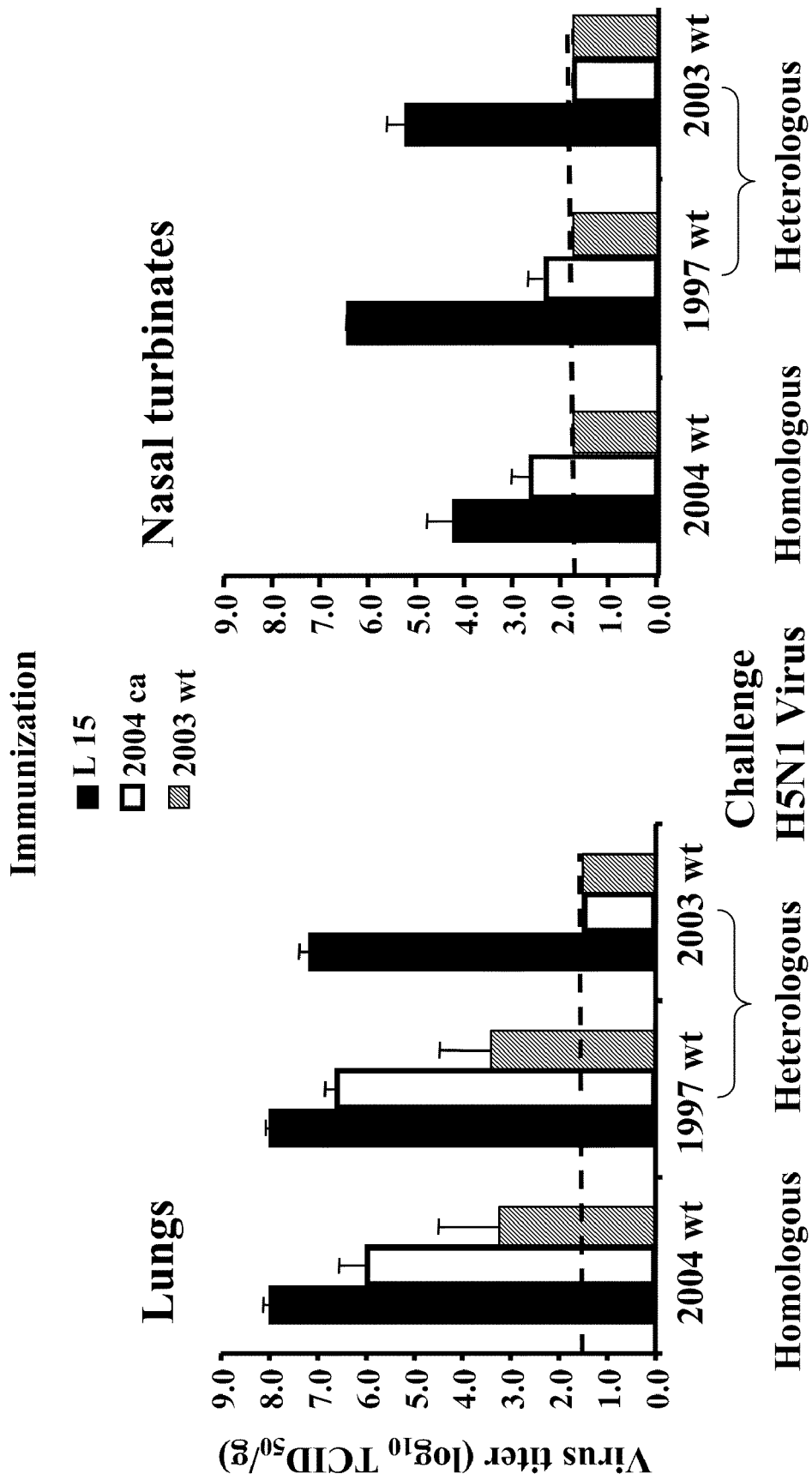
FIG. 11: Illustrates the efficacy of protection conferred by 2004 H5N1 ca vaccine against high dose ($10_5 TCID_{50}$) challenge with homologous or heterologous H5N1 wt viruses in mice.
Figure 12:
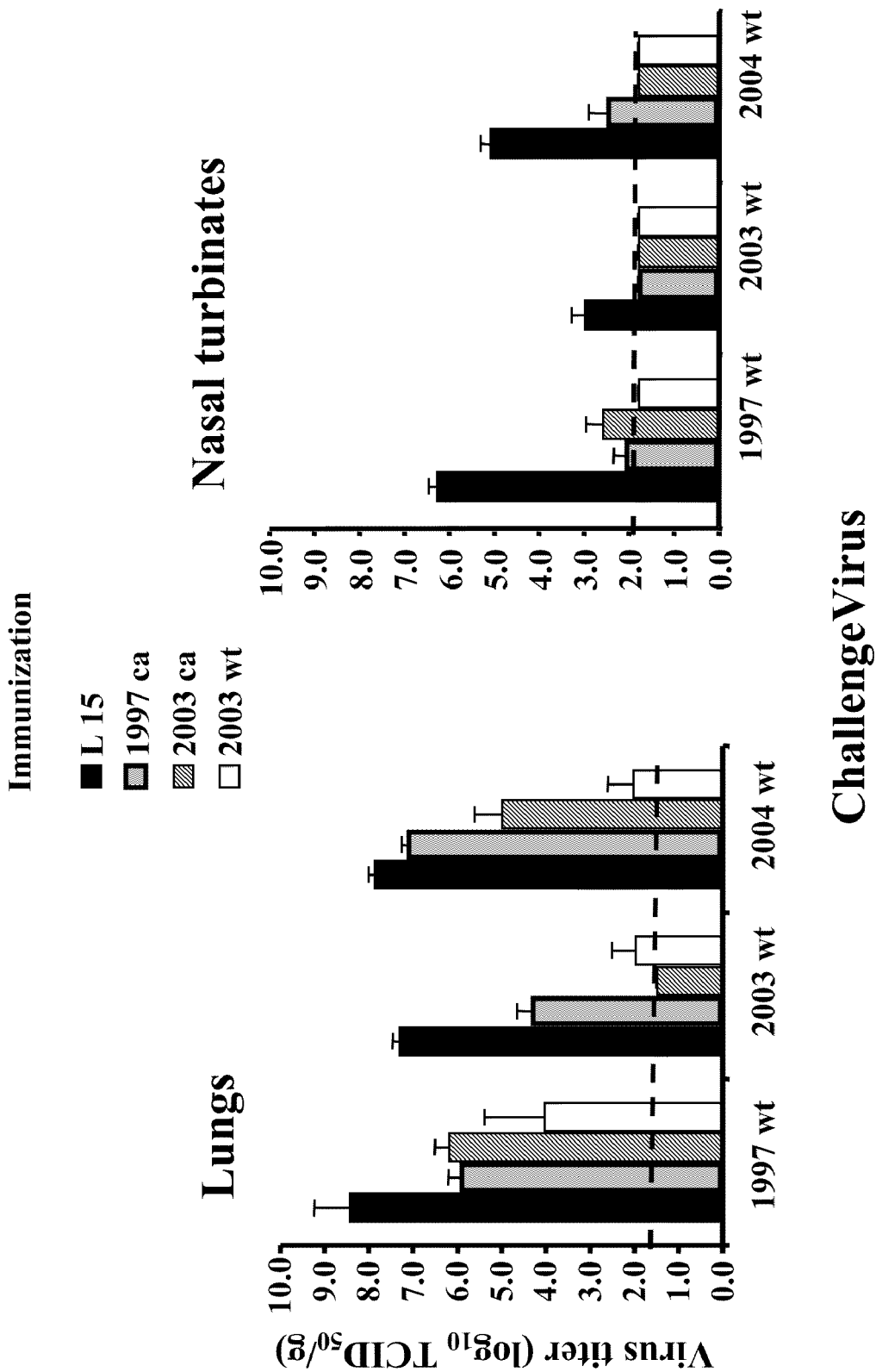
FIG. 12: Illustrates the efficacy of protection conferred by 1997 and 2003 H5N1 ca vaccines against high dose ($10_5 TCID_{50}$) challenges with homologous or heterologous H5N1 wild-type viruses in mice.
Figure 13:
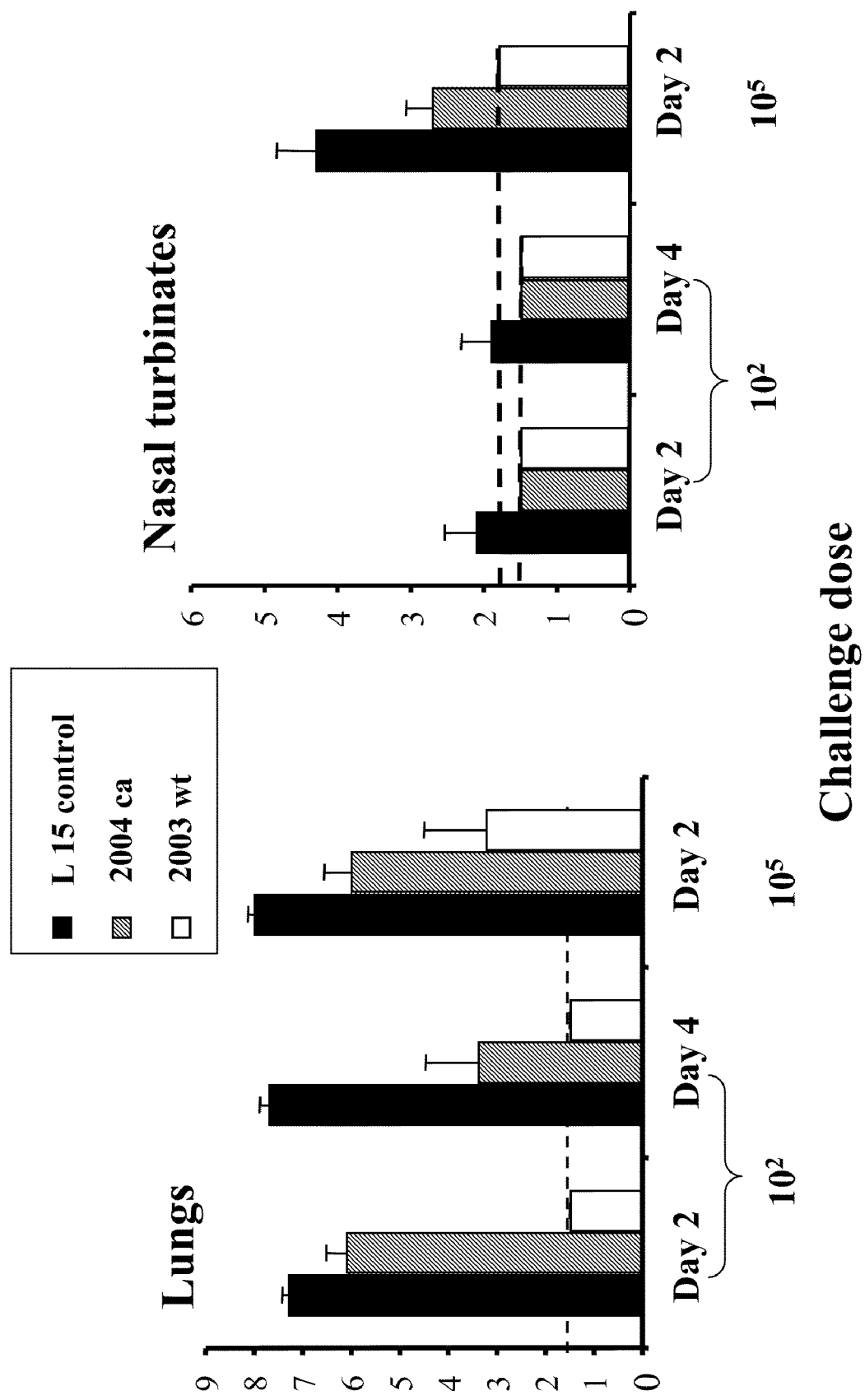
FIG. 13: Illustrates the efficacy of protection conferred by 2004 H5N1 ca vaccine against low or high doses of homologous H5N1 wild-type virus challenges in mice.

FIG. 11 shows efficacy of protection conferred by 2004 H5N1 ca vaccine against high dose ($10^5$TCID$_{50}$) challenge with homologous or heterologous H5N1 wild-type viruses in mice. FIG. 12 shows efficacy of protection conferred by 1997 and 2003 H5N1 ca vaccines against high dose ($10^5$TCID$_{50}$) challenge with homologous or heterologous H5N1 wild-type viruses in mice. FIG. 13 shows efficacy of protection conferred by 2004 H5N1 ca vaccine against low or high doses of homologous H5N1 wild-type virus challenge in mice. FIGS. 11-13 demonstrate that the tested vaccines could protect against other related viruses.

The current example demonstrates several points concerning exemplary H5N1 ca reassortant viruses/vaccines of the invention. The modified ca reassortant '97, '03, and '04 viruses were shown to have in vitro ts phenotype, loss of pathogenicity in chickens and attenuation in mice. It is expected that attenuation is also present in ferrets. Efficacy of protection and cross-protection against lethal challenge and systemic spread with wild-type viruses in mice was also shown. Efficacy of protection and cross-protections against replication of wild-type challenge viruses in the respiratory tract of mice is also expected.

It is contemplated to use these (and similar) viruses/vaccines to determine whether immunogenticy and efficacy is improved following 2 doses of vaccine; to assess immunogenicity in non-human primates; to assess attenuation and vaccine efficacy in ferrets; to determine the contribution of humoral and cellular immunity to observed efficacy of the produced vaccines in mice; to determine which residues of the 2003 HA contribute to enhanced immunogenicity and introduce them into 1997 and 2004 HAs; and to determine the effects of deleting the multibasic amino acid cleavage site and of the gene constellation.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes.

What is claimed is:

1. A reassortant influenza virus, wherein said virus comprises at least 6 internal genome segments from A/Ann Arbor/6/60 and at least one genome segment comprising a nucleic acid encoding a hemagglutinin polypeptide comprising the amino acid sequence of SEQ ID NO: 11.

2. An immunogenic composition comprising an immunologically effective amount of the reassortant influenza virus of claim 1.

3. A method for stimulating the immune system of an individual to produce a protective immune response against influenza virus, the method comprising administering to the individual an immunologically effective amount of the reassortant influenza virus of claim 1 in a physiologically effective carrier.

4. A method of prophylactic or therapeutic treatment of a viral infection in a subject, the method comprising: administering to the subject, the reassortant virus of claim 1 in an amount effective to produce an immunogenic response against the viral infection.

5. The method of claim 4, wherein the subject is a human.

6. The immunogenic composition of claim 2, wherein said reassortant influenza virus further comprises a neuramidinase genome segment comprising a nucleic acid encoding a neuramidinase polypeptide selected from the group consisting of: the polypeptides of SEQ ID NOs: 12, 14, 16, 18, and 20.

7. A live attenuated influenza vaccine comprising the composition of claim 2.

8. A split virus or killed virus vaccine comprising the composition of claim 2.

9. A live attenuated influenza vaccine comprising the composition of claim 6.

10. A split virus or killed virus vaccine comprising the composition of claim 6.

11. A method for producing influenza viruses in cell culture, the method comprising:

i) introducing into a population of host cells a plurality of vectors comprising nucleic acid sequences corresponding to at least 6 internal genome segments of the influenza strain A/Ann Arbor/6/60; and at least one genome segment comprising a nucleic acid encoding a hemagglutinin polypeptide comprising the amino acid sequence of SEQ ID NO: 11, ii) culturing the population of host cells at a temperature less than or equal to 35° C.; and, iii) recovering a plurality of influenza viruses.

12. An immunogenic composition comprising an immunologically effective amount of the influenza virus produced by the method of claim 11.

13. A method for stimulating the immune system of an individual to produce a protective immune response against influenza virus, the method comprising administering to the individual an immunologically effective amount of the influenza virus produced by the method of claim 11 in a physiologically effective carrier.

14. A method for stimulating the immune system of an individual to produce a protective immune response against influenza virus, the method comprising administering to the individual the immunogenic composition of claim 12.

15. A live attenuated influenza vaccine comprising the immunogenic composition of claim 12.

16. A split virus or killed virus vaccine comprising the immunogenic composition of claim 12.

17. The method of claim 11, wherein the plurality of vectors further comprise nucleic acids corresponding to a genome segment comprising a nucleic acid encoding a neuramidinase polypeptide comprising the amino acid sequence selected from the group consisting of SEQ ID NOs: 12, 14, 16, 18, and 20.

* * * * *

SEQUENCE LISTING

```
<160> NUMBER OF SEQ ID NOS: 22

<210> SEQ ID NO 1
<211> LENGTH: 1767
<212> TYPE: DNA
<213> ORGANISM: Influenza virus

<400> SEQUENCE: 1
agcaaaagca ggggttcaat ctgtcaaaat ggagaaaata gtgcttcttt ttgcaatagt      60
cagtcttgtt aaaagtgatc agatttgcat tggttaccat gcaaacaact cgacagagca     120
ggttgacaca ataatggaaa agaacgttac tgttacacat gcccaagaca tactggaaaa     180
gaaacacaac gggaagctct gcgatctaga tggagtgaag cctctaattt tgagagattg     240
tagcgtagct ggatggctcc tcggaaaccc aatgtgtgac gaattcatca atgtgccgga     300
atggtcttac atagtggaga aggccaatcc agtcaatgac ctctgttacc caggggattt     360
caatgactat gaagaattga acacctatt gagcagaata aaccattttg agaaaattca     420
gatcatcccc aaaagttctt ggtccagtca tgaagcctca ttagggggtga gctcagcatg     480
```

```
tccataccag ggaaagtcct ccttttttcag aaatgtggta tggcttatca aaaagaacag      540 tacatacccca acaataaaga ggagctacaa taataccaac caagaagatc ttttggtact      600
gtgggggatt caccatccta atgatgcggc agagcagaca aagctctatc aaaacccaac      660
cacctatatt tccgttggga catcaacact aaaccagaga ttggtaccaa gaatagctac      720
tagatccaaa gtaaacggc  aaagtggaag atggagttc  ttctggacaa ttttaaagcc      780
gaatgatgca atcaacttcg agagtaatgg aaatttcatt gctccagaat atgcatacaa      840
aattgtcaag aaaggggact caacaattat gaaaagtgaa ttggaatatg gtaactgcaa      900
caccaagtgt caaactccaa tgggggcgat aaactctagc atgccattcc acaatataca      960
ccctctcacc attggggaat gccccaaata tgtgaaatca aacagattag tccttgcgac     1020
tgggctcaga atagccctc  aaagagagac tcgaggatta tttggagcta tagcaggttt     1080
tatagaggga ggatggcagg gaatggtaga tggttggtat gggtaccacc atagcaatga     1140 gcagggagt  gggtacgctg cagacaaaga atccactcaa aaggcaatag atggagtcac     1200
caataaggtc aactcgatca ttgacaaaat gaacactcag tttgaggccg ttggaaggga     1260
atttaacaac ttagaaagga gaatagagaa tttaaacaag aagatggaag acgggttcct     1320
agatgtctgg acttataatg ctgaacttct ggttctcatg gaaaatgaga gaactctaga     1380 cttttcatgac tcaaatgtca agaaccttta cgacaaggtc cgactacagc ttagggataa     1440
tgcaaaggag ctgggtaacg gttgtttcga gttctatcat aaatgtgata atgaatgtat     1500
ggaaagtgta agaaatggaa cgtatgacta cccgcagtat tcagaagaag cgagactaaa     1560
aagagaggaa ataagtggag taaaattgga atcaatagga atttaccaaa tactgtcaat     1620
ttattctaca gtggcgagtt ccctagcact ggcaatcatg gtagctggtc tatccttatg     1680
gatgtgctcc aatgggtcgt tacaatgcag aatttgcatt taaatttgtg agttcagatt     1740
gtagttaaaa acacccttgt ttctact                                           1767

<210> SEQ ID NO 2
<211> LENGTH: 1398
<212> TYPE: DNA
<213> ORGANISM: Influenza virus

<400> SEQUENCE: 2
agcaaaagca ggagttcaaa atgaatccaa atcagaagat aataaccatc gggtcaatct       60
gtatggtaac tggaatagtt agcttaatgt tacaaattgg aacatgatc  tcaatatggg      120 tcagtcattc aattcacaca gggaatcaac accaatctga accaatcagc aatactaatt      180
ttcttactga gaaagctgtg gcttcagtaa aattagcggg caattcatct ctttgcccca      240
ttaacggatg ggctgtatac agtaaggaca acagtataag gatcggttcc aaggggatg      300 tgtttgttat aagagagccg ttcatctcat gctcccactt ggaatgcaga actttctttt      360
tgactcaggg agccttgctg aatgacaagc actccaatgg gactgtcaaa gacagaagcc      420
ctcacagaac attaatgagt tgtcctgtgg gtgaggctcc ctccccatat aactcaaggt      480
ttgagtctgt tgcttggtca gcaagtgctt gccatgatgg caccagttgg ttgacgattg      540
gaatttctgg cccagacaat ggggctgtgg ctgtattgaa atacaatggc ataataacag      600
acactatcaa gagttggagg aacaacatac tgagaactca agagtctgaa tgtgcatgtg      660
taaatggctc ttgctttact gtaatgactg acgaccaag  taatggtcag gcatcacata      720
agatcttcaa aatggaaaaa gggaaagtgg ttaaatcagt cgaattggat gctcctaatt      780
```

| | |
|---|---:|
| atcactatga ggaatgctcc tgttatccta atgccggaga aatcacatgt gtgtgcaggg | 840 |
| ataattggca tggctcaaat cggccatggg tatctttcaa tcaaatttg gagtatcaaa | 900 |
| taggatatat atgcagtgga gttttcggag acaatccacg ccccaatgat ggaacaggta | 960 |
| gttgtggtcc ggtgtcctct aacgggcat atgggtaaa agggttttca tttaaatacg | 1020 |
| gcaatggtgt ctggatcggg agaaccaaaa gcactaattc caggagcggc tttgaaatga | 1080 |
| tttgggatcc aaatgggtgg actgaaacgg acagtagctt ttcagtgaaa caagatatcg | 1140 |
| tagcaataac tgattggtca ggatatagcg ggagttttgt ccagcatcca gaactgacag | 1200 |
| gactagattg cataagacct tgtttctggg ttgagttgat cagagggcgg cccaaagaga | 1260 |
| gcacaatttg gactagtggg agcagcatat cttttttgtgg tgtaaatagt gacactgtgg | 1320 |
| gttggtcttg gccagacggt gctgagttgc cattcaccat tgacaagtag tttgttcaaa | 1380 |
| aaactccttg tttctact | 1398 |

<210> SEQ ID NO 3
<211> LENGTH: 1767
<212> TYPE: DNA
<213> ORGANISM: Influenza virus

<400> SEQUENCE: 3

| | |
|---|---:|
| agcaaaagca ggggttcaat ctgtcaaaat ggagaaaata gtgcttcttt ttgcaatagt | 60 |
| cagtcttgtt aaaagtgatc agatttgcat tggttaccat gcaaacaact cgacagagca | 120 |
| ggttgacaca ataatggaaa agaacgttac tgttacacat gcccaagaca tactggaaaa | 180 |
| gacacacaac gggaagctct gcgatctaga tggagtgaag cctctaattt tgagagattg | 240 |
| tagtgtagct ggatggctcc tcggaaaccc aatgtgtgac gaattcatca atgtgccgga | 300 |
| atggtcttac atagtggaga aggccaatcc agccaatgac ctctgttacc caggggattt | 360 |
| caacgactat gaagaattga acacctatt gagcagaata aaccattttg agaaaattca | 420 |
| gatcatcccc aaaaattctt ggtccagtca tgaagcctca ttaggggtga gctcagcatg | 480 |
| tccataccaa ggaaagtcct ccttttcag aatgtggta tggcttatca aaagaacaa | 540 |
| tgcataccca acaataaaga ggagctacaa taataccaac caagaagatc ttttggtatt | 600 |
| gtgggggatt caccatccta tgatgcggc agagcagact aggctctatc aaaacccaac | 660 |
| cacctacatt tccgttggga catcaacact aaaccagaga ttggtaccaa aaatagctac | 720 |
| tagatccaaa gtaaacgggc aaaatggaag gatggagttc ttctggacaa ttttaaaacc | 780 |
| gaatgatgca atcaacttcg agagcaatgg aaatttcatt gctccagaat atgcatacaa | 840 |
| aattgtcaag aaaggggact cagcaattat gaaaagtgaa ttggaatatg gtaactgcaa | 900 |
| caccaagtgt caaactccaa tggggcgat aaactctagt atgccattcc acaatataca | 960 |
| ccctctcacc atcggggaat gccccaaata tgtgaaatca acagattag tccttgcgac | 1020 |
| tgggctcaga aatagccctc aaagagagac tcgaggatta tttggagcta tagcaggttt | 1080 |
| tatagaggga ggatggcagg gaatggtaga tggttggtat gggtaccacc atagcaatga | 1140 |
| gcaggggagt gggtacgctg cagacaaaga atccactcaa aaggcaatag atggagtcac | 1200 |
| caataaggtc aactcgatca ttgacaaaat gaacactcag tttgaggccg ttggaaggga | 1260 |
| atttaataac ttagaaagga gaatagaaa tttaaacaag aagatggaag acggattcct | 1320 |
| agatgtctgg acttataatg ctgaacttct ggttctcatg gaaaatgaga gaactctaga | 1380 |
| cttttcatgac tcaaatgtca agaaccttta cgacaaggtc cgactacagc ttagggataa | 1440 |
| tgcaaaggag ctgggtaacg gttgtttcga gttctatcac aaatgtgata tgaatgtat | 1500 |

```
ggaaagtgta agaaacggaa cgtatgacta cccgcagtat tcagaagaag caagactaaa    1560
aagagaggaa ataagtggag taaaattgga gtcaatagga acttaccaaa tactgtcaat    1620
ttattctaca gtggcgagtt ccctagcact ggcaatcatg gtagctggtc tatctttatg    1680
gatgtgctcc aatgggtcgt tacaatgcag aatttgcatt taaatttgtg agttcagatt    1740
gtagttaaaa acaccttgt ttctact                                         1767

<210> SEQ ID NO 4
<211> LENGTH: 1458
<212> TYPE: DNA
<213> ORGANISM: Influenza virus

<400> SEQUENCE: 4
agcaaaagca ggagttcaaa atgaatccaa atcagaagat aacaaccatt ggatcaatct      60
gtatggtaat tggaatagtt agcttgatgt tacaaattgg aacataatc tcaatatggg     120 ttagtcattc aattcaaaca gggaatcaac accaggctga accatgcaat caaagcatta    180
ttacttatga aaacaacacc tgggtaaacc agacatatgt caacatcagc aataccaatt    240
ttcttactga gaaagctgtg gcttcagtaa cattagcggg caattcatct ctttgcccca    300
ttagtggatg ggctgtatac agtaaggaca acggtataag aatcggttcc aaggggatg     360 tgtttgttat aagagagccg ttcatctcat gctcccactt ggaatgcaga actttctttt    420
tgactcaggg agccttgctg aatgacaagc attctaatgg accgtcaaa gacagaagcc     480 ctcacagaac attaatgagt gtcccgtgg gtgaggctcc ttccccatac aactcgaggt     540
ttgagtctgt tgcttggtcg gcaagtgctt gtcatgatgg cactagttgg ttgacaattg    600
gaatttctgg cccagacaat ggggctgtgg ctgtattgaa atacaatggc ataataacag    660
acactatcaa gagttggagg aacaacataa tgagaactca agagtctgaa tgtgcatgtg    720
taaatggctc ttgctttact gttatgactg atggaccaag taatgggcag gcttcataca    780
aaatcttcag aatagaaaaa gggaaagtag ttaaatcagc cgaattaaat gcccctaatt    840
atcactatga ggagtgctcc tgttatcctg atgctggaga aatcacatgt gtgtgcaggg    900
ataactggca tggctcaaat cggccatggg tatctttcaa tcaaaatttg gagtatcgaa    960
taggatatat atgcagtgga gttttcggag acaatccacg ccccaatgat gggacaggca   1020
gttgtggtcc ggtgtcccct aaaggggcat atggaataaa agggttctca tttaaatacg   1080
gcaatggtgt ttggatcggg agaaccaaaa gcactaattc caggagcggc tttgaaatga   1140
tttgggatcc aaatggatgg actggtacgg acagtaattt ttcagtaaag caagatattg   1200
tagctataac cgattggtca ggatatagcg ggagttttgt ccagcatcca gaactgacag   1260
gattagattg cataagacct tgtttctggg ttgagctaat cagagggcgg cccaaagaga   1320
gcacaatttg gactagtggg agcagcatat ccttttgtgg tgtaaatagt gacactgtgg   1380
gttggtcttg ccagacggt gctgagttgc cattcaccat tgacaagtag tttgttcaaa    1440
aaactccttg tttctact                                                 1458

<210> SEQ ID NO 5
<211> LENGTH: 1767
<212> TYPE: DNA
<213> ORGANISM: Influenza virus

<400> SEQUENCE: 5
agcaaaagca ggggtataat ctgtcaaaat ggagaaaata gtgcttcttc ttgcaacagt     60
```

| | |
|---|---:|
| cagccttgtt aaaagtgacc agatttgcat tggttaccat g

```
gcccctatag aactttaatg agctgtcctg ttggtgaggc cccttcccca tacaactcaa    480
ggtttgagtc tgttgcttgg tcagcaagtg cttgccatga tggcattagt tggctaacaa    540
ttggaatttc cggtccggat aatggggctg tggctgtgtt gaaatacaat ggcataataa    600
cagacaccat caagagttgg aggaacaaca cactgaggac gcaagagtct gaatgtgcat    660
gtgtgaatgt tcttgtttt actgtaatga cagatggacc gagtaatgaa caggcctcat     720
acaagatttt caagatagaa aaggggaggg tagtcaaatc agttgagttg aacgccccta    780
attatcatta cgaggaatgc tcctgttatc ctgatgctgg cgaaatcaca tgtgtgtgca    840
gggataattg gcatggctcg aaccgaccat gggtgtcttt caatcagaat ctggagtatc    900
aaataggata tatatgcagt ggggttttcg gagacagtcc acgccccaat gatgggacag    960
gcagttgtgg tccagtgtct cttaacggag cgtatggagt aaaagggttt tcatttaaat   1020
acggcaatgg tgtttggatc gggagaacca aaagcactag ttccaggagc ggttttgaaa   1080
tgatttggga tccaaatggg tggaccgaaa cagacagtag cttctcgttg aagcaagaca   1140
tcatagcgat aactgattgg tcaggataca gcgggagttt tattcaacat ccagaactga   1200
caggattaaa ttgcatgaga ccttgcttct gggttgaact aatcagaggg aggcccaaag   1260
agaaaacaat ctggactagt gggagcagta tatctttctg tggtgtaaat agtgacactg   1320
tgggttggtc ttggccagac ggtgctgagt tgccatacac cattgacaag tagtttgttc   1380
aaaaaactcc ttgtttctac t                                             1401

<210> SEQ ID NO 7
<211> LENGTH: 1767
<212> TYPE: DNA
<213> ORGANISM: Influenza virus

<400> SEQUENCE: 7
agcaaaagca ggggtataat ctgtcaaaat ggagaaaata gtgcttcttc ttgcaacagt     60
cagccttgtt aaaagtgacc agatttgcat tggttaccat gcaaacaact cgacagagca    120
agttgacaca ataatggaaa agaatgttac tgttacacat gcccaagaca tactggaaag    180
gacacacaac gggaagctct gcgatctaaa tggagtgaag cctctgattt tgagggattg    240
tagtgtagct ggatggctcc tcggaaaccc tatgtgtgac gaattcatca atgtgccgga    300
atggtcttac atagtggaga aggccagtcc agccaatgac ctctgttatc cagggaattt    360
caacgactat gaagaactga aacacctatt gagcagaata aaccattttg agaaaattca    420
gataatcccc aaaagttctt ggtccaatca tgatgcctca tcagggtga gctcagcatg     480 tccatacctt ggaggtcct ccttttcag aaatgtggta tggcttatca aaagaacag      540 tagctaccca acaataaaga ggagctacaa taataccaac caagaagatc ttttggtact    600 gtggggatt caccatccta atgatgcggc agagcagaca aggctctatc aaacccaac     660 cacctacatt tccgttggaa catcaacact gaaccagaga ttggttcag aaatagctac     720 tagacccaaa gtaaacgggc aaagtggaag aatggagttc ttctggacaa ttttaaagcc    780
gaatgatgcc atcaatttcg agagtaatgg aaatttcatt gctccagaat atgcatacaa    840
aattgtcaag aaaggggact caacaattat gaaaagtgaa ttggaatatg gtaactgcaa    900
caccaagtgt caaactccaa tgggggcaat aaactctagt atgccattcc acaacataca    960 cccctcacc atcggggaat gccccaaata tgtgaaatca acagattag tccttgcaac    1020 tggactcaga aataccctc aacgagagac gcgaggacta tttggagcta tagcaggttt   1080
```

-continued

| | |
|---|---|
| tatagaggga ggatggcagg gaatggtaga tggttggtat gggtaccacc atagcaatga | 1140 |
| gcagggagt ggatacgctg cagaccaaga atccacacaa aaggcaatag atggagtcac | 1200 |
| caataaggtc aactcgatca ttaacaaaat gaacactcag tttgaggccg ttggaaggga | 1260 |
| atttaataac ttggaaagga ggatagagaa tttaaacaag aaaatggaag acggattcct | 1320 |
| agatgtctgg acttacaatg ccgaacttct ggttctcatg gaaaatgaga gaactctaga | 1380 |
| ctttcatgac tcaaatgtca agaacctta cgacaaggtc cgactacagc ttagggataa | 1440 |
| tgcaaaggag ctgggtaatg gttgtttcga attctatcac aaatgtgata cgaatgtat | 1500 |
| ggaaagtgta aaaacggaa cgtatgacta cccgcagtat tcagaagaag caagactaaa | 1560 |
| cagagaggaa ataagtggag taaaattgga atcaatggga acttaccaaa tactgtcaat | 1620 |
| ttattcaaca gtggcgagtt ccctagcact ggcaatcatg gtagctggtc tatctttatg | 1680 |
| gatgtgctcc aatggatcgt tacaatgcag aatttgcatt taaatttgtg agttcagatt | 1740 |
| gtagttaaaa acacccttgt ttctact | 1767 |

<210> SEQ ID NO 8
<211> LENGTH: 1401
<212> TYPE: DNA
<213> ORGANISM: Influenza virus

<400> SEQUENCE: 8

| | |
|---|---|
| agcaaaagca ggagtttaaa atgaatccaa atcagaagat aataaccatt ggatcaatct | 60 |
| gcatggtagt tgggataatc agcttgatgt tacaaattgg aaacacaata tcagtatggg | 120 |
| tcagccacat aattaaaact tggcacccaa accagcctga accatgcaac caaagcatca | 180 |
| attttacac tgagcaggct gcagcttcag tgacattagc gggcaattcc tctctctgcc | 240 |
| ctattagtgg atgggctata tacagcaagg acaatagtat aagaattggt tccaaagggg | 300 |
| atgtgtttgt tataagagaa ccattcatct catgctccca tttggaatgc agaacctttt | 360 |
| tcttgaccca aggagcccta ttgaatgaca agcattctaa tgggaccgtc aaagacagga | 420 |
| gcccctatag aactttaatg agctgtcctg ttggtgaggc cccttcccca tacaactcaa | 480 |
| ggtttgagtc tgttgcttgg tcagcaagtg cttgccatga tggcattagt tggctaacaa | 540 |
| ttggaatttc cggtccggat aatgggggctg tggctgtgtt gaaatacaat ggcataataa | 600 |
| cagacaccat caagagttgg aggaacaaca cactgaggac gcaagagtct gaatgtgcat | 660 |
| gtgtgaatgg ttcttgtttt actgtaatga cagatggacc gagtaatgaa caggcctcat | 720 |
| acaagatttt caagatagaa aagggagggg tagtcaaatc agttgagttg aacgcccta | 780 |
| attatcatta cgaggaatgc tcctgttatc ctgatgctgg cgaaatcaca tgtgtgtgca | 840 |
| gggataattg gcatggctcg aaccgaccat gggtgtcttt caatcagaat ctggagtatc | 900 |
| aaataggata tatatgcagt gggggttttcg gagacagtcc acgccccaat gatgggacag | 960 |
| gcagttgtgg tccagtgtct cttaacggag cgtatgagt aaaagggttt catttaaat | 1020 |
| acggcaatgg tgtttggatc gggagaacca aaagcactag ttccaggagc ggttttgaaa | 1080 |
| tgatttggga tccaaatggg tggaccgaaa cagacagtag cttctcgttg aagcaagaca | 1140 |
| tcatagcgat aactgattgg tcaggataca gcgggagttt tattcaacat ccagaactga | 1200 |
| caggattaaa ttgcatgaga ccttgcttct gggttgaact aatcagaggg aggcccaaag | 1260 |
| agaaaacaat ctggactagt gggagcagta tatctttctg tggtgtaaat agtgacactg | 1320 |
| tgggttggtc ttggccagac ggtgctgagt tgccatacac cattgacaag agttttgttc | 1380 |
| aaaaaactcc ttgtttctac t | 1401 |

<210> SEQ ID NO 9
<211> LENGTH: 1690
<212> TYPE: DNA
<213> ORGANISM: Influenza virus

<400> SEQUENCE: 9

| | | | | | |
|---|---|---|---|---|---|
| ttaaccactc | aagatggaag | caataccact | aataactata | ctactagtag | taacagcaag | 60 |
| caatgcagac | aaaatctgca | tcggctacca | atcaacaaac | tccacagaaa | ccgtagacac | 120 |
| gctaacagaa | acaatgttc | ctgtgacaca | tgccaaagaa | ttgctccaca | cagagcacaa | 180 |
| tgggatgctg | tgtgcaacaa | atctgggacg | tcctcttatt | ctagacactt | gcaccattga | 240 |
| aggactgatc | tatggcaacc | cttcttgtga | tctactgttg | ggaggaagag | aatggtccta | 300 |
| catcgtcgaa | agaccatcgg | ctgttaatgg | aatgtgttac | cccgggaatg | tagaaaacct | 360 |
| agaggaacta | aggtcatttt | ttagttctgc | tagttcctac | caagaatcc | agatcttcc | 420 |
| agacacaatc | tggaatgtgt | cttacagtgg | aacaagcaaa | gcatgttcag | attcattcta | 480 |
| caggagcatg | agatggttga | ctcaaaagaa | caacgcttac | cctattcaag | acgcccaata | 540 |
| cacaaataat | agaggaaaga | gcattctttt | catgtgggc | ataaatcacc | cacctaccga | 600 |
| tactgcacag | acaaatctgt | acacaaggac | tgacacaaca | acaagtgtgg | caacagaaga | 660 |
| tataaatagg | accttcaaac | cagtgatagg | gccaaggccc | cttgtcaatg | gtctgcaggg | 720 |
| aagaattgat | tattattggt | cggtattgaa | accaggtcag | acattgcgag | taagatccaa | 780 |
| tgggaatcta | atcgctccat | ggtatgggca | cattctttca | ggagagagcc | acggaagaat | 840 |
| cctgaagact | gatttaaaca | gtggtagctg | tgtagtgcaa | tgtcaaacag | aaagaggtgg | 900 |
| cttaaatact | actttgccat | ccacaatgt | cagtaaatat | gcatttggaa | actgcccaaa | 960 |
| atatgttgga | gtaaagagtc | tcaaactggc | agttggtctg | aggaatgtgc | ctgctagatc | 1020 |
| aagtagagga | ctatttgggg | ccatagctgg | attcatagag | ggaggttggt | cagggctggt | 1080 |
| cgctggttgg | tatgggttcc | agcattcaaa | tgatcaaggg | gttggtatag | ctgcagatag | 1140 |
| agactcaact | caaagggcaa | ttgacaaaat | aacgtccaaa | gtgaataata | tagtcgataa | 1200 |
| aatgaacaag | caatatgaaa | ttattgatca | tgaattcagc | gaggttgaaa | atagactcaa | 1260 |
| tatgatcaat | aataagattg | atgaccagat | acaagacata | tgggcatata | acgctgaatt | 1320 |
| gctagtgctg | cttgaaaacc | agaaaacact | cgatgagcat | gatgcgaatg | taaacaatct | 1380 |
| atataacaaa | gtgaagaggg | cactgggttc | caatgcaatg | gaagatggga | aaggatgttt | 1440 |
| cgagctatac | cataaatgtg | atgatcagtg | catggagaca | attcggaacg | ggacctataa | 1500 |
| caggaggaag | tataaagagg | aatcaagact | agaaagacag | aaaatagaag | gggtcaagct | 1560 |
| ggaatctgaa | ggaacttaca | aaatcctcac | catttattcg | actgtcgcct | catctcttgt | 1620 |
| gattgcaatg | gggtttgctg | ccttcttgtt | ctgggccatg | tccaatggat | cttgcagatg | 1680 |
| caacatttga | | | | | | 1690 |

<210> SEQ ID NO 10
<211> LENGTH: 1428
<212> TYPE: DNA
<213> ORGANISM: Influenza virus

<400> SEQUENCE: 10

| | | | | | |
|---|---|---|---|---|---|
| aaatgaatcc | aaatcagaag | ataatagcaa | ttggctctgt | ttctctaact | attgcgacaa | 60 |
| tatgcctcct | catgcagatt | gctatcttag | caacgactat | gacactacat | ttcaagcaga | 120 |

```
atgaatgcat caactcctcg aataatcaag tagtgccatg tgaaccaatc ataatagaaa    180
ggaacataac agagatagtg catttgaata gtactacctt agagaaggaa atttgtccta    240
aagtagcaga ctacaggaat tggtcaaaac cacaatgtca atcacaggg ttcgctcctt     300 tctccaagga caattcaatt aggctctccg caggtggaga tatttgggtg acaagagaac    360
cttatgtatc gtgcggtctt ggtaaatgtt atcaatttgc acttgggcag ggaaccactt    420
tggagaacaa acactcaaac ggcacagcac atgatagaac tcctcataga acccttttaa    480
tgaatgagtt gggtgttccg tttcatttgg caaccaaaca agtgtgcata gcatggtcca    540
gctcaagctg ccatgatggg aaagcatggt tacatgtttg tgtcactggg gatgatagaa    600
atgcaacggc tagcatcatt tatgatggga tacttgttga cagtattggt tcatggtcta    660
aaaacatcct cagaactcag gagtcagaat gcgtttgcat caatggaacc tgtgcagtag    720
taatgactga tggaagtgca tcaggaaggg ctgacactag aatactattt attagagagg    780
ggaaaattgc cacacattag ccattgtcag gaagtgctca gcatgtggag gaatgctcct    840 gttaccccg atatccagaa gttagatgtg tttgcagaga caattggaag ggatccaata    900
ggcccgttct atatataaat atggcaaatt atagtattga ttccagttat gtgtgctcag    960
gacttgttgg cgacacacca agaaatgatg ataggtctag cagcagcaac tgcagagatc   1020
ctaataacga gagggggcc ccaggagtaa aaggtgggc cttgacaat ggaaatgaca       1080 tttggatggg aagaacaatc aaaaaggatt cgcgctcagg ttatgagact tcagggtca    1140 ttggtggttg gaccactgct aattccaagt cacagataaa tagacaagtc atagttgaca   1200
gtgataactc gtctgggtat tctggtatct tctctgttga aggcaaaagc tgcatcaaca   1260
ggtgttttta cgtggagttg ataagaggaa gaccaaagga gactagggtg tggtggactt   1320
caaatagcat cattgtattt tgtggaactt caggtaccta tggaacaggc tcatggcctg   1380
atggggcgaa tatcaatttc atgcctatat aagctttcgc aatttttag                1428
```

<210> SEQ ID NO 11
<211> LENGTH: 564
<212> TYPE: PRT
<213> ORGANISM: Influenza virus

<400> SEQUENCE: 11

Met Glu Lys Ile Val Leu Leu Phe Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Lys His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Val Asn Asp Leu Cys Tyr Pro Gly Asp Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser His Glu Ala Ser
    130                 135                 140

-continued

```
Leu Gly Val Ser Ser Ala Cys Pro Tyr Gln Gly Lys Ser Ser Phe Phe
145                 150                 155                 160

Arg Asn Val Val Trp Leu Ile Lys Lys Asn Ser Thr Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Lys Leu Tyr Gln
        195                 200                 205

Asn Pro Thr Thr Tyr Ile Ser Val Gly Thr Ser Thr Leu Asn Gln Arg
    210                 215                 220

Leu Val Pro Arg Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Thr Ile Met Lys Ser Glu Leu Glu Tyr Gly
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Thr Arg Gly Leu Phe Gly Ala Ile Ala Gly Phe Ile
            340                 345                 350

Glu Gly Gly Trp Gln Gly Met Val Asp Gly Trp Tyr Gly Tyr His His
        355                 360                 365

Ser Asn Glu Gln Gly Ser Gly Tyr Ala Ala Asp Lys Glu Ser Thr Gln
    370                 375                 380

Lys Ala Ile Asp Gly Val Thr Asn Lys Val Asn Ser Ile Ile Asp Lys
385                 390                 395                 400

Met Asn Thr Gln Phe Glu Ala Val Gly Arg Glu Phe Asn Asn Leu Glu
                405                 410                 415

Arg Arg Ile Glu Asn Leu Asn Lys Lys Met Glu Asp Gly Phe Leu Asp
            420                 425                 430

Val Trp Thr Tyr Asn Ala Glu Leu Leu Val Leu Met Glu Asn Glu Arg
        435                 440                 445

Thr Leu Asp Phe His Asp Ser Asn Val Lys Asn Leu Tyr Asp Lys Val
    450                 455                 460

Arg Leu Gln Leu Arg Asp Asn Ala Lys Glu Leu Gly Asn Gly Cys Phe
465                 470                 475                 480

Glu Phe Tyr His Lys Cys Asp Asn Glu Cys Met Glu Ser Val Arg Asn
                485                 490                 495

Gly Thr Tyr Asp Tyr Pro Gln Tyr Ser Glu Glu Ala Arg Leu Lys Arg
            500                 505                 510

Glu Glu Ile Ser Gly Val Lys Leu Glu Ser Ile Gly Ile Tyr Gln Ile
        515                 520                 525

Leu Ser Ile Tyr Ser Thr Val Ala Ser Ser Leu Ala Leu Ala Ile Met
    530                 535                 540

Val Ala Gly Leu Ser Leu Trp Met Cys Ser Asn Gly Ser Leu Gln Cys
545                 550                 555                 560

Arg Ile Cys Ile
```

<210> SEQ ID NO 12
<211> LENGTH: 449
<212> TYPE: PRT
<213> ORGANISM: Influenza virus

<400> SEQUENCE: 12

```
Met Asn Pro Asn Gln Lys Ile Ile Thr Ile Gly Ser Ile Cys Met Val
1               5                   10                  15

Thr Gly Ile Val Ser Leu Met Leu Gln Ile Gly Asn Met Ile Ser Ile
            20                  25                  30

Trp Val Ser His Ser Ile His Thr Gly Asn Gln His Gln Ser Glu Pro
        35                  40                  45

Ile Ser Asn Thr Asn Phe Leu Thr Glu Lys Ala Val Ala Ser Val Lys
    50                  55                  60

Leu Ala Gly Asn Ser Ser Leu Cys Pro Ile Asn Gly Trp Ala Val Tyr
65                  70                  75                  80

Ser Lys Asp Asn Ser Ile Arg Ile Gly Ser Lys Gly Asp Val Phe Val
                85                  90                  95

Ile Arg Glu Pro Phe Ile Ser Cys Ser His Leu Glu Cys Arg Thr Phe
            100                 105                 110

Phe Leu Thr Gln Gly Ala Leu Leu Asn Asp Lys His Ser Asn Gly Thr
        115                 120                 125

Val Lys Asp Arg Ser Pro His Arg Thr Leu Met Ser Cys Pro Val Gly
    130                 135                 140

Glu Ala Pro Ser Pro Tyr Asn Ser Arg Phe Glu Ser Val Ala Trp Ser
145                 150                 155                 160

Ala Ser Ala Cys His Asp Gly Thr Ser Trp Leu Thr Ile Gly Ile Ser
                165                 170                 175

Gly Pro Asp Asn Gly Ala Val Ala Val Leu Lys Tyr Asn Gly Ile Ile
            180                 185                 190

Thr Asp Thr Ile Lys Ser Trp Arg Asn Asn Ile Leu Arg Thr Gln Glu
        195                 200                 205

Ser Glu Cys Ala Cys Val Asn Gly Ser Cys Phe Thr Val Met Thr Asp
    210                 215                 220

Gly Pro Ser Asn Gly Gln Ala Ser His Lys Ile Phe Lys Met Glu Lys
225                 230                 235                 240

Gly Lys Val Val Lys Ser Val Glu Leu Asp Ala Pro Asn Tyr His Tyr
                245                 250                 255

Glu Glu Cys Ser Cys Tyr Pro Asn Ala Gly Glu Ile Thr Cys Val Cys
            260                 265                 270

Arg Asp Asn Trp His Gly Ser Asn Arg Pro Trp Val Ser Phe Asn Gln
        275                 280                 285

Asn Leu Glu Tyr Gln Ile Gly Tyr Ile Cys Ser Gly Val Phe Gly Asp
    290                 295                 300

Asn Pro Arg Pro Asn Asp Gly Thr Gly Ser Cys Gly Pro Val Ser Ser
305                 310                 315                 320

Asn Gly Ala Tyr Gly Val Lys Gly Phe Ser Phe Lys Tyr Gly Asn Gly
                325                 330                 335

Val Trp Ile Gly Arg Thr Lys Ser Thr Asn Ser Arg Ser Gly Phe Glu
            340                 345                 350

Met Ile Trp Asp Pro Asn Gly Trp Thr Glu Thr Asp Ser Ser Phe Ser
        355                 360                 365

Val Lys Gln Asp Ile Val Ala Ile Thr Asp Trp Ser Gly Tyr Ser Gly
```

```
                370                 375                 380
Ser Phe Val Gln His Pro Glu Leu Thr Gly Leu Asp Cys Ile Arg Pro
385                 390                 395                 400

Cys Phe Trp Val Glu Leu Ile Arg Gly Arg Pro Lys Glu Ser Thr Ile
                405                 410                 415

Trp Thr Ser Gly Ser Ser Ile Ser Phe Cys Gly Val Asn Ser Asp Thr
                420                 425                 430

Val Gly Trp Ser Trp Pro Asp Gly Ala Glu Leu Pro Phe Thr Ile Asp
                435                 440                 445

Lys

<210> SEQ ID NO 13
<211> LENGTH: 564
<212> TYPE: PRT
<213> ORGANISM: Influenza virus

<400> SEQUENCE: 13

Met Glu Lys Ile Val Leu Leu Phe Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Ala Asn Asp Leu Cys Tyr Pro Gly Asp Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Asn Ser Trp Ser Ser His Glu Ala Ser
    130                 135                 140

Leu Gly Val Ser Ser Ala Cys Pro Tyr Gln Gly Lys Ser Ser Phe Phe
145                 150                 155                 160

Arg Asn Val Val Trp Leu Ile Lys Lys Asn Asn Ala Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Arg Leu Tyr Gln
        195                 200                 205

Asn Pro Thr Thr Tyr Ile Ser Val Gly Thr Ser Thr Leu Asn Gln Arg
    210                 215                 220

Leu Val Pro Lys Ile Ala Thr Arg Ser Lys Val Asn Gly Gln Asn Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Leu Glu Tyr Gly
        275                 280                 285

Asn Cys Asn Thr Lys Cys Gln Thr Pro Met Gly Ala Ile Asn Ser Ser
```

-continued

```
                290                 295                 300
Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Thr Arg Gly Leu Phe Gly Ala Ile Ala Gly Phe Ile
                340                 345                 350

Glu Gly Gly Trp Gln Gly Met Val Asp Gly Trp Tyr Gly Tyr His His
                355                 360                 365

Ser Asn Glu Gln Gly Ser Gly Tyr Ala Ala Asp Lys Glu Ser Thr Gln
                370                 375                 380

Lys Ala Ile Asp Gly Val Thr Asn Lys Val Asn Ser Ile Ile Asp Lys
385                 390                 395                 400

Met Asn Thr Gln Phe Glu Ala Val Gly Arg Glu Phe Asn Asn Leu Glu
                405                 410                 415

Arg Arg Ile Glu Asn Leu Asn Lys Lys Met Glu Asp Gly Phe Leu Asp
                420                 425                 430

Val Trp Thr Tyr Asn Ala Glu Leu Leu Val Leu Met Glu Asn Glu Arg
                435                 440                 445

Thr Leu Asp Phe His Asp Ser Asn Val Lys Asn Leu Tyr Asp Lys Val
                450                 455                 460

Arg Leu Gln Leu Arg Asp Asn Ala Lys Glu Leu Gly Asn Gly Cys Phe
465                 470                 475                 480

Glu Phe Tyr His Lys Cys Asp Asn Glu Cys Met Glu Ser Val Arg Asn
                485                 490                 495

Gly Thr Tyr Asp Tyr Pro Gln Tyr Ser Glu Glu Ala Arg Leu Lys Arg
                500                 505                 510

Glu Glu Ile Ser Gly Val Lys Leu Glu Ser Ile Gly Thr Tyr Gln Ile
                515                 520                 525

Leu Ser Ile Tyr Ser Thr Val Ala Ser Ser Leu Ala Leu Ala Ile Met
                530                 535                 540

Val Ala Gly Leu Ser Leu Trp Met Cys Ser Asn Gly Ser Leu Gln Cys
545                 550                 555                 560

Arg Ile Cys Ile

<210> SEQ ID NO 14
<211> LENGTH: 469
<212> TYPE: PRT
<213> ORGANISM: Influenza virus

<400> SEQUENCE: 14

Met Asn Pro Asn Gln Lys Ile Thr Thr Ile Gly Ser Ile Cys Met Val
1               5                   10                  15

Ile Gly Ile Val Ser Leu Met Leu Gln Ile Gly Asn Ile Ile Ser Ile
                20                  25                  30

Trp Val Ser His Ser Ile Gln Thr Gly Asn Gln His Gln Ala Glu Pro
                35                  40                  45

Cys Asn Gln Ser Ile Ile Thr Tyr Glu Asn Asn Thr Trp Val Asn Gln
50                  55                  60

Thr Tyr Val Asn Ile Ser Asn Thr Asn Phe Leu Thr Glu Lys Ala Val
65                  70                  75                  80

Ala Ser Val Thr Leu Ala Gly Asn Ser Ser Leu Cys Pro Ile Ser Gly
                85                  90                  95

Trp Ala Val Tyr Ser Lys Asp Asn Gly Ile Arg Ile Gly Ser Lys Gly
```

-continued

```
            100                 105                 110

Asp Val Phe Val Ile Arg Glu Pro Phe Ile Ser Cys Ser His Leu Glu
        115                 120                 125

Cys Arg Thr Phe Phe Leu Thr Gln Gly Ala Leu Leu Asn Asp Lys His
    130                 135                 140

Ser Asn Gly Thr Val Lys Asp Arg Ser Pro His Arg Thr Leu Met Ser
145                 150                 155                 160
Cys Pro Val Gly Glu Ala Pro Ser Pro Tyr Asn Ser Arg Phe Glu Ser
                165                 170                 175
Val Ala Trp Ser Ala Ser Ala Cys His Asp Gly Thr Ser Trp Leu Thr
            180                 185                 190
Ile Gly Ile Ser Gly Pro Asp Asn Gly Ala Val Ala Val Leu Lys Tyr
        195                 200                 205

Asn Gly Ile Ile Thr Asp Thr Ile Lys Ser Trp Arg Asn Asn Ile Met
    210                 215                 220

Arg Thr Gln Glu Ser Glu Cys Ala Cys Val Asn Gly Ser Cys Phe Thr
225                 230                 235                 240
Val Met Thr Asp Gly Pro Ser Asn Gly Gln Ala Ser Tyr Lys Ile Phe
                245                 250                 255
Arg Ile Glu Lys Gly Lys Val Val Lys Ser Ala Glu Leu Asn Ala Pro
            260                 265                 270
Asn Tyr His Tyr Glu Glu Cys Ser Cys Tyr Pro Asp Ala Gly Glu Ile
        275                 280                 285

Thr Cys Val Cys Arg Asp Asn Trp His Gly Ser Asn Arg Pro Trp Val
    290                 295                 300

Ser Phe Asn Gln Asn Leu Glu Tyr Arg Ile Gly Tyr Ile Cys Ser Gly
305                 310                 315                 320
Val Phe Gly Asp Asn Pro Arg Pro Asn Asp Gly Thr Gly Ser Cys Gly
                325                 330                 335
Pro Val Ser Pro Lys Gly Ala Tyr Gly Ile Lys Gly Phe Ser Phe Lys
            340                 345                 350
Tyr Gly Asn Gly Val Trp Ile Gly Arg Thr Lys Ser Thr Asn Ser Arg
        355                 360                 365

Ser Gly Phe Glu Met Ile Trp Asp Pro Asn Gly Trp Thr Gly Thr Asp
    370                 375                 380

Ser Asn Phe Ser Val Lys Gln Asp Ile Val Ala Ile Thr Asp Trp Ser
385                 390                 395                 400
Gly Tyr Ser Gly Ser Phe Val Gln His Pro Glu Leu Thr Gly Leu Asp
                405                 410                 415
Cys Ile Arg Pro Cys Phe Trp Val Glu Leu Ile Arg Gly Arg Pro Lys
            420                 425                 430
Glu Ser Thr Ile Trp Thr Ser Gly Ser Ser Ile Ser Phe Cys Gly Val
        435                 440                 445

Asn Ser Asp Thr Val Gly Trp Ser Trp Pro Asp Gly Ala Glu Leu Pro
    450                 455                 460

Phe Thr Ile Asp Lys
465
```

<210> SEQ ID NO 15
<211> LENGTH: 564
<212> TYPE: PRT
<213> ORGANISM: Influenza virus

<400> SEQUENCE: 15

```
Met Glu Lys Ile Val Leu Leu Ala Thr Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Arg Thr His Asn Gly Lys Leu Cys Asp Leu Asn Gly Val Lys
50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
            85                  90                  95

Glu Lys Ala Ser Pro Ala Asn Asp Leu Cys Tyr Pro Gly Asn Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asn His Asp Ala Ser
130                 135                 140

Ser Gly Val Ser Ser Ala Cys Pro Tyr Leu Gly Arg Ser Ser Phe Phe
145                 150                 155                 160

Arg Asn Val Val Trp Leu Ile Lys Lys Asn Ser Ser Tyr Pro Thr Ile
            165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Arg Leu Tyr Gln
        195                 200                 205

Asn Pro Thr Thr Tyr Ile Ser Val Gly Thr Ser Thr Leu Asn Gln Arg
210                 215                 220

Leu Val Pro Glu Ile Ala Thr Arg Pro Lys Val Asn Gly Gln Ser Gly
225                 230                 235                 240

Arg Met Glu Phe Phe Trp Thr Ile Leu Lys Pro Asn Asp Ala Ile Asn
            245                 250                 255

Phe Glu Ser Asn Gly Asn Phe Ile Ala Pro Glu Tyr Ala Tyr Lys Ile
            260                 265                 270

Val Lys Lys Gly Asp Ser Thr Ile Met Lys Ser Glu Leu Glu Tyr Gly
        275                 280                 285

Asn Cys Asn Thr Lys Cys Gln Thr Pro Met Gly Ala Ile Asn Ser Ser
290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Thr
            325                 330                 335

Pro Gln Arg Glu Thr Arg Gly Leu Phe Gly Ala Ile Ala Gly Phe Ile
            340                 345                 350

Glu Gly Gly Trp Gln Gly Met Val Asp Gly Trp Tyr Gly Tyr His His
        355                 360                 365

Ser Asn Glu Gln Gly Ser Gly Tyr Ala Ala Asp Gln Glu Ser Thr Gln
        370                 375                 380

Lys Ala Ile Asp Gly Val Thr Asn Lys Val Asn Ser Ile Ile Asn Lys
385                 390                 395                 400

Met Asn Thr Gln Phe Glu Ala Val Gly Arg Glu Phe Asn Asn Leu Glu
            405                 410                 415

Arg Arg Ile Glu Asn Leu Asn Lys Lys Met Glu Asp Gly Phe Leu Asp
```

-continued

```
                  420                 425                 430
Val Trp Thr Tyr Asn Ala Glu Leu Leu Val Leu Met Glu Asn Glu Arg
            435                 440                 445

Thr Leu Asp Phe His Asp Ser Asn Val Lys Asn Leu Tyr Asp Lys Val
        450                 455                 460

Arg Leu Gln Leu Arg Asp Asn Ala Lys Glu Leu Gly Asn Gly Cys Phe
465                 470                 475                 480

Glu Phe Tyr His Lys Cys Asp Asn Glu Cys Met Glu Ser Val Lys Asn
                485                 490                 495

Gly Thr Tyr Asp Tyr Pro Gln Tyr Ser Glu Glu Ala Arg Leu Asn Arg
            500                 505                 510

Glu Glu Ile Ser Gly Val Lys Leu Glu Ser Met Gly Thr Tyr Gln Ile
        515                 520                 525

Leu Ser Ile Tyr Ser Thr Val Ala Ser Ser Leu Ala Leu Ala Ile Met
        530                 535                 540

Val Ala Gly Leu Ser Leu Trp Met Cys Ser Asn Gly Ser Leu Gln Cys
545                 550                 555                 560

Arg Ile Cys Ile

<210> SEQ ID NO 16
<211> LENGTH: 450
<212> TYPE: PRT
<213> ORGANISM: Influenza virus

<400> SEQUENCE: 16

Met Asn Pro Asn Gln Lys Ile Ile Thr Ile Gly Ser Ile Cys Met Val
1               5                   10                  15

Val Gly Ile Ile Ser Leu Met Leu Gln Ile Gly Asn Thr Ile Ser Val
            20                  25                  30

Trp Val Ser His Ile Ile Lys Thr Trp His Pro Asn Gln Pro Glu Pro
        35                  40                  45

Cys Asn Gln Ser Ile Asn Phe Tyr Thr Glu Gln Ala Ala Ala Ser Val
    50                  55                  60

Thr Leu Ala Gly Asn Ser Ser Leu Cys Pro Ile Ser Gly Trp Ala Ile
65                  70                  75                  80

Tyr Ser Lys Asp Asn Ser Ile Arg Ile Gly Ser Lys Gly Asp Val Phe
                85                  90                  95

Val Ile Arg Glu Pro Phe Ile Ser Cys Ser His Leu Glu Cys Arg Thr
            100                 105                 110

Phe Phe Leu Thr Gln Gly Ala Leu Leu Asn Asp Lys His Ser Asn Gly
        115                 120                 125

Thr Val Lys Asp Arg Ser Pro Tyr Arg Thr Leu Met Ser Cys Pro Val
    130                 135                 140

Gly Glu Ala Pro Ser Pro Tyr Asn Ser Arg Phe Glu Ser Val Ala Trp
145                 150                 155                 160

Ser Ala Ser Ala Cys His Asp Gly Ile Ser Trp Leu Thr Ile Gly Ile
                165                 170                 175

Ser Gly Pro Asp Asn Gly Ala Val Ala Val Leu Lys Tyr Asn Gly Ile
            180                 185                 190

Ile Thr Asp Thr Ile Lys Ser Trp Arg Asn Asn Thr Leu Arg Thr Gln
        195                 200                 205

Glu Ser Glu Cys Ala Cys Val Asn Gly Ser Cys Phe Thr Val Met Thr
    210                 215                 220

Asp Gly Pro Ser Asn Glu Gln Ala Ser Tyr Lys Ile Phe Lys Ile Glu
```

-continued

```
                225                 230                 235                 240
Lys Gly Arg Val Val Lys Ser Val Glu Leu Asn Ala Pro Asn Tyr His
                245                 250                 255

Tyr Glu Glu Cys Ser Cys Tyr Pro Asp Ala Gly Glu Ile Thr Cys Val
            260                 265                 270

Cys Arg Asp Asn Trp His Gly Ser Asn Arg Pro Trp Val Ser Phe Asn
            275                 280                 285

Gln Asn Leu Glu Tyr Gln Ile Gly Tyr Ile Cys Ser Gly Val Phe Gly
            290                 295                 300

Asp Ser Pro Arg Pro Asn Asp Gly Thr Gly Ser Cys Gly Pro Val Ser
305                 310                 315                 320

Leu Asn Gly Ala Tyr Gly Val Lys Gly Phe Ser Phe Lys Tyr Gly Asn
                325                 330                 335

Gly Val Trp Ile Gly Arg Thr Lys Ser Thr Ser Arg Ser Gly Phe
                340                 345                 350

Glu Met Ile Trp Asp Pro Asn Gly Trp Thr Glu Thr Asp Ser Ser Phe
            355                 360                 365

Ser Leu Lys Gln Asp Ile Ile Ala Ile Thr Asp Trp Ser Gly Tyr Ser
            370                 375                 380

Gly Ser Phe Ile Gln His Pro Glu Leu Thr Gly Leu Asn Cys Met Arg
385                 390                 395                 400

Pro Cys Phe Trp Val Glu Leu Ile Arg Gly Arg Pro Lys Glu Lys Thr
                405                 410                 415

Ile Trp Thr Ser Gly Ser Ser Ile Ser Phe Cys Gly Val Asn Ser Asp
                420                 425                 430

Thr Val Gly Trp Ser Trp Pro Asp Gly Ala Glu Leu Pro Tyr Thr Ile
            435                 440                 445

Asp Lys
    450

<210> SEQ ID NO 17
<211> LENGTH: 564
<212> TYPE: PRT
<213> ORGANISM: Influenza virus

<400> SEQUENCE: 17

Met Glu Lys Ile Val Leu Leu Leu Ala Thr Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Arg Thr His Asn Gly Lys Leu Cys Asp Leu Asn Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Ser Pro Ala Asn Asp Leu Cys Tyr Pro Gly Asn Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asn His Asp Ala Ser
    130                 135                 140
```

```
Ser Gly Val Ser Ser Ala Cys Pro Tyr Leu Gly Arg Ser Ser Phe Phe
145                 150                 155                 160

Arg Asn Val Val Trp Leu Ile Lys Lys Asn Ser Ser Tyr Pro Thr Ile
                165                 170                 175

Lys Arg Ser Tyr Asn Asn Thr Asn Gln Glu Asp Leu Leu Val Leu Trp
                180                 185                 190

Gly Ile His His Pro Asn Asp Ala Ala Glu Gln Thr Arg Leu Tyr Gln
                195                 200                 205

Asn Pro Thr Thr Tyr Ile Ser Val Gly Thr Ser Thr Leu Asn Gln Arg
210                 215                 220

Leu Val Ser Glu Ile Ala Thr Arg Pro Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
                260                 265                 270

Val Lys Lys Gly Asp Ser Thr Ile Met Lys Ser Glu Leu Glu Tyr Gly
                275                 280                 285

Asn Cys Asn Thr Lys Cys Gln Thr Pro Met Gly Ala Ile Asn Ser Ser
290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Thr
                325                 330                 335

Pro Gln Arg Glu Thr Arg Gly Leu Phe Gly Ala Ile Ala Gly Phe Ile
                340                 345                 350

Glu Gly Gly Trp Gln Gly Met Val Asp Gly Trp Tyr Gly Tyr His His
                355                 360                 365

Ser Asn Glu Gln Gly Ser Gly Tyr Ala Ala Asp Gln Glu Ser Thr Gln
                370                 375                 380

Lys Ala Ile Asp Gly Val Thr Asn Lys Val Asn Ser Ile Ile Asn Lys
385                 390                 395                 400

Met Asn Thr Gln Phe Glu Ala Val Gly Arg Glu Phe Asn Asn Leu Glu
                405                 410                 415

Arg Arg Ile Glu Asn Leu Asn Lys Lys Met Glu Asp Gly Phe Leu Asp
                420                 425                 430

Val Trp Thr Tyr Asn Ala Glu Leu Leu Val Leu Met Glu Asn Glu Arg
                435                 440                 445

Thr Leu Asp Phe His Asp Ser Asn Val Lys Asn Leu Tyr Asp Lys Val
                450                 455                 460

Arg Leu Gln Leu Arg Asp Asn Ala Lys Glu Leu Gly Asn Gly Cys Phe
465                 470                 475                 480

Glu Phe Tyr His Lys Cys Asp Asn Glu Cys Met Glu Ser Val Lys Asn
                485                 490                 495

Gly Thr Tyr Asp Tyr Pro Gln Tyr Ser Glu Glu Ala Arg Leu Asn Arg
                500                 505                 510

Glu Glu Ile Ser Gly Val Lys Leu Glu Ser Met Gly Thr Tyr Gln Ile
                515                 520                 525

Leu Ser Ile Tyr Ser Thr Val Ala Ser Ser Leu Ala Leu Ala Ile Met
530                 535                 540

Val Ala Gly Leu Ser Leu Trp Met Cys Ser Asn Gly Ser Leu Gln Cys
545                 550                 555                 560

Arg Ile Cys Ile
```

<210> SEQ ID NO 18
<211> LENGTH: 450
<212> TYPE: PRT
<213> ORGANISM: Influenza virus

<400> SEQUENCE: 18

```
Met Asn Pro Asn Gln Lys Ile Ile Thr Ile Gly Ser Ile Cys Met Val
1               5                   10                  15

Val Gly Ile Ile Ser Leu Met Leu Gln Ile Gly Asn Thr Ile Ser Val
            20                  25                  30

Trp Val Ser His Ile Ile Lys Thr Trp His Pro Asn Gln Pro Glu Pro
        35                  40                  45

Cys Asn Gln Ser Ile Asn Phe Tyr Thr Glu Gln Ala Ala Ala Ser Val
    50                  55                  60

Thr Leu Ala Gly Asn Ser Ser Leu Cys Pro Ile Ser Gly Trp Ala Ile
65                  70                  75                  80

Tyr Ser Lys Asp Asn Ser Ile Arg Ile Gly Ser Lys Gly Asp Val Phe
                85                  90                  95

Val Ile Arg Glu Pro Phe Ile Ser Cys Ser His Leu Glu Cys Arg Thr
            100                 105                 110

Phe Phe Leu Thr Gln Gly Ala Leu Leu Asn Asp Lys His Ser Asn Gly
        115                 120                 125

Thr Val Lys Asp Arg Ser Pro Tyr Arg Thr Leu Met Ser Cys Pro Val
    130                 135                 140

Gly Glu Ala Pro Ser Pro Tyr Asn Ser Arg Phe Glu Ser Val Ala Trp
145                 150                 155                 160

Ser Ala Ser Ala Cys His Asp Gly Ile Ser Trp Leu Thr Ile Gly Ile
                165                 170                 175

Ser Gly Pro Asp Asn Gly Ala Val Ala Val Leu Lys Tyr Asn Gly Ile
            180                 185                 190

Ile Thr Asp Thr Ile Lys Ser Trp Arg Asn Asn Thr Leu Arg Thr Gln
        195                 200                 205

Glu Ser Glu Cys Ala Cys Val Asn Gly Ser Cys Phe Thr Val Met Thr
    210                 215                 220

Asp Gly Pro Ser Asn Glu Gln Ala Ser Tyr Lys Ile Phe Lys Ile Glu
225                 230                 235                 240

Lys Gly Arg Val Val Lys Ser Val Glu Leu Asn Ala Pro Asn Tyr His
                245                 250                 255

Tyr Glu Glu Cys Ser Cys Tyr Pro Asp Ala Gly Glu Ile Thr Cys Val
            260                 265                 270

Cys Arg Asp Asn Trp His Gly Ser Asn Arg Pro Trp Val Ser Phe Asn
        275                 280                 285

Gln Asn Leu Glu Tyr Gln Ile Gly Tyr Ile Cys Ser Gly Val Phe Gly
    290                 295                 300

Asp Ser Pro Arg Pro Asn Asp Gly Thr Gly Ser Cys Gly Pro Val Ser
305                 310                 315                 320

Leu Asn Gly Ala Tyr Gly Val Lys Gly Phe Ser Phe Lys Tyr Gly Asn
                325                 330                 335

Gly Val Trp Ile Gly Arg Thr Lys Ser Thr Ser Arg Ser Gly Phe
            340                 345                 350

Glu Met Ile Trp Asp Pro Asn Gly Trp Thr Glu Thr Asp Ser Ser Phe
        355                 360                 365

Ser Leu Lys Gln Asp Ile Ile Ala Ile Thr Asp Trp Ser Gly Tyr Ser
```

-continued

```
                370                 375                 380
Gly Ser Phe Ile Gln His Pro Glu Leu Thr Gly Leu Asn Cys Met Arg
385                 390                 395                 400

Pro Cys Phe Trp Val Glu Leu Ile Arg Gly Arg Pro Lys Glu Lys Thr
                405                 410                 415

Ile Trp Thr Ser Gly Ser Ser Ile Ser Phe Cys Gly Val Asn Ser Asp
                420                 425                 430

Thr Val Gly Trp Ser Trp Pro Asp Gly Ala Glu Leu Pro Tyr Thr Ile
                435                 440                 445

Asp Lys
    450

<210> SEQ ID NO 19
<211> LENGTH: 558
<212> TYPE: PRT
<213> ORGANISM: Influenza virus

<400> SEQUENCE: 19

Met Glu Ala Ile Pro Leu Ile Thr Ile Leu Leu Val Val Thr Ala Ser
1               5                   10                  15

Asn Ala Asp Lys Ile Cys Ile Gly Tyr Gln Ser Thr Asn Ser Thr Glu
                20                  25                  30

Thr Val Asp Thr Leu Thr Glu Asn Asn Val Pro Val Thr His Ala Lys
            35                  40                  45

Glu Leu Leu His Thr Glu His Asn Gly Met Leu Cys Ala Thr Asn Leu
    50                  55                  60

Gly Arg Pro Leu Ile Leu Asp Thr Cys Thr Ile Glu Gly Leu Ile Tyr
65                  70                  75                  80

Gly Asn Pro Ser Cys Asp Leu Leu Leu Gly Gly Arg Glu Trp Ser Tyr
                85                  90                  95

Ile Val Glu Arg Pro Ser Ala Val Asn Gly Met Cys Tyr Pro Gly Asn
                100                 105                 110

Val Glu Asn Leu Glu Glu Leu Arg Ser Phe Phe Ser Ser Ala Ser Ser
            115                 120                 125

Tyr Gln Arg Ile Gln Ile Phe Pro Asp Thr Ile Trp Asn Val Ser Tyr
    130                 135                 140

Ser Gly Thr Ser Lys Ala Cys Ser Asp Ser Phe Tyr Arg Ser Met Arg
145                 150                 155                 160

Trp Leu Thr Gln Lys Asn Asn Ala Tyr Pro Ile Gln Asp Ala Gln Tyr
                165                 170                 175

Thr Asn Asn Arg Gly Lys Ser Ile Leu Phe Met Trp Gly Ile Asn His
                180                 185                 190

Pro Pro Thr Asp Thr Ala Gln Thr Asn Leu Tyr Thr Arg Thr Asp Thr
            195                 200                 205

Thr Thr Ser Val Ala Thr Glu Asp Ile Asn Arg Thr Phe Lys Pro Val
    210                 215                 220

Ile Gly Pro Arg Pro Leu Val Asn Gly Leu Gln Gly Arg Ile Asp Tyr
225                 230                 235                 240

Tyr Trp Ser Val Leu Lys Pro Gly Gln Thr Leu Arg Val Arg Ser Asn
                245                 250                 255

Gly Asn Leu Ile Ala Pro Trp Tyr Gly His Ile Leu Ser Gly Glu Ser
                260                 265                 270

His Gly Arg Ile Leu Lys Thr Asp Leu Asn Ser Gly Ser Cys Val Val
            275                 280                 285
```

```
Gln Cys Gln Thr Glu Arg Gly Gly Leu Asn Thr Thr Leu Pro Phe His
    290                 295                 300

Asn Val Ser Lys Tyr Ala Phe Gly Asn Cys Pro Lys Tyr Val Gly Val
305                 310                 315                 320

Lys Ser Leu Lys Leu Ala Val Gly Leu Arg Asn Val Pro Ala Arg Ser
                325                 330                 335

Ser Arg Gly Leu Phe Gly Ala Ile Ala Gly Phe Ile Glu Gly Gly Trp
            340                 345                 350

Ser Gly Leu Val Ala Gly Trp Tyr Gly Phe Gln His Ser Asn Asp Gln
        355                 360                 365

Gly Val Gly Ile Ala Ala Asp Arg Asp Ser Thr Gln Arg Ala Ile Asp
    370                 375                 380

Lys Ile Thr Ser Lys Val Asn Asn Ile Val Asp Lys Met Asn Lys Gln
385                 390                 395                 400

Tyr Glu Ile Ile Asp His Glu Phe Ser Glu Val Glu Asn Arg Leu Asn
                405                 410                 415

Met Ile Asn Asn Lys Ile Asp Asp Gln Ile Gln Asp Ile Trp Ala Tyr
            420                 425                 430

Asn Ala Glu Leu Leu Val Leu Leu Glu Asn Gln Lys Thr Leu Asp Glu
        435                 440                 445

His Asp Ala Asn Val Asn Asn Leu Tyr Asn Lys Val Lys Arg Ala Leu
    450                 455                 460

Gly Ser Asn Ala Met Glu Asp Gly Lys Gly Cys Phe Glu Leu Tyr His
465                 470                 475                 480

Lys Cys Asp Asp Gln Cys Met Glu Thr Ile Arg Asn Gly Thr Tyr Asn
                485                 490                 495

Arg Arg Lys Tyr Lys Glu Glu Ser Arg Leu Glu Arg Gln Lys Ile Glu
            500                 505                 510

Gly Val Lys Leu Glu Ser Glu Gly Thr Tyr Lys Ile Leu Thr Ile Tyr
        515                 520                 525

Ser Thr Val Ala Ser Ser Leu Val Ile Ala Met Gly Phe Ala Ala Phe
    530                 535                 540

Leu Phe Trp Ala Met Ser Asn Gly Ser Cys Arg Cys Asn Ile
545                 550                 555

<210> SEQ ID NO 20
<211> LENGTH: 469
<212> TYPE: PRT
<213> ORGANISM: Influenza virus

<400> SEQUENCE: 20

Met Asn Pro Asn Gln Lys Ile Ile Ala Ile Gly Ser Val Ser Leu Thr
1               5                   10                  15

Ile Ala Thr Ile Cys Leu Leu Met Gln Ile Ala Ile Leu Ala Thr Thr
                20                  25                  30

Met Thr Leu His Phe Lys Gln Asn Glu Cys Ile Asn Ser Ser Asn Asn
            35                  40                  45

Gln Val Val Pro Cys Glu Pro Ile Ile Ile Glu Arg Asn Ile Thr Glu
        50                  55                  60

Ile Val His Leu Asn Ser Thr Thr Leu Glu Lys Glu Ile Cys Pro Lys
65                  70                  75                  80

Val Ala Asp Tyr Arg Asn Trp Ser Lys Pro Gln Cys Gln Ile Thr Gly
                85                  90                  95

Phe Ala Pro Phe Ser Lys Asp Asn Ser Ile Arg Leu Ser Ala Gly Gly
            100                 105                 110
```

```
Asp Ile Trp Val Thr Arg Glu Pro Tyr Val Ser Cys Gly Leu Gly Lys
        115                 120                 125

Cys Tyr Gln Phe Ala Leu Gly Gln Gly Thr Thr Leu Glu Asn Lys His
    130                 135                 140

Ser Asn Gly Thr Ala His Asp Arg Thr Pro His Arg Thr Leu Leu Met
145                 150                 155                 160

Asn Glu Leu Gly Val Pro Phe His Leu Ala Thr Lys Gln Val Cys Ile
                165                 170                 175

Ala Trp Ser Ser Ser Cys His Asp Gly Lys Ala Trp Leu His Val
            180                 185                 190

Cys Val Thr Gly Asp Asp Arg Asn Ala Thr Ala Ser Ile Ile Tyr Asp
        195                 200                 205

Gly Ile Leu Val Asp Ser Ile Gly Ser Trp Ser Lys Asn Ile Leu Arg
        210                 215                 220

Thr Gln Glu Ser Glu Cys Val Cys Ile Asn Gly Thr Cys Ala Val Val
225                 230                 235                 240

Met Thr Asp Gly Ser Ala Ser Gly Arg Ala Asp Thr Arg Ile Leu Phe
                245                 250                 255

Ile Arg Glu Gly Lys Ile Ala His Ile Ser Pro Leu Ser Gly Ser Ala
            260                 265                 270

Gln His Val Glu Glu Cys Ser Cys Tyr Pro Arg Tyr Pro Glu Val Arg
        275                 280                 285

Cys Val Cys Arg Asp Asn Trp Lys Gly Ser Asn Arg Pro Val Leu Tyr
        290                 295                 300

Ile Asn Met Ala Asn Tyr Ser Ile Asp Ser Ser Tyr Val Cys Ser Gly
305                 310                 315                 320

Leu Val Gly Asp Thr Pro Arg Asn Asp Asp Arg Ser Ser Ser Ser Asn
                325                 330                 335

Cys Arg Asp Pro Asn Asn Glu Arg Gly Ala Pro Gly Val Lys Gly Trp
            340                 345                 350

Ala Phe Asp Asn Gly Asn Asp Ile Trp Met Gly Arg Thr Ile Lys Lys
        355                 360                 365

Asp Ser Arg Ser Gly Tyr Glu Thr Phe Arg Val Ile Gly Gly Trp Thr
        370                 375                 380

Thr Ala Asn Ser Lys Ser Gln Ile Asn Arg Gln Val Ile Val Asp Ser
385                 390                 395                 400

Asp Asn Ser Ser Gly Tyr Ser Gly Ile Phe Ser Val Glu Gly Lys Ser
                405                 410                 415

Cys Ile Asn Arg Cys Phe Tyr Val Glu Leu Ile Arg Gly Arg Pro Lys
            420                 425                 430

Glu Thr Arg Val Trp Trp Thr Ser Asn Ser Ile Ile Val Phe Cys Gly
        435                 440                 445

Thr Ser Gly Thr Tyr Gly Thr Gly Ser Trp Pro Asp Gly Ala Asn Ile
        450                 455                 460

Asn Phe Met Pro Ile
465

<210> SEQ ID NO 21
<211> LENGTH: 39
<212> TYPE: DNA
<213> ORGANISM: Influenza virus

<400> SEQUENCE: 21
cctcaaagag agagaagaag aaaaaagaga ggattattt                    39
```

-continued

```
<210> SEQ ID NO 22
<211> LENGTH: 13
<212> TYPE: PRT
<213> ORGANISM: Influenza virus

<400> SEQUENCE: 22

Pro Gln Arg Glu Arg Arg Arg Lys Lys Arg Gly Leu Phe
1               5                   10
```